US008552067B2

(12) United States Patent
Verkman et al.

(10) Patent No.: US 8,552,067 B2
(45) Date of Patent: Oct. 8, 2013

(54) MACROMOLECULAR CONJUGATES OF CYSTIC FIBROSIS TRANSMEMBRANE CONDUCTANCE REGULATOR PROTEIN INHIBITORS AND USES THEREFOR

(75) Inventors: Alan S. Verkman, San Francisco, CA (US); Nitin D. Sonawane, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1339 days.

(21) Appl. No.: 11/960,521

(22) Filed: Dec. 19, 2007

(65) Prior Publication Data

US 2008/0171793 A1 Jul. 17, 2008

Related U.S. Application Data

(60) Provisional application No. 60/876,616, filed on Dec. 22, 2006.

(51) Int. Cl.
*A61K 31/15* (2006.01)
*A61K 31/7012* (2006.01)
*A61K 31/165* (2006.01)
*A61K 31/195* (2006.01)
*A61K 31/47* (2006.01)

(52) U.S. Cl.
USPC ............. 514/639; 514/53; 514/614; 514/563; 514/313

(58) Field of Classification Search
USPC .................................. 514/639, 614, 615, 531
See application file for complete search history.

(56) References Cited

U.S. PATENT DOCUMENTS

| 5,023,333 | A | 6/1991 | Hubele | 546/175 |
|---|---|---|---|---|
| 5,359,131 | A * | 10/1994 | Cardin et al. | 562/51 |
| 6,172,108 | B1 | 1/2001 | Vega et al. | 514/485 |
| 6,331,555 | B1 | 12/2001 | Hirth et al. | 514/378 |
| 6,410,053 | B1 * | 6/2002 | Taylor | 424/488 |
| 7,235,573 | B2 | 6/2007 | Verkman et al. | 514/369 |
| 7,414,037 | B2 * | 8/2008 | Verkman et al. | 514/53 |
| 7,638,543 | B2 | 12/2009 | Verkman et al. | 514/369 |
| 2005/0239740 | A1 * | 10/2005 | Verkman et al. | 514/53 |
| 2009/0048207 | A1 | 2/2009 | Verkman et al. | 514/53 |
| 2009/0253799 | A1 | 10/2009 | Verkman et al. | 514/586 |
| 2010/0130571 | A1 | 5/2010 | Verkman et al. | 514/369 |
| 2011/0119775 | A1 * | 5/2011 | Verkman et al. | 800/9 |

FOREIGN PATENT DOCUMENTS

| EP | 0 952 159 | 10/1999 |
|---|---|---|
| GB | 1 334 400 | 10/1973 |
| GB | 1 446 980 | 8/1976 |
| GB | 2 107 074 | 4/1983 |
| JP | 59-162541 | 9/1984 |
| WO | WO01/30333 | 5/2001 |
| WO | WO2005/094374 | 10/2005 |
| WO | WO2008/079897 | 7/2008 |
| WO | WO2009/120803 | 10/2009 |
| WO | WO2009/146144 | 12/2009 |

OTHER PUBLICATIONS

Bies et al. Advanced Drug Delivery Reviews 56 (2004) 425-435.*
Clarke et al., "Defective Epithelial Chloride Transport in a Gene-Targeted Mouse Model of Cystic Fibrosis," Science 257:1125-1128, 1992.
Edwards et al., "Induction of a glibenclamide-sensitive K-current by modification of a delayed rectifier channel in rat portal vein and insulinoma cells," Br. J. Pharmacol. 110:1280-1281, 1993.
Field, "Intestinal ion transport and the pathophysiology of diarrhea," The Journal of Clinical Investigation 111(7):931-943, 2003.
Gabriel et al., "Cystic Fibrosis Heterozygote Resistance to Cholera Toxin in the Cystic Fibrosis Mouse Model," Science 266:107-109, 1994.
Oi et al., "Identification in traditional herbal medications and confirmation by synthesis of factors that inhibit cholera toxin-induced fluid accumulation," Proc. Natl. Acad. Sci. USA 99(5):3042-3046, 2002.
Aminabhavi et al., "Synthesis and Characterization of Biologically Active Organosilicon and Organotin Complexes of Phenylglycyl Hydrazones" Inorganic Chimica Acta 135: 139-143, 1987.
Al-Awqati, "Alternative treatment for secretory diarrhea revealed in a new class of CFTR inhibitors" J. Clin. Invest. 110(11): 1599-1601, 2002.
Beresnevicius et al., "Interaction of aminoquinolines with unsaturated carboxylic acids. 1. Synthesis of N-quinolyl-β-alanines and their biological activity" Chemistry of Heterocyclic Compounds, Translation of Khimiya Geterotsiklicheskikh Soedinenii, New York, 36(4): 432-438, 2000. (Abstract).
Bies et al., "Lectin-mediated drug targeting: history and applications" Adv. Drug Deliv. Rev. 56:425-435, 2004.
Boucher, "New concepts of the pathogenesis of cystic fibrosis lung disease" Eur. Respir. J. 23:146-158, 2004.
Brock et al., "Selective Open-channel Block of Shaker (Kv1) Potassium Channels by S-nitrosodithiothreitol (SNDTT)" J. Gen. Physiol. 118: 113-133, 2001.
Caci et al., "Evidence for direct CFTR inhibition by CFTR$_{inh}$-172 based on Arg$^{347}$ mutagenesis" Biochem. J. 413(1): 135-142, 2008.
Carmeliet, "Electrophysiology on the Molecular Way" Verh. K. Acad. Geneeskd. Belg. 55: 5-26, 1993.
CAS Registry No. 594869-56-4, Sep. 29, 2003.
CAS Registry No. 594870-13-0, Sep. 29, 2003.
CAS Registry No. 594870-90-3, Sep. 29, 2003.
CAS Registry No. 594871-24-6, Sep. 29, 2003.
CAS Registry No. 595550-90-6, Sep. 30, 2003.
CAS Registry No. 595552-29-7, Sep. 30, 2003.
CAS Registry No. 595553-21-2, Sep. 30, 2003.
CAS Registry No. 601498-88-8, Oct. 9, 2003.
CAS Registry No. 601498-97-9, Oct. 9, 2003.

(Continued)

*Primary Examiner* — Anoop Singh
*Assistant Examiner* — Anna Falkowitz
(74) *Attorney, Agent, or Firm* — Seed IP Law Group PLLC

(57) ABSTRACT

Provided herein are bioactive agents comprising a compound that inhibits the ion transport activity of a cystic fibrosis transmembrane conductance regulator (CFTR) and that is linked to a macromolecule that interacts with a cell that expresses CFTR. The bioactive agents described herein are useful for treating diseases, disorders, and sequelae of diseases, disorders, and conditions that are associated with aberrantly increased CFTR activity, for example, secretory diarrhea.

37 Claims, 13 Drawing Sheets

(56) References Cited

OTHER PUBLICATIONS

CAS Registry No. 606483-72-1, Oct. 19, 2003.
CAS Registry No. 610257-12-0, Oct. 29, 2003.
CAS Registry No. 640698-93-7, Jan. 23, 2004.
CAS Registry No. 640704-49-0, Jan. 23, 2004.
CAS Registry No. 643741-81-5, Jan. 30, 2004.
CAS Registry No. 664312-09-8, Mar. 18, 2004.
Chao et al., "Activation of intestinal CFTR Cl⁻ channel by heat-stable enterotoxin and guanylin via cAMP-dependent protein kinase" The EMBO Journal 13(5): 1065-1072, 1994.
Chemical Abstract, vol. 55, No. 14, Jul. 10, 1961, (Columbus, OH, USA), pp. 13350-13351, see abstract No. 13350h-1, Kondo et al., "N-Arylglycine Series Chemotherapeutics. I. Synthesis of Aryl Sulfone Derivatives," Yakugaku Zasshi, 1961, vol. 81, pp. 97-100.
Clark et al., "Lectin-mediated mucosal delivery of drugs and microparticles" Adv. Drug. Deliv. Rev. 43: 207-223, 2000.
Davidow et al., "The cystic fibrosis transmembrane conductance regulator mediated transepithelial fluid secretion by human autosomal dominant polycystic kidney disease epithelium in vitro" Kidney Int. 50: 208-218, 1996.
Dawson et al., "CFTR: Mechanism of Anion Conduction" Physiological Reviews 79(Supp. No. 1): S47-S75, 1999.
Gabor et al., "The lectin-cell interaction and its implications to intestinal lectin-mediated drug delivery" Adv. Drug. Deliv. Rev. 56: 459-480, 2004.
Galietta et al., "Cell-based assay for high-throughput quantitative screening of CFTR chloride transport agonists" Am. J. Physiol. Cell Physiol. 281(5): C1734-C1742, 2001.
Giri et al., "Organo-fluorine compounds. I. Synthesis of some substituted glycines and related compounds of potential biological activity" Journal of the Indian Chemical Society 46(5): 441-443, 1969. (Abstract).
Grubb et al., "Pathophysiology of Gene-Targeted Mouse Models for Cystic Fibrosis" Physiological Reviews 79 (Suppl. No. 1): S193-S214, 1999.
Gunther et al., "Concanavalin a Derivatives with Altered Biological Activities" Proc. Nat. Acad. Sci. USA 70(4): 1012-1016, 1973.
Hamill et al., "Improved Patch-Clamp Techniques for High-Resolution Current Recording from Cells and Cell-Free Membrane Patches" Pflugers Arch 391: 85-100, 1981.
Hammam et al., "Synthesis and reactions of 1,2,4-oxadiazole derivates of expected biological activity" Egyptian Journal of Chemistry 27(3): 407-411, 1985. (Abstract).
Hanaoka et al., "A role for CFTR in human autosomal dominant polycystic kidney disease" Am. J. Physiol. 270: C389-C399, 1996.
Jayaraman et al., "Submucosal gland secretions in airways from cystic fibrosis patients have normal [Na⁺] and pH but elevated viscosity" Proc. Natl. Acad. Sci. USA 98(14): 8119-8123, 2001.
Jiang et al., "Photoisomerization in dendrimers by harvesting of low-energy photons" Nature 388: 454-456, 1997.
Kilpatrick et al., "Purification and Separation of Tomato Isolectins by Chromatofocusing" Anal. Biochem. 134: 205-209, 1983.
Kilpatrick et al., "Tomato lectin resists digestion in the mammalian alimentary canal and binds to intestinal villi without deleterious effects" FEBS Lett. 185(2): 299-305, 1985.
Kimberg et al., "Stimulation of Intestinal Mucosal Adenyl Cyclase by Cholera Enterotoxin and Prostaglandins" the Journal of Clinical Investigation 50: 1218-1230, 1971.
Kunzelmann et al., "Electrolyte Transport in the Mammalian Colon: Mechanisms and Implications for Disease" Physiol. Rev. 82: 245-289, 2002.
Li et al., "The relationship between cell proliferation, Cl⁻ secretion, and renal cyst growth: A study using CFTR inhibitors" Kidney Int. 66: 1926-1938, 2004.
Lohi et al., "Upregulation of CFTR expression but not SLC26A3 and SLC9A3 in ulcerative colitis" Am. J. Physiol. Gastrointest. Liver Physiol. 283: G567-G575, 2002.
Loris et al., "Legume lectin structure" Biochimica et Biophysica Acta 1383: 9-36, 1998.
Ma et al., "Thiazolidinone CFTR inhibitor identified by high-throughput screening blocks cholera toxin-induced intestinal fluid secretion" The Journal of Clinical Investigation 110(11): 1651-1658, 2002.
Ma et al., "High-affinity Activators of Cystic Fibrosis Transmembrane Conductance Regulator (CFTR) Chloride Conductance Identified by High-throughput Screening" The Journal of Biological Chemistry 277(40): 37235-37241, 2002.
Mall et al., "The ΔF508 Mutation Results in Loss of CFTR Function and Mature Protein in Native Human Colon" Gastroenterology 126: 32-41, 2004.
Mazur et al., Derivatives of N-(4-quinazolinyl)-α-amino and qunazolin-4-on-3-yl-carboxylic acids and their antimicrobial activity Farmatsevtichnii Zhurnal, Kiev, (4): 34-37, 1980. (Abstract).
McCarty, "Permeation Through the CFTR Chloride Channel" The Journal of Experimental Biology 203: 1947-1962, 2000.
Misra et al., "Studies on 1,3,5-5-Triazine: Synthesis of Some Possible Antituberculous Compounds" Journal of the Indian Chemical Society 48(5): 448-450, 1971.
Misra et al., "Possible antituberculous compounds. XV. N-2-Thiazolyglycines, 1-acyl-4-arylsemicarbazides, 1-acyl-4-arylthiosemicarbazides, and N1-(N-arylglycl)-N2-(arylidane or alkylidene) hydrazines" Journal of the Indian Chemical Society 40(9): 799-802, 1963. (Abstract).
Muanprasat et al., "Discovery of Glycine Hydrazide Pore-occluding CFTR Inhibitors: Mechanism, Structure-Activity Analysis, and In Vivo Efficacy" Journal of General Physiology 124(2): 125-137, 2004.
Nachbar et al., "Lectins in the U.S. Diet. Isolation and characterization of a lectin from the tomato (*Lycophersicon esculentum*)" The Journal of Biological Chemistry 255(5): 2056-2061, 1980.
Noone et al., "'CFTR-opathies': disease phenotypes associated with cystic fibrosis transmembrane regulator gene mutations" Respir. Res. 2: 328-332, 2001.
O'Sullivan et al., "Cystic Fibrosis and the Phenotype Expression of Autosomal Dominant Polycystic Kidney Disease" Am. J. Kidney Dis. 32(6): 976-983, 1998.
Pilewski et al., "Role of CFTR in Airway Disease" Physiological Reviews 79(Supp. No. 1): S215-S255, 1999.
Pottosin et al., "Cooperative Block of the Plant Endomembrane Ion Channel by Ruthenium Red" Biophysical Journal 77: 1973-1979, 1999.
Quinton, "Physiological Basis of Cystic Fibrosis: A Historical Perspective" Physiological Reviews 79(Supp. No. 1): S3-S22, 1999.
Rabe et al., "Cl⁻ channel inhibition by glibenclamide is not specific for the CFTR-type Cl⁻ channel" Pflugers Arch. Eur. J. Physiol. 429: 659-662, 1995.
Ramamurthy et al., "Synthesis and Antitubercular Activity of N-(2-Naphthyl)glycine Hydrazide Analogues" Journal of Medicinal Chemistry 32: 2421-2426, 1989.
Salinas et al., "Submucosal gland dysfunction as a primary defect in cystic fibrosis" The FASEB Journal 19: 431-433, 2005.
Sheppard et al., "Mechanism of glibenclamide inhibition of cystic fibrosis transmembrane conductance regulator Cl⁻ channels expressed in a murine cell line" Journal of Physiology 503.2: 333-346, 1997.
Schultz et al., "Pharmacology of CFTR Chloride Channel Activity" Physiological Reviews 79(Supp. No. 1): S109-S144, 1999.
Smart, "Lectin-mediated drug delivery in the oral cavity" Adv. Drug. Deliv. Rev. 56: 481-489, 2004.
Snyder et al., "The magnitude of the global problem of acute diarrhoeal disease: a review of active surveillance data" Bulletin of the World Health Organization 60(4): 605-613, 1982.
Solomko et al., "N-Aryl-β-amino acids. V. Hydrazides of N-aryl-β-alanines" Khimiko-Farmatsevticheskii Zhumal 5(11): 18-21, 1971. (Abstract).
Sonawane et al., "Thiazolidinone CFTR inhibitors with improved water solubility identified by structure-activity analysis" Bioorganic & Medicinal Chemistry 16: 8187-8195, 2008.
Sonawane et al., "Lectin Conjugates as Potent, Nonabsorbable CFTR Inhibitors for Reducing Intestinal Fluid Secretion in Cholera" Gastroenterology 132(4): 1234-1244, 2007.

Sonawane et al., "Luminally active, nonabsorbable CFTR inhibitors as potential therapy to reduce intestinal fluid loss in cholera" The FASEB Journal, express article 10.1096/fj.05-4818fje, Nov. 29, 2005.

Sonawane et al., "Nanomolar CFTR Inhibition by Pore-Occluding Divalent Polyethylene Glycol-Malonic Acid Hydrazides" Chemistry & Biology 15(7): 718-728, 2008.

Spira et al., "Simple Adult Rabbit Model for *Vibrio cholera* and Enterotoxigenic *Escherichia coli* Diarrhea" Infection and Immunity 32(2): 739-747, 1981.

Strong et al., "Localization of Cystic Fibrosis Transmembrane Conductance Regulator mRNA in the Human Gastrointestinal Tract by In Situ Hybridization" The Journal of Clinical Investigation 93: 347-354, 1994.

Sullivan et al., "Epithelial Transport in Polycystic Kidney Disease" Physiological Reviews 78(4): 1165-1191, 1998.

Takeda et al., "Detection of Cholera Enterotoxin Activity in Suckling Hamsters" Infection and Immunity 19(2): 752-754, 1978.

Thiagarajah et al., "A small molecule CFTR inhibitor produces cystic fibrosis-like submucosal gland fluid secretions in normal airways" FASEB J 18: 875-877, 2004.

Thiagarajah et al., "CFTR pharmacology and its role in intestinal fluid secretion" Current Opinion in Pharmacology 3: 594-599, 2003.

Thiagarajah et al., "Prevention of Toxin-Induced Intestinal Ion and Fluid Secretion by a Small-Molecule CFTR Inhibitor" Gastroenterology 126: 511-519, 2004.

Thiagarajah et al., "New drug targets for cholera therapy" Trends Pharmacol. Sci. 26(4): 172-175, 2005.

Tomalia et al., "A New Class of Polymers: Starburst-Dendritic Macromolecules" Polymer Journal 17(1): 117-132, 1985.

Verkman et al., "CFTR Chloride Channel Drug Discovery—Inhibitors as Antidiarrheals and Activators for Therapy of Cystic Fibrosis" Curr. Pharm. Des. 12(18): 2235-2247, 2006.

Verma et al., "Synthesis and Anti-inflammatory Activities of Substituted Arylamino-N'-benzylidene) acetohydrazides and Derivatives" Arch. Pharm. (Weinheim) 317: 890-894, 1984.

Wong, "CFTR gene and male fertility" Molecular Human Reproduction 4(2): 107-110, 1998.

Yang et al., "Small-Molecule CFTR Inhibitors Slow Cyst Growth in Polycystic Kidney Disease" J. Am. Soc. Nephrol. 19(7): 1300-1310, 2008.

Yang et al., "Nanomolar Affinity Small Molecule Correctors of Defective ΔF508-CFTR Chloride Channel Gating" The Journal of Biological Chemistry 278(37): 35079-35085, 2003.

Zegarra-Moran et al., "Correction of G551D-CFTR transport defect in epithelial monolayers by genistein but not by CPX or MPB-07" Br. J. Pharmacol. 137: 504-512, 2002.

Zhou et al., "Probing an Open CFTR Pore with Organic Anion Blockers" J. Gen. Physiol. 120: 647-662, 2002.

\* cited by examiner

MACROMOLECULAR CONJUGATES OF CYSTIC FIBROSIS TRANSMEMBRANE CONDUCTANCE REGULATOR PROTEIN INHIBITORS AND USES THEREFOR

CROSS-REFERENCE TO RELATED APPLICATION

This application claims the benefit of U.S. Provisional Application No. 60/876,616 filed Dec. 22, 2006, which is herein incorporated by reference in its entirety.

STATEMENT OF GOVERNMENT INTEREST

This invention was made with government support under Grant No. P30 DK72517 and R01 HL73856 awarded by the National Institutes of Health. The government has certain rights in this invention.

BACKGROUND

1. Field

Agents are needed for treating diseases and disorders related to aberrant cystic fibrosis transmembrane conductance regulator protein (CFTR) such as increased intestinal fluid secretion, secretory diarrhea, and polycystic kidney disease. Small molecule conjugates are described herein that are potent inhibitors of CFTR activity and that may be used for treating such diseases and disorders.

2. Description of the Related Art

Diarrheal disease in children is a global health concern: approximately four billion cases among children occur annually, resulting in two million deaths. Travelers' diarrhea affects approximately 6 million people per year. Antibiotics are routinely used to treat diarrhea; however, the antibiotics are ineffective for treating many pathogens, and the use of these drugs contributes to development of antibiotic resistance in other pathogens.

The cystic fibrosis transmembrane conductance regulator protein (CFTR) is a cAMP-activated chloride ($Cl^-$) channel expressed in epithelial cells in mammalian airways, intestine, pancreas, and testis. Certain mutations in CFTR lead to the hereditary disease cystic fibrosis (see, e.g., Quinton, *Physiol. Rev.* 79:S3-S22 (1999); Boucher, *Eur. Respir. J.* 23:146-58 (2004)). CFTR is expressed in enterocytes in the intestine and in cyst epithelium in polycystic kidney disease (see, e.g., O'Sullivan et al., *Am. J. Kidney Dis.* 32:976-983 (1998); Sullivan et al., *Physiol. Rev.* 78:1165-91 (1998); Strong et al., *J. Clin. Invest.* 93:347-54 (1994); Mall et al., *Gastroenterology* 126:32-41 (2004); Hanaoka et al., *Am. J. Physiol.* 270: C389-C399 (1996); Kunzelmann et al., *Physiol. Rev.* 82:245-289 (2002); Davidow et al., *Kidney Int.* 50:208-18 (1996); Li et al., *Kidney Int.* 66:1926-38 (2004); Al-Awqati, *J. Clin. Invest.* 110:1599-1601 (2002); Thiagarajah et al., *Curr. Opin. Pharmacol.* 3:594-99 (2003)). Hormones, toxins, such as cholera toxin, and increased cellular $Ca^{2+}$ lead to an increase in cAMP activation of cAMP-dependent protein kinase, which phosphorylates the CFTR $Cl^-$ channel.

CFTR provides a pathway for the movement of $Cl^-$ ions across the apical membrane and thus regulates the rate of transepithelial salt and water transport. CFTR mediates transepithelial fluid secretion in secretory diarrhea; therefore, inhibitors of CFTR function may be useful therapeutics for treating this disease. The morbidity and mortality associated with secretory diarrhea indicate an imperative need for potent inhibitors of CFTR activity.

BRIEF SUMMARY

Briefly stated, provided herein are bioactive agents, compositions, and methods that are useful for treating diseases and disorders related to or associated with aberrantly increased CFTR transporter activity. The methods include administration to a subject as provided herein, such as a human or other warm-blooded animal in need thereof, an effective amount of at least one bioactive agent described herein. In one embodiment, the bioactive agent has the following formula I: $[(A)-(J_{n'})]_n-M$, wherein n=1 to 500 and n'=0 or 1; A is a compound that inhibits activity of the cystic fibrosis transmembrane conductance regulator protein (CFTR); J is a spacer; and M is a macromolecular moiety capable of interacting with a cell that expresses CFTR.

In a more specific embodiment, the compound A has a structure of formula A1, or a pharmaceutically acceptable salt or stereoisomer thereof, such that the bioactive agent has the formula I(a): $[(A)-(J_{n'})]_n-M$ as follows:

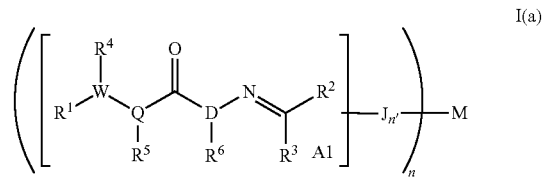

I(a)

wherein W is C, N, O, S, or absent;
Q is C or absent;
D is C, N or absent;
$R^1$ is phenyl, heteroaryl, quinolinyl, anthracenyl, or naphthalenyl, or $R^1$ is H or $C_{1-5}$ alkyl and $R^1$, W, and Q join together to form a 5- to 7-membered homocyclic or heterocyclic ring;
$R^2$ is phenyl, optionally substituted with any one or more of hydroxyl, $C_{1-8}$ alkyl, $C_{1-18}$ alkoxy, carboxy, halo, nitro, cyano, $-SO_3H$, $-S(=O)_2NH_2$, aryl, and heteroaryl;
$R^3$ is H, $C_{1-8}$ alkyl, or phenyl;
$R^4$ is H, $C_{1-8}$ alkyl, phenyl, $-CH_2(CH)_x-C(=O)OH$, $-CH_2(CH)_x-NR^7R^8-Z$, $-NR^7NR^8-Z$, or $-CH_2(CH)_x-O-(CH)_yCH_2Z$, wherein x=0-7, y=0-7, and Z is a disaccharide or a synthetic polymer selected from polyoxyalkyl polyether, polyethylene glycol (PEG), polypropylene glycol, polyhydroxyethyl glycerol, a dendrimer, and polyalkylimine;
$R^5$ is H, alkyl, oxo, phenyl, carboxy, aryl, heterocycle, $-C(=O)NHNR^9R^{10}$, $-C(=O)NHN(=R^9)$, $-NR^9R^{10}$; $-C(=O)NHNHC(=S)NR^9R^{10}$, $-C(=O)NHNHC(=O)NR^9R^{11}$, $-C(=O)NHNHC(=O)CR^9R^{10}$, $-C(=O)R^9$, $-CH_2(CH)_zR^9$ wherein z is 0-7, $-(CH_2CH_2O)_pR^9$ wherein p is 0-500, or $-CH_2CH_2NHR^{11}$;
$R^6$ is H, $C_{1-18}$ alkyl; or aryl;
each of $R^7$, $R^8$, $R^9$, and $R^{10}$ is the same or different and independently H, $C_{1-8}$ alkyl, cycloalkyl, phenyl, or phenylalkyl;
$R^{11}$ is H, $C_{1-8}$ alkyl, cycloalkyl, phenyl, alkylphenyl, or a synthetic polymer selected from polyoxyalkyl polyether, polyethylene glycol (PEG), polypropylene glycol, polyhydroxyethyl glycerol, a dendrimer, and polyalkylimine;
wherein J is a spacer that comprises a first end and a second end, wherein the spacer is attached to the compound of formula A1 at the first end of the spacer through a first linker functional group and wherein the spacer is attached to the macromolecular moiety M at the second end of the spacer through a second linker functional group, and wherein the first end of the spacer is attached to compound A1 at one or more of $R^1$, $R^2$, $R^3$, $R^4$ or $R^5$;

and wherein when n'=0, M forms a direct bond with at least one of $R^1$, $R^2$, $R^3$, $R^4$ or $R^5$.

Additional embodiments of bioactive agents having a structure of the formulae I(b)-I(h) are described in detail herein. Also provided herein is a method of treating a disease or disorder associated with aberrantly increased ion transport by cystic fibrosis transmembrane conductance regulator (CFTR), the method comprising administering to a subject the bioactive agent as described above, and in further detail herein, any one of the bioactive agents having a structure of any one of the formula I and subformulae I(a)-I(h), wherein ion transport by CFTR is inhibited. In a particular embodiment, the disease or disorder is secretory diarrhea.

Also provided herein are compositions that comprise at least one of the bioactive agents having a structure of any one of formula I or subformulae I(a)-I(h) as described above and herein, and a pharmaceutically acceptable excipient.

In another embodiment, a method is provided for treating a disease or disorder associated with aberrantly increased ion transport by cystic fibrosis transmembrane conductance regulator (CFTR), the method comprising administering to a subject any of the aforementioned compositions comprising at least one bioactive agent having a structure of any one of formula I or subformulae I(a)-I(h) as described above and herein, and a pharmaceutically acceptable excipient, wherein ion transport by CFTR is inhibited. In one embodiment, the disease or disorder is aberrantly increased intestinal fluid secretion. In another embodiment, the disease or disorder is secretory diarrhea. In certain specific embodiments, secretory diarrhea is caused by an enteric pathogen. In particular embodiments, the enteric pathogen is *Vibrio cholerae, Clostridium difficile, Escherichia coli, Shigella, Salmonella*, rotavirus, *Giardia lamblia, Entamoeba histolytica, Campylobacter jejuni*, and *Cryptosporidium*. In still another embodiment, the secretory diarrhea is induced by an enterotoxin. In a specific embodiment, the enterotoxin is a cholera toxin, a *E. coli* toxin, a *Salmonella* toxin, a *Campylobacter Salmonella* toxin, or a *Shigella* toxin. In another particular embodiment, secretory diarrhea is a sequelae of ulcerative colitis, irritable bowel syndrome (IBS), AIDS, chemotherapy, or an enteropathogenic infection. In certain embodiments, the subject is a human or non-human animal. In a more specific embodiment, method of treating secretory diarrhea comprising administering to a subject a pharmaceutically acceptable excipient and at least one bioactive agent having a structure of any one of formula I or subformulae I(a)-I(h) as described above and herein. In certain embodiments, the subject is a human or non-human animal.

In another embodiment, a method is provided for inhibiting ion transport by a cystic fibrosis transmembrane conductance regulator (CFTR) comprising contacting (a) a cell that comprises CFTR and (b) the bioactive agent having a structure of any one of formula I or subformulae I(a)-I(h) as described above and herein, under conditions and for a time sufficient for the CFTR and the compound to interact, thereby inhibiting ion transport by CFTR.

As used herein and in the appended claims, the singular forms "a," "and," and "the" include plural referents unless the context clearly dictates otherwise. Thus, for example, reference to "an agent" includes a plurality of such agents, and reference to "a cell" or "the cell" includes reference to one or more cells and equivalents thereof (e.g., plurality of cells) known to those skilled in the art, and so forth. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

BRIEF DESCRIPTION OF THE DRAWINGS

FIG. 2A illustrates the effect of unconjugated ConA on inhibition potency of MalH-ConA. The left panel shows inhibition of short circuit current by MalH-ConA after CFTR stimulation, in absence or presence of 5 μM ConA. The right panel presents concentration-inhibition data for MalH-DIDS in the presence (filled triangle) and absence (open triangle) of 5 μM ConA. Data are also shown for MalH-ConA in the absence (filled circles) and presence (open circles) of 5 μM ConA. FIG. 2B shows inhibition of chloride current by MalH-ConA in the presence of 20 or 200 mM mannose (left panel). The right panel shows concentration-inhibition data for MalH-ConA in presence of mannose (200 mM, open circles) and for MalH-DIDS (with and without 200 mM mannose, closed and open triangles, respectively).

FIG. 3A presents apical membrane chloride current measurements for MalH-ConA that was denatured by acidification (incubation at pH 5.2 or 1.5, top), denatured by heating (incubation at 100° C. for 5 min, middle), or enzymatically digested (incubation with pronase at 37° C. for 8 h, bottom) prior to current measurements. Also shown is the effect of inclusion of EDTA in the buffer at the time of current measurements (bottom). FIG. 3B presents concentration inhibition data. Concentration-inhibition data for MalH-ConA at pH 5.2 (open circles) and 1.5 (open triangles), and for MalH-DIDS (closed triangles, pH 1.5) is shown in the top graph. Data for heat-treated MalH-DIDS (closed triangles) and MalH-ConA (open circles) is presented in the middle graph. Data for MalH-ConA in the presence of EDTA (open triangles), and after pronase digestion (open circles), and MalH-DIDS after treatment with pronase (closed triangles) is presented in the bottom graph. Each data point is the mean ±SE for measurements on 3-8 cell culture samples.

FIG. 4A shows representative whole-cell membrane currents (Im) from a CFTR-expressing FRT cell. Each panel shows superimposed membrane currents induced at different membrane potentials (from −100 to +100 mV) in 20 mV steps. Currents were recorded under resting conditions (top), after CFTR activation with 20 μM forskolin (middle), and following addition of 250 nM MalH-ConA (bottom). The inset panel presents kinetics of block by MalH-ConA (250 nM) compared with GlyH-101 (5 μM) after stepping the membrane potential to +80 mV. FIG. 4B presents the current-voltage relationships from experiments presented in FIG. 4A. FIG. 4C presents outside-out patch recording that shows block of CFTR single channel currents by 100 nM MalH-ConA. Membrane potential was +80 mV. CFTR was activated by protein kinase A/ATP.

FIG. 5A illustrates apical membrane current that was measured before and after washout of MalH-DIDS (left) and MalH-ConA (right). FIG. 5B demonstrates washout of fluorescently labeled MalH-ConA. Cells were incubated with MalH-TMR-ConA at 4° C. for 3 min and washed with PBS for 5 min (upper left) or 30 min (upper right), or with 200 mM mannose (lower left). 'Excess ConA' indicates cells that were preincubated with ConA prior to labeling. FIG. 5C presents the relative cell-associated TMR fluorescence measured at the indicated times after washout by PBS or mannose (20 mM), and presents the TMR fluorescence measured in cells that were pre-incubated with ConA or mannose (standard error: 4 cell culture samples per condition, * P<0.05). FIG. 5D demonstrates inhibitor washout in a suckling mouse model of cholera. Suckling mice were gavaged with control vehicle (from the left, the first mouse), or with equi-fluorescent TMR-MalH-ConA (second and third mice) or TMR-dextran (fourth and fifth mice). Whole body fluorescence images were collected at indicated times. The photographs present typical results for each of 6 mice studied per group.

FIG. 6A illustrates inhibition by MalH-ConA and MalH-wheat of short-circuit current in non-permeabilized T84 cells after CFTR stimulation. Amiloride and forskolin were added as indicated. FIG. 6B presents data showing the intestinal fluid accumulation at 6 h in closed mid-jejunal loops in mice (standard error: 6-8 loops included per condition; * P<0.05, ANOVA). FIG. 6C illustrates that survival of suckling mice (30 mice per group) following gavage with cholera toxin with or without MalH-ConA (125 pmol) (top) (P=0.0015, log-rank test) and MalH-wheat (200 pmol) (bottom) (P=0.0012, log-rank test). Vehicle control refers to identically processed mice that did not receive cholera toxin or MalH-lectins.

FIG. 7A (left and right panels) represents duplicate measurements using the compound conjugated to concanavalin A. FIG. 7B (left and right panels) represents duplicate measurements using the compound conjugated to wheat germ lectin. FIG. 7C presents data obtained using the compound conjugated to tomato lectin, and FIG. 7D presents data for the compound attached to the linker DIDS.

DETAILED DESCRIPTION

Figure 1:
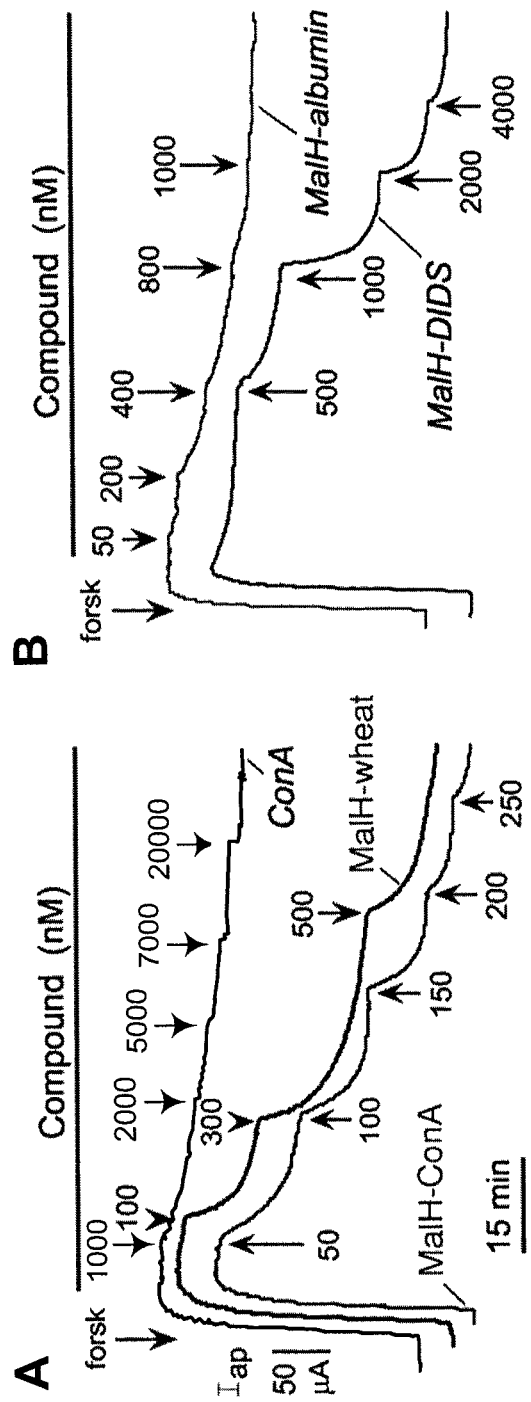
FIGS. 1A-1B illustrate inhibition of apical membrane chloride current in FRT epithelial cells expressing human wildtype CFTR. CFTR was stimulated by 20 μM forskolin (forsk). Increasing concentrations of MalH-ConA, MalH-wheat, and ConA (FIG. 1A), and MalH-DIDS and MalH-albumin (FIG. 1B) were added as indicated.
Figure 2:
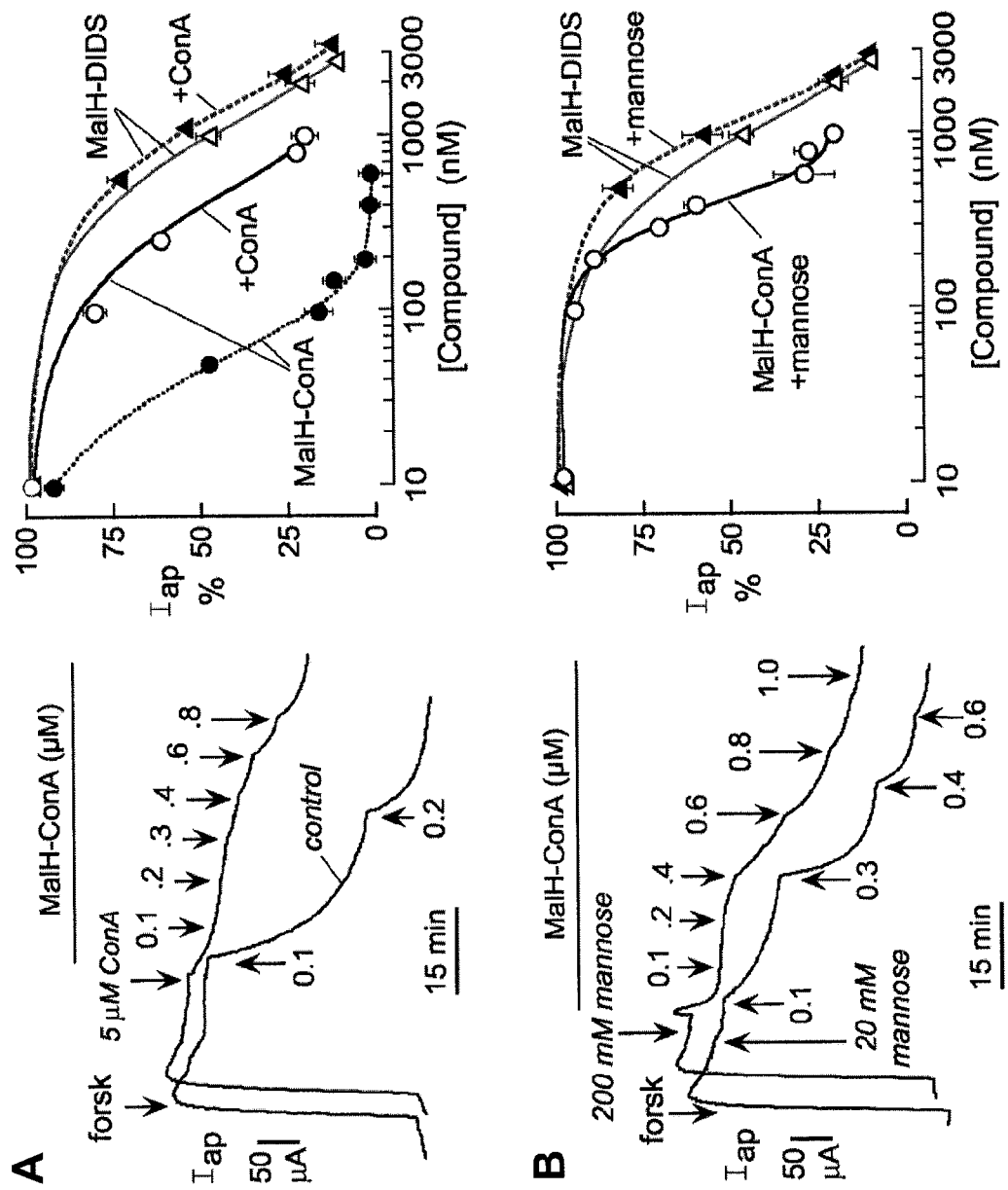
FIGS. 2A-2B presents data illustrating inhibition of short circuit current by MalH-ConA.
Figure 3:
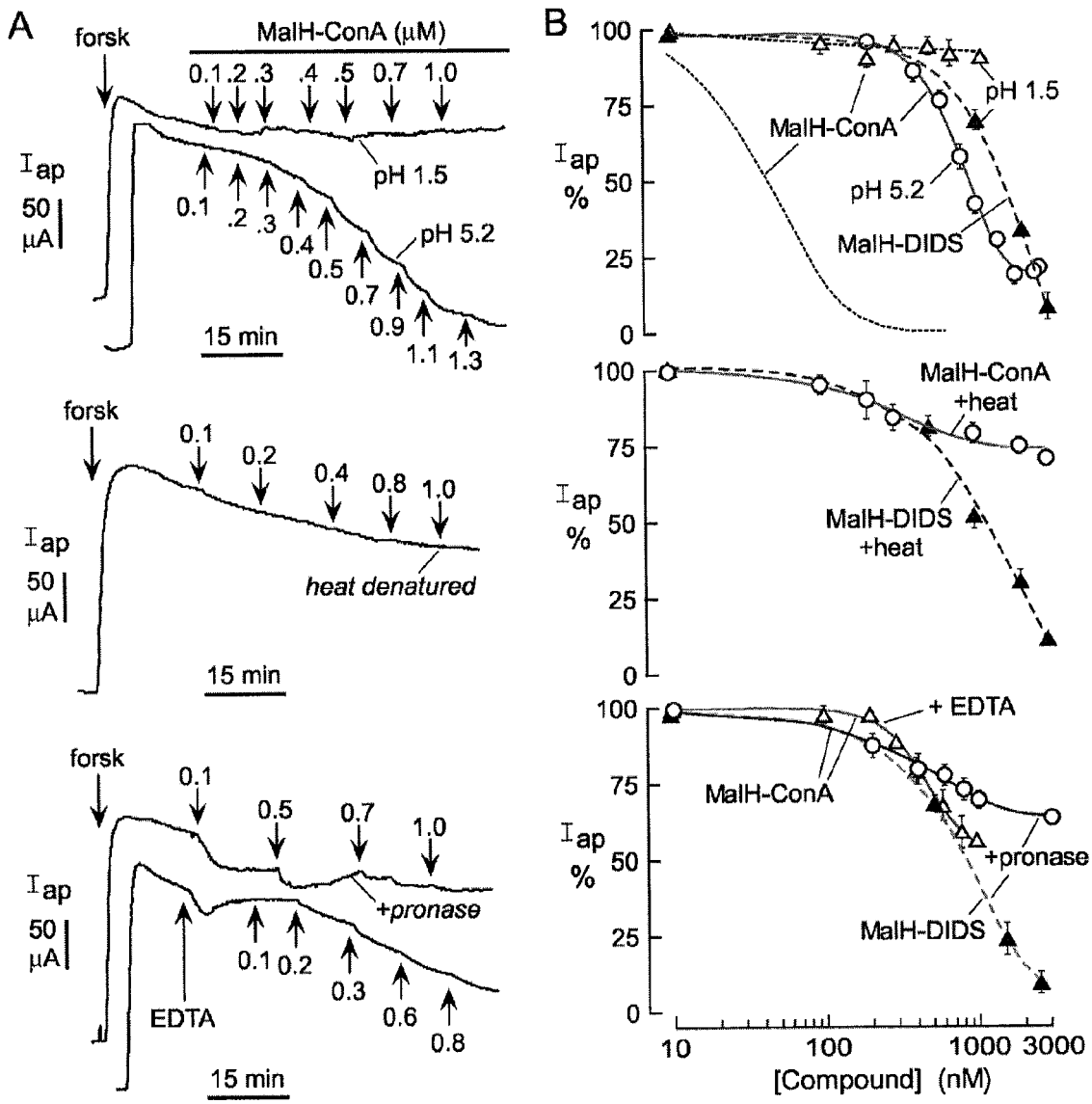
FIGS. 3A-3B illustrate that denaturation of MalH-lectin reduced CFTR-inhibition potency.

Specific inhibitors of CFTR activity useful for altering intestinal fluid secretion include the non-absorbable glycine hydrazide compounds and malonic hydrazide compounds (see, e.g., Muanprasat et al., *J. Gen. Physiol.* 124:125-37 (2004); Sonawane et al., *FASEB J.* 20:130-32 (2006)). Effective glycine hydrazide and malonic hydrazide inhibitors had an $IC_{50}$ of approximately 5 µM. Binding of compounds with micromolar $IC_{50}$ to CFTR expressed in intestinal lumen may be readily reversed, particularly by washout of the compound from the intestine by rapid intestinal fluid transit in a subject affected with secretory diarrhea. The disclosure herein relates to the discovery of significantly improved bioactive agents that are inhibitors of CFTR activity and which include hydrazide compound conjugates that are minimally absorbable by cells and thus minimize potential cellular and systemic toxicity.

The bioactive agents described herein may therefore be used for treating diseases and disorders associated with aberrantly increased CFTR-mediated transepithelial fluid secretion. Such diseases and disorders include secretory diarrhea, which may be caused by enteropathogenic organisms including bacteria, viruses, and parasites, such as but not limited to *Vibrio cholerae, Clostridium difficile, Escherichia coli, Shigella, Salmonella*, rotavirus, *Campylobacter jejuni, Giardia lamblia, Entamoeba histolytica, Cyclospora*, and *Cryptosporidium* or by toxins such as cholera toxin and *Shigella* toxin. The bioactive agents described herein may also be useful for treating secretory diarrhea that is a sequelae of a disease, disorder, or condition, including but not limited to AIDS, administration of AIDS related therapies, chemotherapy, and inflammatory gastrointestinal disorders such as ulcerative colitis, inflammatory bowel disease (IBD), and Crohn's disease.

Small molecule inhibitors of the cystic fibrosis transmembrane conductance regulator protein (CFTR), which is a cAMP-activated chloride ($Cl^-$) channel, include thiazolidinone compounds (see, e.g., U.S. Patent Application Publication No. 2004/0235800) and glycine hydrazide, oxamic hydrazide, and malonic hydrazide compounds (see, e.g., U.S. Patent Application Publication No. 2005/0239740; see also, e.g., Salinas et al., *FASEB J.* 19:431-33 (2005); Thiagarajah et al., *FASEB J.* 18:875-77 (2004)). Any one of these compounds may be conjugated to (i.e., linked, attached, joined, covalently bonded to) a macromolecule that is capable of binding to (i.e., associating by ionic interaction (coulombic forces), hydrophobic, hydrophilic, lipophilic interaction, hydrogen bonding, or any combination thereof, to) a cell that expresses CFTR. Without wishing to be bound by theory, these minimally absorbable macromolecular conjugates may have increased potency compared with a non-conjugated compound, in part, because the conjugated compounds are not washed away from the intestinal lumen.

The hydrazide compounds, including malonic hydrazide compounds, described herein are conjugated to macromolecules (e.g., lectins, synthetic polymers, and other cell-binding moieties) and have submicromolar potency. These compounds may therefore be used for treating diseases and disorders associated with aberrantly increased CFTR-mediated transepithelial fluid secretion, such as secretory diarrhea.

Hydrazide Compounds Conjugated to a Macromolecule

A bioactive agent described herein has the following formula I: $[(A-J_{n'})]_n-M$, wherein n=1 to 500 and n'=0 to 1; A is a compound that inhibits activity of the cystic fibrosis transmembrane conductance regulator protein (CFTR); J is a spacer; and M is a cell-binding macromolecular moiety capable of binding to, associating with, or in some manner interacting with a cell that expresses CFTR. Cell binding moieties, which are described in greater detail herein, include but are not limited to, a lectin, a lectin-mimetic, a cell receptor ligand, polylysine, a saccharide (e.g., a disaccharide or a polysaccharide), a synthetic polymer, an antibody that specifically binds to a cell surface receptor; an antibody that specifically binds to the extracellular domain of a cell transmembrane polypeptide, and a peptide.

In one embodiment, the compound A moiety of the agent of formula I is a glycine hydrazide, oxamic hydrazide, acetic acid hydrazide, or a malonic hydrazide (MalH) conjugated (i.e., linked, attached, and preferably covalently bonded) to a cell binding moiety M via a spacer J. These bioactive agents are highly water soluble, bind to an external surface of the CFTR pore, and exhibit minimal systemic absorption into cells (i.e., a minimum amount of a compound is transported into a cell).

In one embodiment, the bioactive agent has the following formula I: $[(A)-(J)_{n'}]_n-M$, wherein n=1 to 500 and n'=0 or 1; A is a compound that inhibits activity of the cystic fibrosis transmembrane conductance regulator protein (CFTR); J is a spacer; and M is a macromolecular moiety capable of interacting with a cell that expresses CFTR (i.e., a cell-binding moiety). In certain specific embodiments, n=1 to 10, 1 to 15, 1 to 20, 1 to 25, 1 to 50, 1 to 100, 1 to 200, 1 to 250, 1 to 300, or 1 to 400 or any integer between any of the aforementioned ranges.

In a more specific embodiment, the compound A has a structure of formula A1, or a pharmaceutically acceptable salt or stereoisomer thereof, such that the bioactive agent has the formula I(a): $[(A1)-(J)_{n'}]_n-M$ as follows:

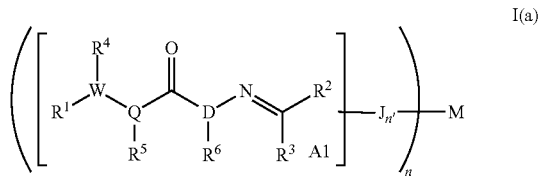

wherein W is C, N, O, S, or absent;

Q is C or absent;

D is C, N or absent;

$R^1$ is phenyl, heteroaryl, quinolinyl, anthracenyl, or naphthalenyl, or $R^1$ is H or $C_{1-5}$ alkyl and $R^1$, W, and Q join together to form a 5- to 7-membered homocyclic or heterocyclic ring;

$R^2$ is phenyl, optionally substituted with any one or more of hydroxyl, $C_{1-8}$ alkyl, $C_{1-18}$ alkoxy, carboxy, halo, nitro, cyano, —$SO_3H$, —$S(=O)_2NH_2$, aryl, and heteroaryl;

$R^3$ is H, $C_{1-8}$ alkyl, or phenyl;

$R^4$ is H, $C_{1-8}$ alkyl, phenyl, —$CH_2(CH)_x$—$C(=O)OH_x$— $CH_2(CH)_x$—$NR^7R^8$-Z, —$NR^7NR^8$-Z, or —$CH_2(CH)_x$— O—$(CH)_yCH_2Z$, wherein x=0-7, y=0-7, and Z is a disaccharide or a synthetic polymer selected from polyoxyalkyl polyether, polyethylene glycol (PEG), polypropylene glycol, polyhydroxyethyl glycerol, a dendrimer, and polyalkylimine;

$R^5$ is H, alkyl, oxo, phenyl, carboxy, aryl, heteroaryl, —$C(=O)NHNR^9R^{10}$, —$C(=O)NHN(=R^9)$, —$NR^9R^{10}$; —$C(=O)NHNHC(=S)NR^9R^{10}$, —$C(=O)NHNHC(=O)$ $NR^9R^{11}$, —$C(=O)NHNHC(=O)CR^9R^{10}$, —$C(=O)R^9$, —$CH_2(CH)_zR^9$ wherein z is 0-7, —$(CH_2CH_2O)_pR^9$ wherein p is 0-500, or —$CH_2CH_2NHR^{11}$;

$R^6$ is H, $C_{1-18}$ alkyl; or aryl;

each of $R^7$, $R^8$, $R^9$, and $R^{10}$ is the same or different and independently H, $C_{1-8}$ alkyl, cycloalkyl, phenyl, or phenylalkyl;

$R^{11}$ is H, $C_{1-8}$ alkyl, cycloalkyl, phenyl, alkylphenyl, or a synthetic polymer selected from polyoxyalkyl polyether, polyethylene glycol (PEG), polypropylene glycol, polyhydroxyethyl glycerol, a dendrimer, and polyalkylimine;

wherein J is a spacer that comprises a first end and a second end, wherein the spacer is attached to the compound of formula A1 at the first end of the spacer through a first linker functional group and wherein the spacer is attached to the macromolecular moiety M at the second end of the spacer through a second linker functional group, and wherein the first end of the spacer is attached to compound A1 at one or more of $R^1$, $R^2$, $R^3$, $R^4$ or $R^5$;

and wherein when n'=0, M forms a direct bond with at least one of $R^1$, $R^2$, $R^3$, $R^4$ or $R^5$.

In certain embodiments, $R^2$ is substituted phenyl, wherein the phenyl is substituted with one, two, or three halo; one or two carboxy; one, two, or three hydroxyl; one or two halo and one, two, or three hydroxyl; one or two halo, one or two hydroxyl, and one $C_{1-8}$ alkoxy; one or two halo, one hydroxyl, and one or two $C_{1-8}$ alkoxy; or one halo, one or two hydroxyl, and one or two $C_{1-8}$ alkoxy, wherein halo is bromo, chloro, fluoro, or iodo. In other certain specific embodiments, $R^2$ is substituted phenyl, wherein phenyl is substituted with halogen or carboxy. In yet other specific embodiments, $R^2$ is di(hydroxyl)phenyl; mono-(halo)-mono-(hydroxyl)phenyl; mono-(halo)-di-(hydroxyl)phenyl; mono-(halo)-tri-(hydroxyl)phenyl; di(halo)-mono-(hydroxyl)phenyl; di(halo)-di-(hydroxyl)phenyl; di(halo)-tri-(hydroxyl)phenyl; or mono- or di-(halo)-mono- or di-(hydroxy)-mono- or di-(alkoxy)phenyl (i.e., mono-(halo)-mono-(hydroxy)-mono-(alkoxy)phenyl; mono-(halo)-di-(hydroxy)-mono-(alkoxy) phenyl; mono-(halo)-mono-(hydroxy)-di-(alkoxy)phenyl; mono-(halo)-di-(hydroxy)-di-(alkoxy)phenyl; di-(halo)-mono-(hydroxy)-mono-(alkoxy)phenyl; di-(halo)-di-(hydroxy)-mono-(alkoxy)phenyl; or di-(halo)-mono-(hydroxy)-di-(alkoxy)phenyl). In certain specific embodiments, $R^2$ is 2-, 3-, or 4-halophenyl; 3,5-dihalophenyl; 2-, 3-, or 4-hydroxyphenyl; 2,4-dihydroxyphenyl; 3,5-dihalo-2,4,6-trihydroxyphenyl, 3,5-dihalo-2,4-dihydroxyphenyl; 3,5-dihalo-4-hydroxyphenyl; 3-halo-4-hydroxyphenyl; 3,5-dihalo-2-hydroxy-4-methoxyphenyl; or 4-carboxyphenyl, wherein halo is bromo, chloro, fluoro, or iodo. In a more specific embodiment, the halo is bromo. In particular specific embodiments, $R^2$ is 3,5-dibromo-2,4-dihydroxyphenyl; 3,5-dibromo-4-hydroxyphenyl; 2,4-dihydroxyphenyl; 4-bromophenyl; 4-carboxyphenyl; and 3,5-dibromo-2-hydroxy-4-methoxyphenyl.

In other specific embodiments of the bioactive agent formula I(a), $R^4$ is $C_{1-8}$ alkyl that is optionally substituted with —$C(=O)OH$, —$C(=O)OR_a$, —$SH$; —$SR_a$, —$SOR_a$, —$S(=O)_2NR_aR_b$, —$S(=O)_2R_a$, —$SR_aC(=O)NR_aR_b$, —$OS(=O)_2R_a$, —$NR_aR_b$, or —$S(=O)_2OR_a$ wherein $R_a$ and $R_b$ are the same or different and independently hydrogen, alkyl, haloalkyl, substituted alkyl, alkoxy, aryl, substituted aryl, arylalkyl, substituted arylalkyl, aryloxy, arylalkoxy, heteroaryl, substituted heteroaryl, heteroarylalkyl, substituted heteroarylalkyl, heterocycle, substituted heterocycle, heterocycloalkyl or substituted heterocyclealkyl.

In yet other specific embodiments of the bioactive agent formula I(a), $R^1$ is unsubstituted phenyl, or substituted phenyl wherein phenyl is substituted with one or more of hydroxy, $C_{1-8}$ alkyl, halo, aryl, or aryloxy. Halo is chloro, fluoro, iodo, and in certain specific embodiments, halo is chloro. In another specific embodiment, $R^1$ is substituted phenyl wherein phenyl is substituted with methyl. In yet another specific embodiment, $R^1$ is quinolinyl or anthracenyl, optionally substituted with one or more of halo, hydroxyl, $C_{1-8}$ alkyl, or $C_{1-8}$ alkoxy. In other embodiments, $R^1$ is 2-naphthalenyl or 1-naphthalenyl, optionally substituted with one or more of halo, hydroxyl, —SH, —$SO_3H$, $C_{1-8}$ alkyl, $C_{1-8}$ alkoxy, aryl, or aryloxy. In more specific embodiments, $R^1$ is mono-(halo)naphthalenyl; di-(halo)naphthalenyl; tri-(halo) naphthalenyl; mono-(hydroxy)naphthalenyl; di-(hydroxy) naphthalenyl; tri-(hydroxy)naphthalenyl; mono-(alkoxy) naphthalenyl; di-(alkoxy)naphthalenyl; tri-(alkoxy) naphthalenyl; mono-(aryloxy)naphthalenyl; di-(aryloxy) naphthalenyl; mono-(alkyl)naphthalenyl; di-(alkyl) naphthalenyl; tri-(alkyl)naphthalenyl; mono-(hydroxy)-naphthalene-sulfonic acid; mono-(hydroxy)-naphthalenedisulfonic acid; mono or di(halo)-mono or di(hydroxy)naphthalenyl; mono-(alkyl)-mono-(alkoxy)-naphthalenyl; or mono-(alkyl)-di-(alkoxy)-naphthalenyl. In still more specific embodiments, $R^1$ is 2-chlorophenyl, 4-chlorophenyl, 2,4-dichlorophenyl, 4-methylphenyl, 2-anthracenyl, or 6-quinolinyl. In other particular embodiments, $R^1$ is quinolinyl or anthracenyl, optionally substituted with one or more of halo, hydroxyl, $C_{1-8}$ alkyl, or $C_{1-8}$ alkoxy.

In other specific embodiments of the bioactive agent formula I(a), each of $R^3$ and $R^5$ is the same or different and independently hydrogen, oxo, methyl, or ethyl. In another specific embodiment, $R^5$ is oxo. In a particular embodiment, $R^4$ is hydrogen; $R^5$ is hydrogen, methyl, or ethyl; $R^1$ is mono-(halo)phenyl, di-(halo)phenyl, or naphthalenyl; $R^2$ is di-(halo)-mono(hydroxyl)phenyl or di-(halo)-di(hydroxyl)phenyl; and $R^3$ is hydrogen or methyl.

In certain specific embodiments, n=1 to 10, 1 to 15, 1 to 20, 1 to 25, 1 to 50, 1 to 100, 1 to 200, 1 to 250, 1 to 300, or 1 to 400 or any integer between any of the aforementioned ranges.

In another embodiment, of the bioactive agent described above, each of W and D is N, Q is C, and each of $R^4$ and $R^6$ is H, and the compound A has a structure of formula A2, or a pharmaceutically acceptable salt or stereoisomer thereof, such that the bioactive agent has the formula I(b): [A2–$(J_{n'})]_n$–M as follows:

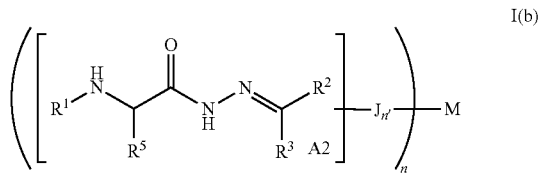

wherein $R^1$ is phenyl, heteroaryl, quinolinyl, anthracenyl, or naphthalenyl. In certain embodiments, each of $R^2$, $R^3$, and $R^5$ are as defined for a compound of formula A1. In certain other embodiments, $R^2$ is substituted phenyl, and wherein the phenyl is substituted with one, two, or three halo; one or two carboxy; one, two, or three hydroxyl; one or two halo and one, two, or three hydroxyl; one or two halo, one or two hydroxyl, and one $C_{1-8}$ alkyl; one or two halo, one hydroxyl, and one or two $C_{1-8}$ alkoxy; or one halo, one or two hydroxyl, and one or two $C_{1-8}$ alkoxy, wherein halo is bromo, chloro, fluoro, or iodo. In yet other specific embodiments, $R^2$ is di(hydroxyl)phenyl; mono-(halo)-mono-(hydroxyl)phenyl; mono-(halo)-di-(hydroxyl)phenyl; mono-(halo)-tri-(hydroxyl)phenyl; di(halo)-mono-(hydroxyl)phenyl; di(halo)-di-(hydroxyl)phenyl; di(halo)-tri-(hydroxyl)phenyl; or mono- or di-(halo)-mono- or di-(hydroxy)-mono- or di-(alkoxy)phenyl (i.e., mono-(halo)-mono-(hydroxy)-mono-(alkoxy)phenyl; mono-(halo)-di-(hydroxy)-mono-(alkoxy)phenyl; mono-(halo)-mono-(hydroxy)-di-(alkoxy)phenyl; mono-(halo)-di-(hydroxy)-di-(alkoxy)phenyl; di-(halo)-mono-(hydroxy)-mono-(alkoxy)phenyl; di-(halo)-di-(hydroxy)-mono-(alkoxy)phenyl; or di-(halo)-mono-(hydroxy)-di-(alkoxy)phenyl). In certain specific embodiments, $R^2$ is 2-, 3-, or 4-halophenyl; 3,5-dihalophenyl; 2-, 3-, or 4-hydroxyphenyl; 2,4-dihydroxyphenyl; 3,5-dihalo-2,4,6-trihydroxyphenyl, 3,5-dihalo-2,4-dihydroxyphenyl; 3,5-dihalo-4-hydroxyphenyl; 3-halo-4-hydroxyphenyl; 3,5-dihalo-2-hydroxy-4-methoxyphenyl; or 4-carboxyphenyl, wherein halo is bromo, chloro, fluoro, or iodo. In a more specific embodiment, halo is bromo. In other certain embodiments, $R^2$ is 2-, 3-, or 4-halophenyl; 3,5-dihalophenyl; 2-, 3-, or 4-hydroxyphenyl; 2,4-dihydroxyphenyl; 3,5-dihalo-2,4,6-trihydroxyphenyl, 3,5-dihalo-2,4-dihydroxyphenyl; 3,5-dihalo-4-hydroxyphenyl; 3-halo-4-hydroxyphenyl; 3,5-dihalo-2-hydroxy-4-methoxyphenyl; or 4-carboxyphenyl, wherein halo is fluoro, chloro, bromo, or iodo. In other specific embodiments, halo is bromo.

In other embodiments of a bioactive agent that has the formula I(b), $R^1$ is unsubstituted phenyl, or substituted phenyl wherein phenyl is substituted with one or more of hydroxy, $C_{1-8}$ alkyl, aryl, aryloxy, or halo, wherein halo is fluoro, chloro, bromo, or iodo. In a more specific embodiment, halo is chloro. In another specific embodiment, $R^1$ is substituted phenyl wherein phenyl is substituted with methyl. In still another specific embodiment, $R^1$ is quinolinyl or anthracenyl, optionally substituted with one or more of halo, hydroxyl, $C_{1-8}$ alkyl, or $C_{1-8}$ alkoxy. In certain specific embodiments, $R^1$ is 2-naphthalenyl or 1-naphthalenyl, optionally substituted with one or more of halo, hydroxyl, —SH, —SO$_3$H, $C_{1-8}$ alkyl, aryl, aryloxy, or $C_{1-8}$ alkoxy. In other specific embodiments, $R^1$ is mono-(halo)naphthalenyl; di-(halo)naphthalenyl; tri-(halo)naphthalenyl; mono-(hydroxy)naphthalenyl; di-(hydroxy)naphthalenyl; tri-(hydroxy)naphthalenyl; mono-(alkoxy)naphthalenyl; di-(alkoxy)naphthalenyl; tri-(alkoxy)naphthalenyl; mono-(aryloxy)naphthalenyl; di-(aryloxy)naphthalenyl; mono-(alkyl)naphthalenyl; di-(alkyl)naphthalenyl; tri-(alkyl)naphthalenyl; mono-(hydroxy)-naphthalene-sulfonic acid; mono-(hydroxy)-naphthalenedisulfonic acid; mono or di(halo)-mono or di(hydroxy) naphthalenyl; mono-(alkyl)-mono-(alkoxy)-naphthalenyl; or mono-(alkyl)-di-(alkoxy)-naphthalenyl. In yet another specific embodiment, $R^1$ is 2-chlorophenyl, 4-chlorophenyl, 4-methylphenyl, 2-anthracenyl, or 6-quinolinyl. In other particular embodiments, $R^1$ is quinolinyl or anthracenyl, optionally substituted with one or more of halo, hydroxyl, $C_{1-8}$ alkyl, or $C_{1-8}$ alkoxy.

In other embodiments of a bioactive agent that has the formula I(b), each of $R^3$ and $R^5$ is the same or different and independently hydrogen, oxo, methyl, or ethyl. In another particular embodiment $R^5$ is oxo. In other particular embodiments, $R^3$ is hydrogen, oxo, or methyl. In still another specific embodiment, $R^2$ is 3,5-dibromo-2,4-dihydroxyphenyl or 3,5-dibromo-4-hydroxyphenyl.

In another embodiment, provided herein is a bioactive agent having the following formula I: [(A)–$(J_{n'})]_n$–M, wherein n=1 to 500 and n'=0 or 1; wherein the compound A has a structure of formula A3, or a pharmaceutically acceptable salt or stereoisomer thereof, such that the bioactive agent has the formula I(c): [A3–$(J_{n'})]_n$–M as follows:

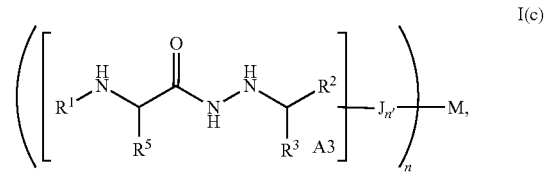

wherein $R^1$ is phenyl, quinolinyl, anthracenyl, or naphthalenyl, or heteroaryl;

$R^2$ is phenyl, optionally substituted with any one or more of hydroxyl, $C_{1-8}$ alkyl, $C_{1-8}$ alkoxy, carboxy, halo, nitro, cyano, —SO$_3$H, —S(═O)$_2$NH$_2$, aryl, and heteroaryl;

$R_3$ is H, oxo, $C_{1-8}$ alkyl, phenyl;

$R^5$ is H, alkyl, oxo, phenyl, heterocycle, aryl, carboxy, —C(═O)NHNR$^9$R$^{10}$, —C(═O)NHN(═R$^9$), —NR$^9$R$^{10}$; —C(═O)NHNHC(═S)NR$^9$R$^{10}$, —C(═O)NHNHC(═O) NR$^9$R$^{11}$, —C(═O)NHNHC(═O)CR$^9$R$^{10}$, —C(═O)R$^9$, —CH$_2$(CH)$_z$R$^9$ wherein z is 0-7, —(CH$_2$CH$_2$O)$_p$R$^9$ wherein p is 0-500, or —CH$_2$CH$_2$NHR$^{11}$;

each of R$^9$ and R$^{10}$ is the same or different and independently H, C$_{1-8}$ alkyl, cycloalkyl, phenyl, or phenylalkyl;

R$^{11}$ is H, C$_{1-8}$ alkyl, cycloalkyl, phenyl, alkylphenyl, or a synthetic polymer selected from polyoxyalkyl polyether, polyethylene glycol (PEG), polypropylene glycol, polyhydroxyethyl glycerol, a dendrimer, and polyalkylimine;

wherein J is a spacer that comprises a first end and a second end, wherein the spacer is attached to the compound of formula A3 at the first end of the spacer through a first linker functional group and wherein the spacer is attached to the macromolecular moiety M at the second end of the spacer through a second linker functional group, and wherein the first end of the spacer is attached to compound A3 at one or more of R$^1$, R$^2$, R$^3$, or R$^5$; and wherein when n'=0, M forms a direct bond with at least one of R$^1$, R$^2$, R$^3$, or R$^5$.

In a particular embodiment of the bioactive agent of formula I(c), R$^3$ is oxo. In another particular embodiment, R$^2$ is substituted phenyl, and wherein the phenyl is substituted with one, two, or three halo; one or two carboxy; one, two, or three hydroxyl; one or two halo and one, two, or three hydroxyl; one or two halo, one or two hydroxyl, and one C$_{1-8}$ alkoxy; one or two halo, one hydroxyl, and one or two C$_{1-8}$ alkoxy; or one halo, one or two hydroxyl, and one or two C$_{1-8}$ alkoxy. In yet other specific embodiments, R$^2$ is di(hydroxyl)phenyl; mono-(halo)-mono-(hydroxyl)phenyl; mono-(halo)-di-(hydroxyl)phenyl; mono-(halo)-tri-(hydroxyl)phenyl; di(halo)-mono-(hydroxyl)phenyl; di(halo)-di-(hydroxyl)phenyl; di(halo)-tri-(hydroxyl)phenyl; or mono- or di-(halo)-mono- or di-(hydroxy)-mono- or di-(alkoxy)phenyl (i.e., mono-(halo)-mono-(hydroxy)-mono-(alkoxy)phenyl; mono-(halo)-di-(hydroxy)-mono-(alkoxy)phenyl; mono-(halo)-mono-(hydroxy)-di-(alkoxy)phenyl; mono-(halo)-di-(hydroxy)-di-(alkoxy)phenyl; di-(halo)-mono-(hydroxy)-mono-(alkoxy)phenyl; di-(halo)-di-(hydroxy)-mono-(alkoxy)phenyl; or di-(halo)-mono-(hydroxy)-di-(alkoxy) phenyl). In certain specific embodiments, R$^2$ is 2-, 3-, or 4-halophenyl; 3,5-dihalophenyl; 2-, 3-, or 4-hydroxyphenyl; 2,4-dihydroxyphenyl; 3,5-dihalo-2,4,6-trihydroxyphenyl; 3,5-dihalo-2,4-dihydroxyphenyl; 3,5-dihalo-4-hydroxyphenyl; 3-halo-4-hydroxyphenyl; 3,5-dihalo-2-hydroxy-4-methoxyphenyl; or 4-carboxyphenyl, wherein halo is bromo, chloro, fluoro, or iodo. In a more specific embodiment, the halo is bromo. In a more specific embodiment, R$^2$ is 2-, 3-, or 4-halophenyl; 3,5-dihalophenyl; 2-, 3-, or 4-hydroxyphenyl; 2,4-dihydroxyphenyl; 3,5-dihalo-2,4,6-trihydroxyphenyl; 3,5-dihalo-2,4-dihydroxyphenyl; 3,5-dihalo-4-hydroxyphenyl; 3-halo-4-hydroxyphenyl; 3,5-dihalo-2-hydroxy-4-methoxyphenyl; or 4-carboxyphenyl, wherein halo is fluoro, chloro, bromo, or iodo. In a specific embodiment, halo is bromo.

In another particular embodiment of the bioactive agent of formula I(c), R$^1$ is unsubstituted phenyl, or substituted phenyl wherein phenyl is substituted with one or more of hydroxy, C$_{1-8}$ alkyl, aryl, aryloxy, or halo wherein halo is fluoro, chloro, bromo, or iodo. In a specific embodiment, halo is chloro. In another specific embodiment, R$^1$ is substituted phenyl wherein phenyl is substituted with methyl. In yet another embodiment, R$^1$ is quinolinyl or anthracenyl, optionally substituted with one or more of halo, hydroxyl, C$_{1-8}$ alkyl, or C$_{1-8}$ alkoxy. In still another embodiment, R$^1$ is 2-naphthalenyl or 1-naphthalenyl, optionally substituted with one or more of halo, hydroxyl, —SH, —SO$_3$H, C$_{1-8}$ alkyl, aryl, aryloxy, or C$_{1-8}$ alkoxy. In certain embodiments, R$^1$ is mono-(halo)naphthalenyl; di-(halo)naphthalenyl; tri-(halo)naphthalenyl; mono-(hydroxy)naphthalenyl; di-(hydroxy)naphthalenyl; tri-(hydroxy)naphthalenyl; mono-(alkoxy)naphthalenyl; di-(alkoxy)naphthalenyl; tri-(alkoxy)naphthalenyl; mono-(aryloxy)naphthalenyl; di-(aryloxy)naphthalenyl; mono-(alkyl)naphthalenyl; di-(alkyl)naphthalenyl; tri-(alkyl)naphthalenyl; mono-(hydroxy)-naphthalene-sulfonic acid; mono-(hydroxy)-naphthalene-disulfonic acid; mono or di(halo)-mono or di(hydroxy)naphthalenyl; mono-(alkyl)-mono-(alkoxy)-naphthalenyl; or mono-(alkyl)-di-(alkoxy)-naphthalenyl, wherein halo is fluoro, chloro, bromo, or iodo. In yet other specific embodiments, R$^1$ is 2-chlorophenyl, 4-chlorophenyl, 2,4-chlorophenyl, 4-methylphenyl, 2-anthracenyl, or 6-quinolinyl. In other particular embodiments, R$^1$ is quinolinyl or anthracenyl, optionally substituted with one or more of halo, hydroxyl, C$_{1-8}$ alkyl, or C$_{1-8}$ alkoxy. In a more specific embodiment, each of R$^3$ and R$^5$ is the same or different and independently hydrogen, oxo, methyl, or ethyl. In a more specific embodiment, R$^5$ is oxo.

In certain specific embodiments, n=1 to 10, 1 to 15, 1 to 20, 1 to 25, 1 to 50, 1 to 100, 1 to 200, 1 to 250, 1 to 300, or 1 to 400 or any integer between any of the aforementioned ranges.

In another embodiment, provided herein is a bioactive agent having the following formula I: $[(A)-(J)_{n'})]_n$–M, wherein n=1 to 500 and n'=0 or 1; wherein the compound A has a structure of formula A4, or a pharmaceutically acceptable salt or stereoisomer thereof, such that the bioactive agent has the formula I(d): $[A4-(J)_{n'})]_n$–M as follows:

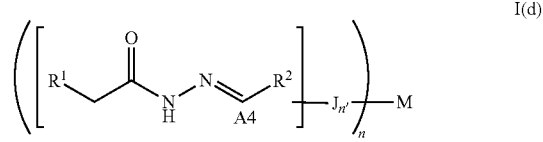

wherein R$^1$ is naphthoxy, naphthylthio, phenoxy, phenyl, naphthalenyl;

R$^2$ is phenyl, optionally substituted with any one or more of hydroxyl, C$_{1-8}$ alkyl, C$_{1-8}$ alkoxy, carboxy, halo, nitro, cyano, —SO$_3$H, —S(=O)$_2$NH$_2$, aryl, and heteroaryl;

J is a spacer that comprises a first end and a second end, wherein the spacer is attached to the compound of formula A4 at the first end of the spacer through a first linker functional group and wherein the spacer is attached to the macromolecular moiety M at the second end of the spacer through a second linker functional group, and wherein the first end of the spacer is attached to compound A4 at R$^1$ or R$^2$ or both R$^1$ and R$^2$;

and wherein when n'=0, M forms a direct bond with at least one of R$^1$ and R$^2$.

In certain specific embodiments, R$^2$ is substituted phenyl, and wherein the phenyl is substituted with one, two, or three halo; one or two carboxy; one, two, or three hydroxyl; one or two halo and one, two, or three hydroxyl; one or two halo, one or two hydroxyl, and one C$_{1-8}$ alkoxy; one or two halo, one hydroxyl, and one or two $C_{1-8}$ alkoxy; one halo, one or two hydroxyl, or one or two $C_{1-8}$ alkoxy. In yet other specific embodiments, $R^2$ is di(hydroxyl)phenyl; mono-(halo)-mono-(hydroxyl)phenyl; mono-(halo)-di-(hydroxyl)phenyl; mono-(halo)-tri-(hydroxyl)phenyl; di(halo)-mono-(hydroxyl)phenyl; di(halo)-di-(hydroxyl)phenyl; di(halo)-tri-(hydroxyl) phenyl; or mono- or di-(halo)-mono- or di-(hydroxy)-mono- or di-(alkoxy)phenyl (i.e., mono-(halo)-mono-(hydroxy)-mono-(alkoxy)phenyl; mono-(halo)-di-(hydroxy)-mono-(alkoxy)phenyl; mono-(halo)-mono-(hydroxy)-di-(alkoxy)phenyl; mono-(halo)-di-(hydroxy)-di-(alkoxy)phenyl; di-(halo)-mono-(hydroxy)-mono-(alkoxy)phenyl; di-(halo)-di-(hydroxy)-mono-(alkoxy)phenyl; or di-(halo)-mono-(hydroxy)-di-(alkoxy)phenyl). In certain specific embodiments, $R^2$ is 2-, 3-, or 4-halophenyl; 3,5-dihalophenyl; 2-, 3-, or 4-hydroxyphenyl; 2,4-dihydroxyphenyl; 3,5-dihalo-2,4,6-trihydroxyphenyl, 3,5-dihalo-2,4-dihydroxyphenyl; 3,5-dihalo-4-hydroxyphenyl; 3-halo-4-hydroxyphenyl; 3,5-dihalo-2-hydroxy-4-methoxyphenyl; or 4-carboxyphenyl, wherein halo is bromo, chloro, fluoro, or iodo. In a more specific embodiment, the halo is bromo. In yet other specific embodiments, $R^2$ is 2-, 3-, or 4-halophenyl; 3,5-dihalophenyl; 2-, 3-, or 4-hydroxyphenyl; 2,4-dihydroxyphenyl; 3,5-dihalo-2,4,6-trihydroxyphenyl; 3,5-dihalo-2,4-dihydroxyphenyl; 3,5-dihalo-4-hydroxyphenyl; 3-halo-4-hydroxyphenyl; 3,5-dihalo-2-hydroxy-4-methoxyphenyl; or 4-carboxyphenyl, wherein halo is chloro, bromo, fluoro, or iodo. In certain specific embodiments, halo is bromo. As noted below in the definitions, a substituted alkyl, cycloalkyl, or heterocyclealkyl may be further substituted. For example, phenoxy is a substituted phenyl, which may be further substituted with any of the substituents defined herein.

In another particular embodiment of the bioactive agent of formula I(d), $R^1$ is unsubstituted phenyl or phenoxy, or substituted phenyl or phenoxy wherein phenyl or phenoxy is substituted with one or more of hydroxy, $C_{1-8}$ alkyl, aryl, aryloxy, or halo wherein halo is fluoro, chloro, bromo, or iodo. In a specific embodiment, halo is chloro.

In another specific embodiment, $R^1$ is substituted phenyl wherein phenyl is substituted with methyl. In still another embodiment, $R^1$ is 2-naphthalenyl or 1-naphthalenyl, naphthoxy, or naphthylthio, optionally substituted with one or more of halo, hydroxyl, —SH, —SO$_3$H, $C_{1-8}$ alkyl, aryl, aryloxy, or $C_{1-8}$ alkoxy. In certain embodiments, naphthalenyl, naphthoxy, or naphthylthio may be substituted. The following exemplify certain substituted naphthalenyl, naphthoxy, or naphthylthio groups using naphthalenyl as the exemplary naphthyl group: $R^1$ is mono-(halo)naphthalenyl; di-(halo)naphthalenyl; tri-(halo)naphthalenyl; mono-(hydroxy)naphthalenyl; di-(hydroxy)naphthalenyl; tri-(hydroxy)naphthalenyl; mono-(alkoxy)naphthalenyl; di-(alkoxy)naphthalenyl; tri-(alkoxy)naphthalenyl; mono-(aryloxy)naphthalenyl; di-(aryloxy)naphthalenyl; mono-(alkyl)naphthalenyl; di-(alkyl)naphthalenyl; tri-(alkyl)naphthalenyl; mono-(hydroxy)-naphthalene-sulfonic acid; mono-(hydroxy)-naphthalene-disulfonic acid; mono or di(halo)-mono or di(hydroxy)naphthalenyl; mono(alkyl)-mono-(alkoxy)-naphthalenyl; or mono-(alkyl)-di-(alkoxy)-naphthalenyl, wherein halo is fluoro, chloro, bromo, or iodo. In yet other specific embodiments, $R^1$ is 2-chlorophenyl, 4-chlorophenyl, 2,4-chlorophenyl, or 4-methylphenyl.

In certain specific embodiments, n=1 to 10, 1 to 15, 1 to 20, 1 to 25, 1 to 50, 1 to 100, 1 to 200, 1 to 250, 1 to 300, or 1 to 400 or any integer between any of the aforementioned ranges.

In one embodiment of the bioactive agent described above, $[(A)-(J)_{n'}]_n$–M, compound A has a structure of subformula A5, or a pharmaceutically acceptable salt or stereoisomer thereof, wherein $R^1$, $R^2$, and $R^3$ are as defined above for a compound having the formula A1, and wherein each of W and D is N, Q is C, and each of $R^4$ and $R^6$ is H, such that the bioactive agent has the formula I(e): $[A5-(J)_{n'}]_n$–M as follows:

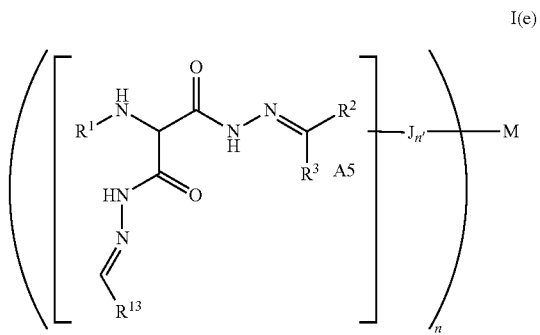

I(e)

wherein $R^{13}$ is phenyl, optionally substituted with at least one hydroxyl, halo, $C_{1-8}$ alkyl, $C_{1-8}$ alkoxy, carboxy, or —S(=O)$_2$O$^-$, isocyanate, isothiocyanate, carboxyester, activated carboxy ester, —SH, or maleimide. In other specific embodiments, $R^{13}$ is -3,5-dibromo-2,4-dihydroxyphenyl, 3,5-dibromo-4-hydroxphenyl, or -2,4-phenyldisulfonate. In certain embodiments, $R^1$ is 2-naphthalenyl or 1-naphthalenyl, optionally substituted with one or more of halo, hydroxyl, —SH, —SO$_3$H, $C_{1-8}$ alkyl, aryl, aryloxy, or $C_{1-8}$ alkoxy. In other certain embodiments, $R^2$ is substituted phenyl, and wherein the phenyl is substituted with one, two, or three halo; one or two carboxy; one, two, or three hydroxyl; one or two halo and one, two, or three hydroxyl; one or two halo, one or two hydroxyl, and one $C_{1-8}$ alkoxy; one or two halo, one hydroxyl, and one or two $C_{1-8}$ alkoxy; or one halo, one or two hydroxyl, and one or two $C_{1-8}$ alkoxy, wherein halo is bromo, chloro, iodo, or fluoro; in a more specific embodiment, halo is bromo. In yet other specific embodiments, $R^2$ is di(hydroxyl) phenyl; mono-(halo)-mono-(hydroxyl)phenyl; mono-(halo)-di-(hydroxyl)phenyl; mono-(halo)-tri-(hydroxyl)phenyl; di(halo)-mono-(hydroxyl)phenyl; di(halo)-di-(hydroxyl) phenyl; di(halo)-tri-(hydroxyl)phenyl; or mono- or di-(halo)-mono- or di-(hydroxy)-mono- or di-(alkoxy)phenyl (i.e., mono-(halo)-mono-(hydroxy)-mono-(alkoxy)phenyl; mono-(halo)-di-(hydroxy)-mono-(alkoxy)phenyl; mono-(halo)-mono-(hydroxy)-di-(alkoxy)phenyl; mono-(halo)-di-(hydroxy)-di-(alkoxy)phenyl; di-(halo)-mono-(hydroxy)-mono-(alkoxy)phenyl; di-(halo)-di-(hydroxy)-mono-(alkoxy) phenyl; or di-(halo)-mono-(hydroxy)-di-(alkoxy)phenyl). In certain specific embodiments, $R^2$ is 2-, 3-, or 4-halophenyl; 3,5-dihalophenyl; 2-, 3-, or 4-hydroxyphenyl; 2,4-dihydroxyphenyl; 3,5-dihalo-2,4,6-trihydroxyphenyl, 3,5-dihalo-2,4-dihydroxyphenyl; 3,5-dihalo-4-hydroxyphenyl; 3-halo-4-hydroxyphenyl; 3,5-dihalo-2-hydroxy-4-methoxyphenyl; or 4-carboxyphenyl, wherein halo is bromo, chloro, fluoro, or iodo. In a more specific embodiment, the halo is bromo. In still yet other embodiments, $R^2$ is 2-, 3-, or 4-halophenyl; 3,5-dihalophenyl; 2-, 3-, or 4-hydroxyphenyl; 2,4-dihydroxyphenyl; 3,5-dihalo-2,4,6-trihydroxyphenyl, 3,5-dihalo-2,4-dihydroxyphenyl; 3,5-dihalo-4-hydroxyphenyl; 3-halo-4-hydroxyphenyl; 3,5-dihalo-2-hydroxy-4-methoxyphenyl; or 4-carboxyphenyl, wherein halo is chloro, fluoro, iodo, and bromo. In a specific embodiment, halo is bromo.

In certain specific embodiments, n=1 to 10, 1 to 15, 1 to 20, 1 to 25, 1 to 50, 1 to 100, 1 to 200, 1 to 250, 1 to 300, or 1 to 400 or any integer between any of the aforementioned ranges.

In another embodiment, the bioactive agent of formula I wherein each of W and D is N, Q is C, $R^1$ is defined as for the compound of formula A1, and each of $R^3$, $R^4$ and $R^6$ is H such that compound A has a structure of formula A6, wherein the first end of J is attached at $R^5$ such that the bioactive agent has the following formula I(f): $[A6-(J_{n'})]_n-M$:

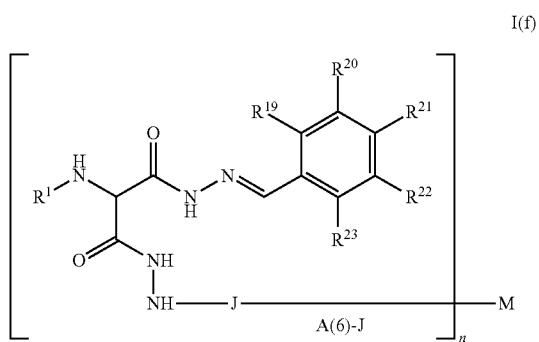

wherein each of $R^{19}$ $R^{20}$, $R^{21}$, $R^{22}$, and $R^{23}$ is the same or different and independently hydrogen, hydroxy, halo, $C_{1-8}$ alkyl, $C_{1-8}$ alkoxy, or carboxy. In certain particular embodiments, each of $R^{20}$ and $R^{22}$ is halo and each of $R^{21}$ and $R^{23}$ is hydroxyl or wherein each of $R^{20}$ and $R^{22}$ is halo and $R^{21}$ is hydroxyl. In more specific embodiments, halo is bromo. In other specific embodiments $R^1$ is 2-naphthalenyl or 1-naphthalenyl, optionally substituted with one or more of halo, hydroxyl, —SH, $C_{1-8}$ alkyl, and $C_{1-8}$ alkoxy; 2-chlorophenyl; 4-chlorophenyl; -2-4-dichlorophenyl, 4-methylphenyl; 2-anthracenyl; or 6-quinolinyl. In yet other specific embodiments, $R^3$ is H, $R^5$ is $C_{1-8}$ alkyl, and J is attached at $R^5$. In yet another specific embodiment, $R^3$ is oxo, $R^5$ is $C_{1-8}$ alkyl, and J is attached at $R^5$. In certain specific embodiments, n=1 to 10, 1 to 15, 1 to 20, 1 to 25, 1 to 50, 1 to 100, 1 to 200, 1 to 250, 1 to 300, or 1 to 400 or any integer between any of the aforementioned ranges.

In one embodiment, the bioactive agent of any one of formula I and subformulae I(a)-I(f) described herein, the spacer J is selected from DIDS (4,4'-diisothiocyanatostilbene-2,2'-disulfonic acid), bis(polyethylene glycol bis[imidazoyl carbonyl]); N-((2-pyridyldithio)ethyl)-4-azidosalicylamide; and maleimidoethyl succinimidyl succinate. In a more specific embodiment, J is selected from structures J1-J30 as set forth in Table 1.

In another embodiment, the bioactive agent of any one of formula I and subformulae I(a)-I(f) described herein M is selected from a lectin, a cell receptor ligand, polylysine, a saccharide, a synthetic polymer, an antibody that specifically binds to a cell surface receptor; an antibody that specifically binds to the extracellular domain of a cell transmembrane polypeptide, an antibody that specifically binds to CFTR, an antibody that specifically binds to a cellular polypeptide that co-expresses with CFTR, and a cell-penetrating peptide. In certain embodiments, M is a lectin selected from a jack bean lectin, a wheat germ lectin, a tomato lectin, an asparagus pea lectin, a scarlet runner bean lectin, a pea lectin, a chick pea lectin, soybean lectin, and lentil lectin, and a potato lectin. In more specific embodiments, the lectin is a jack bean lectin and wherein the jack bean lectin is Concanavalin A, and yet in other specific embodiments, the lectin is a wheat lectin or a tomato lectin.

In one embodiment, the bioactive agent of formula I(f) has $R^1$ that is 2-naphthalenyl or 4-chlorophenyl, $R^{19}$ and $R^{23}$ are H, $R^{20}$ and $R^{22}$ are bromo, $R^{21}$ is hydroxyl, J is DIDS, and M is a lectin, and wherein the bioactive agent has a structure of the following formula I(g) or I(h):

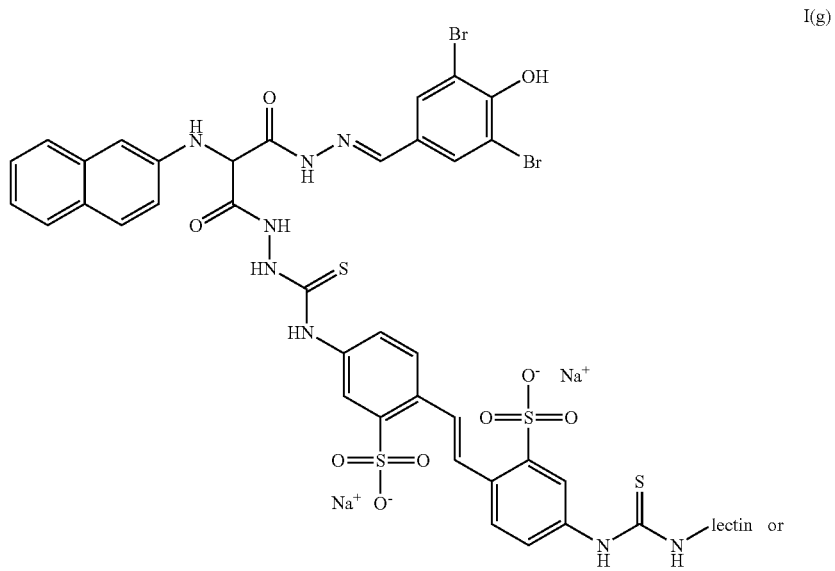

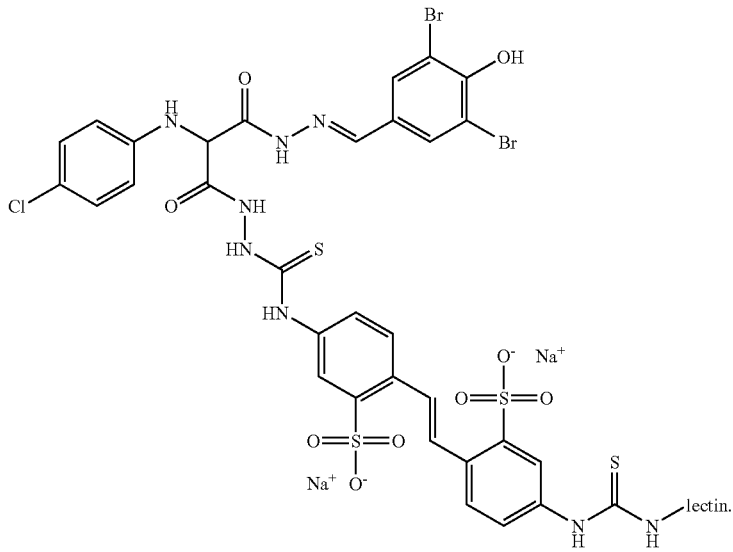

I(h)

In particular embodiments, the lectin is a jack bean lectin, a wheat lectin, a tomato lectin, an asparagus pea lectin, a scarlet runner bean lectin, a pea lectin, a chick pea lectin, a soybean lectin, a lentil lectin, or a potato lectin.

In another embodiment of the bioactive agent of formula I(f), $R^1$ is 2-naphthalenyl, $R^{19}$ is H, $R^{20}$ and $R^{22}$ are each halo, $R^{21}$ is hydroxyl, $R^{23}$ is H or hydroxyl, J is DIDS, and M is a synthetic polymer, such that the bioactive agent has a structure of the following formula I(h):

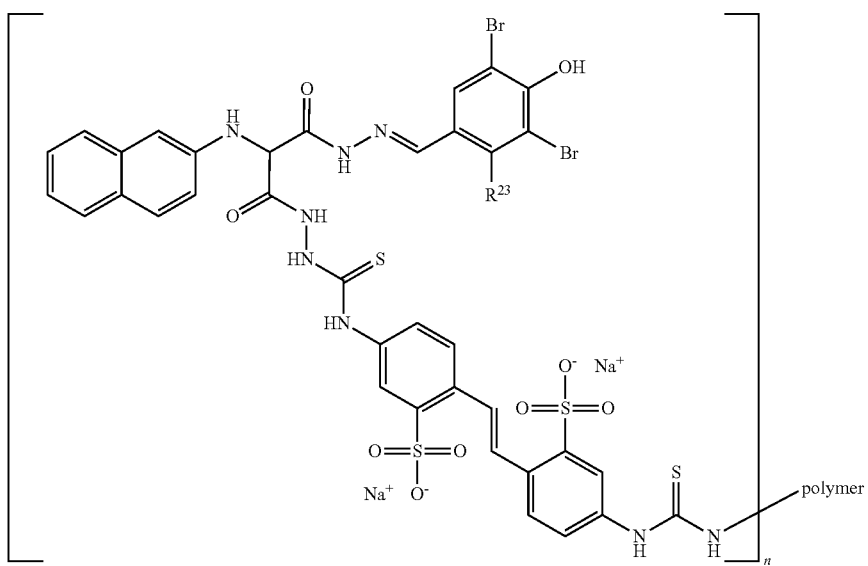

I(h)

wherein n=1-10. In certain specific embodiments, the polymer is a polyamidoamine dendrimer or a polyalkylamine.

In another embodiment, the bioactive agent having a formula of I(f), wherein $R^3$ is oxo, $R^5$ is $C_{1-8}$ alkyl, and J is attached at $R^5$ and wherein J has the structure J30

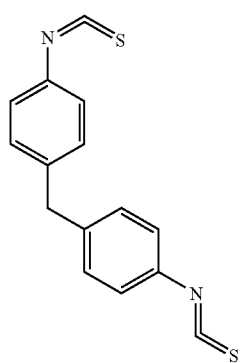

J30 and M is a synthetic polymer wherein the synthetic polymer is a polyamidoamine dendrimer or a polyalkylamine. In particular embodiments, $R^1$ is 2-naphthalenyl, $R^{19}$ is H, $R^{20}$ and $R^{22}$ are each halo, and $R^{21}$ is hydroxyl, and $R^{23}$ is H or hydroxyl.

In certain embodiments, in formula I and subformulae I(a)-I(f) described herein, compound A has a naphthalenyl as the substituent $R^1$. As described herein, the naphthalenyl may be 1-naphthalenyl or 2-naphthalenyl and may be optionally substituted. Exemplary substituted naphthalenyl groups include the following: a mono-(halo)naphthalenyl, such as 1-, 3-, 4-, 5-, 6-, 7-, or 8-chloronaphthalenyl; di(halo)naphthalenyl such as 3,4- or 5,6- or 5,7- or 5,8-dichloronaphthalenyl; a mono-(hydroxy)naphthalenyl, such as 1-, 3-, 4-, 5-, 6-, 7-, or 8-hydroxynaphthalenyl; a di(hydroxy)naphthalenyl 1,8-, 3,4-, dihydroxynaphthalenyl; a mono-(alkoxy)naphthalenyl, such as 1-, 3-, 5-, 6-, 7-, or 8-methoxynaphthalenyl; di-(alkoxy)naphthalenyl such as 5,8-dimethoxynaphthalenyl; tri (alkoxy)naphthalenyl such as 1,4,8-trimethoxynaphthalenyl; a mono-(alkyl)naphthalenyl, such as 1-, 3-, 4-, 5-, or 6-methylnaphthalenyl; di(alkyl)naphthalenyl such as 4,5-, 4,6-dimethynaphthalenyl; a mono-(hydroxy)-naphthalene sulfonic acid, such as 4-hydroxy-2-naphthalene sulfonic acid, 8-hydroxy-3,6-disulfo-naphthalenyl; mono(alkyl)-mono- or di(alkoxy)naphthalenyl, such as 1-methyl-5,6-dimethoxynaphthalenyl. In certain embodiments, $R^1$ is mono-(halo) naphthalenyl; di-(halo)naphthalenyl; mono-(hydroxy) napthalenyl; a di-(hydroxy)napthalenyl; mono-(alkoxy) napthalenyl; di-(alkoxy)napthalenyl; tri-(alkoxy) napthalenyl; mono-(alkyl)napthalenyl; di-(alkyl) napthalenyl; mono-(hydroxy)-mono-napthalene sulfonic acid; mono-(hydroxy)-napthalen-disulfonic acid; mono-(alkyl)-mono-(alkoxy)-naphthalenyl; or mono-(alkyl)-di-(alkoxy)-naphthalenyl. In other embodiments, the substituent or substituents may be aryl or aryloxy.

Also in certain embodiments, compound A described herein has $R^2$ that may be an optionally substituted phenyl. As described above, or in addition to the description above, the substituent $R^2$ is in certain embodiments, optionally substituted as follows. In certain embodiments, the phenyl is substituted with halo, and in particular embodiments, the halo is bromo. For example, $R^2$ includes a mono-(halo)phenyl such as 2-, 3-, or 4-bromophenyl. In other embodiments, $R^2$ is a mono-hydroxyphenyl such as 2,3,4-hydroxyphenyl or is a di(hydroxyl)phenyl such as 2,4-dihydroxyphenyl. In other embodiments, $R^2$ is substituted with two or more different substituents such as for example a mono- or di(halo)-mono-, di-, or tri-(hydroxy)phenyl such as 3,5-dibromo-2,4,6-trihydroxyphenyl, 3,5-dibromo-2,4-dihydroxyphenyl, 3,5-dibromo-4-hydroxyphenyl, or 3-bromo-4-hydroxyphenyl; or a mono- or di(halo)-mono- or di-(hydroxyl)-mono- or di-(alkoxy)phenyl such as 3,5-dibromo-2-hydroxy-4-methoxyphenyl.

Also provided herein are compositions, including pharmaceutical compositions, comprising a pharmaceutically (i.e., physiologically) acceptable excipient and any one of the bioactive agents of any one of formula I and subformulae I(a)-I (h) described herein. Pharmaceutically acceptable excipients are discussed in further detail herein.

Also provided herein are methods of using the bioactive agents having a structure of any one of formula I and subformulae I(a)-I(h) and compositions comprising these agents, which are summarized below and discussed in greater detail herein. In one embodiment, a method is provided for treating a disease or disorder associated with aberrantly increased ion transport by cystic fibrosis transmembrane conductance regulator (CFTR), the method comprising administering to a subject the bioactive agent having a structure of any one of formula I and subformulae I(a)-I(h) described herein (or a composition comprising the bioactive agent and a pharmaceutically acceptable excipient), wherein ion transport by CFTR is inhibited (i.e., ion transport is inhibited, slowed, reduced, abrogated, blocked, or prevented in a statistically or biologically significant manner). Thus, the bioactive agent or composition comprising the bioactive agent is administered in an amount effective to inhibit efflux of the ion from the cell into extracellular space (or environment). In one embodiment, the disease or disorder is aberrantly increased intestinal fluid secretion or secretory diarrhea. In certain embodiments, secretory diarrhea is caused by an enteric pathogen, wherein the enteric pathogen is any one of *Vibrio cholerae, Clostridium difficile, Escherichia coli, Shigella, Salmonella,* rotavirus, *Giardia lamblia, Entamoeba histolytica, Campylobacter jejuni,* and *Cryptosporidium.*

In particular embodiments, secretory diarrhea is induced by an enterotoxin, wherein the enterotoxin is a cholera toxin, an *E. coli* toxin, a *Salmonella* toxin, a *Campylobacter* toxin, or a *Shigella* toxin. In certain other embodiments, secretory diarrhea is a sequelae of ulcerative colitis, irritable bowel syndrome (IBS), AIDS, chemotherapy, or an enteropathogenic infection. In particular embodiments, the subject is a human or non-human animal.

In another embodiment, a method is provided for inhibiting ion transport by a cystic fibrosis transmembrane conductance regulator (CFTR) comprising contacting (a) a cell that comprises CFTR and (b) the bioactive agent having a structure of any one of formula I and subformulae I(a)-I(h) described herein (or a composition comprising the bioactive agent and a physiologically acceptable excipient (e.g., a pharmaceutically acceptable excipient), under conditions and for a time sufficient for the CFTR and the compound to interact. The cell typically comprises CFTR in the outer membrane that facilitates influx and efflux of ions, particularly chloride ions, from or into, respectively, the extracellular environment.

Also provided herein is a method of treating secretory diarrhea comprising administering to a subject a pharmaceutically acceptable excipient and a bioactive agent having a structure of any one of formula I and subformulae I(a)-I(h). In particular embodiments, the subject is a human or non-human animal.

Spacer J

The hydrazide compound that inhibits activity of CFTR is linked or joined to the macromolecular moiety M via the spacer J (which may also be referred to as a linker). The TABLE 1-continued
Exemplary Spacers J1-J30
Table 1: Spacers J1-J30
J8
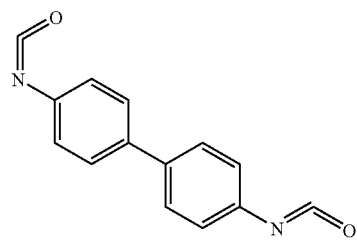 [SMILES: O=C=Nc1ccc(-c2ccc(N=C=O)cc2)cc1]
J9
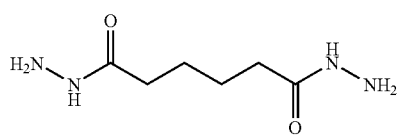 [SMILES: NNC(=O)CCCCC(=O)NN]
J10
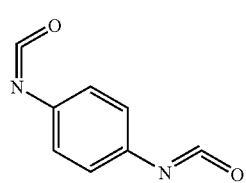 [SMILES: O=C=Nc1ccc(N=C=O)cc1]
J11
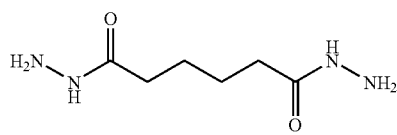 [SMILES: NNC(=O)CCCCC(=O)NN]
J12
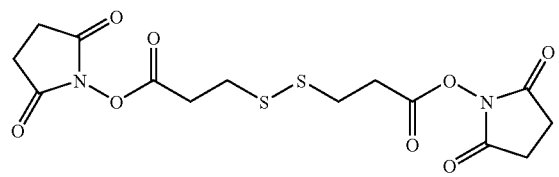 [SMILES: O=C(CCSSCCC(=O)ON1C(=O)CCC1=O)ON1C(=O)CCC1=O]
J13
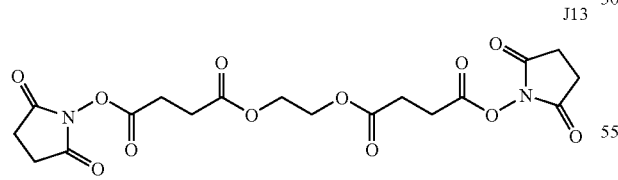
J14
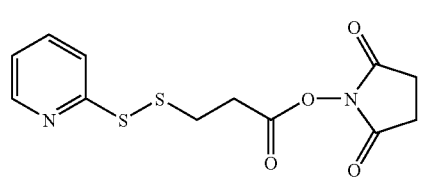 [SMILES: O=C(CCSSc1ccccn1)ON1C(=O)CCC1=O]
TABLE 1-continued
Exemplary Spacers J1-J30
Table 1: Spacers J1-J30
J15
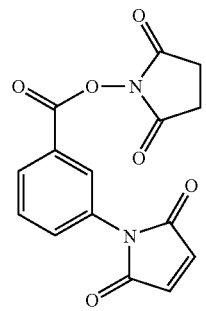 [SMILES: O=C(ON1C(=O)CCC1=O)c1cccc(N2C(=O)C=CC2=O)c1]
J16
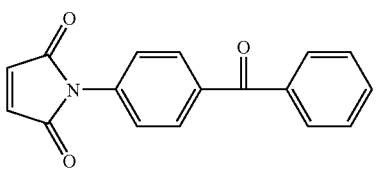 [SMILES: O=C(c1ccccc1)c1ccc(N2C(=O)C=CC2=O)cc1]
J17
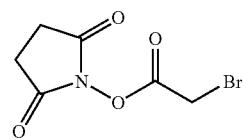 [SMILES: O=C(CBr)ON1C(=O)CCC1=O]
J18
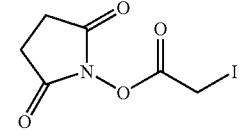 [SMILES: O=C(CI)ON1C(=O)CCC1=O]
J19
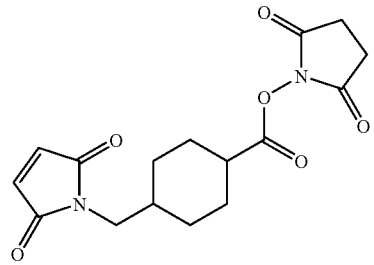 [SMILES: O=C(ON1C(=O)CCC1=O)C1CCC(CN2C(=O)C=CC2=O)CC1]
J20
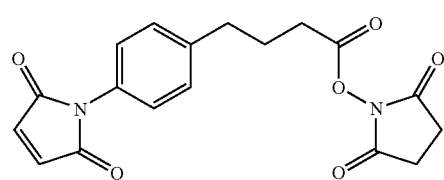 [SMILES: O=C(CCCc1ccc(N2C(=O)C=CC2=O)cc1)ON1C(=O)CCC1=O]

TABLE 1-continued

Exemplary Spacers J1-J30
Table 1: Spacers J1-J30

J21
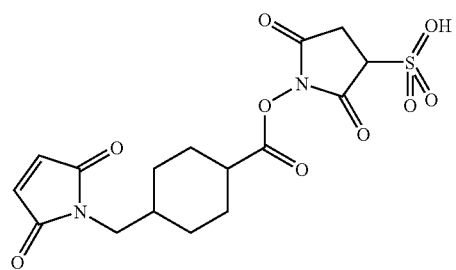

J22
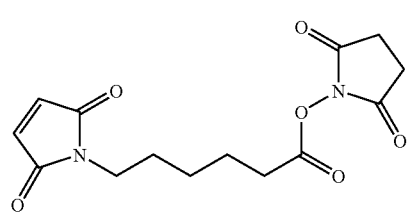 [SMILES: O=C(CCCCCN1C(=O)C=CC1=O)ON1C(=O)CCC1=O]

J23
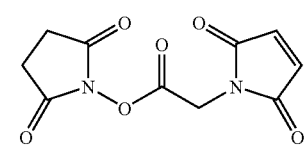 [SMILES: O=C(CN1C(=O)C=CC1=O)ON1C(=O)CCC1=O]

J24
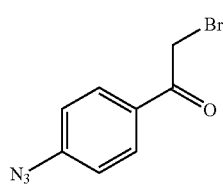 [SMILES: [N-]=[N+]=Nc1ccc(C(=O)CBr)cc1]

J25
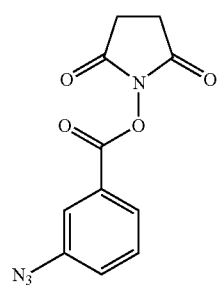 [SMILES: [N-]=[N+]=Nc1cccc(C(=O)ON2C(=O)CCC2=O)c1]

J26
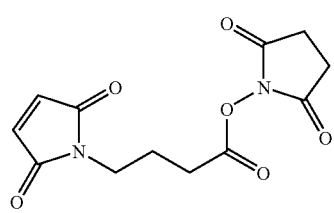 [SMILES: O=C(CCCN1C(=O)C=CC1=O)ON1C(=O)CCC1=O]

TABLE 1-continued

Exemplary Spacers J1-J30
Table 1: Spacers J1-J30

J27
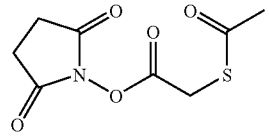

J28
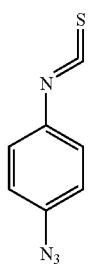

J29
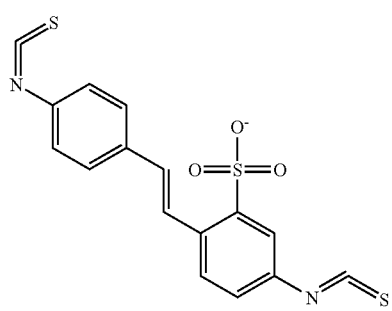 [SMILES: O=S(=O)([O-])c1cc(N=C=S)ccc1/C=C/c1ccc(N=C=S)cc1]

J30
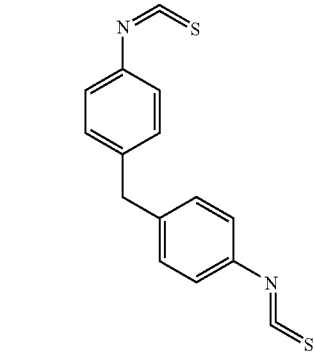 [SMILES: S=C=Nc1ccc(Cc2ccc(N=C=S)cc2)cc1]

In certain embodiments, the spacer or linker may have a first linker functional group at the first end and a third linker functional group in addition to the second linker functional group at the second end. Alternatively, a first spacer J may be attached to a second spacer J' wherein the first linker functional group of J is attached to a compound of formula A (or of any subformulae described herein) and the second linker functional group of J is attached to the first linker functional group of a second spacer J', which is then attached to a macromolecular moiety M via the second linker functional group of J'. An exemplary embodiment is 4-chlorophenyl-MalH-DIDS attached to tris(aminoethyl)amine having the structure shown below.

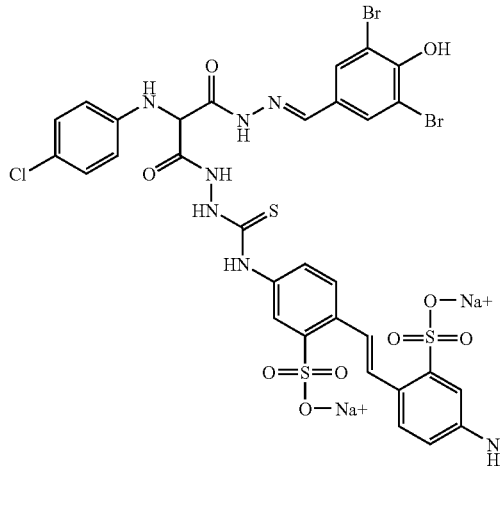
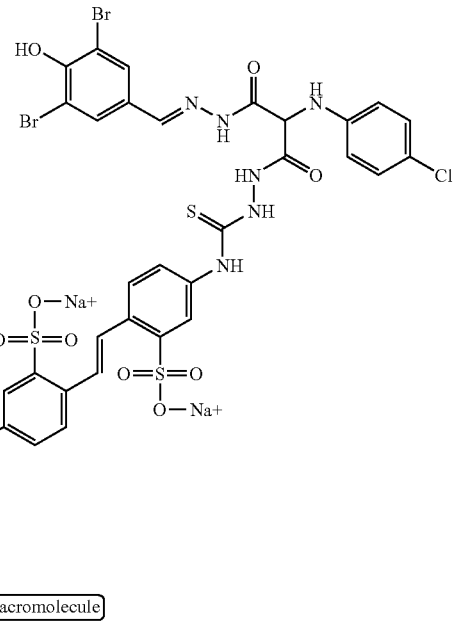

Chemistry Definitions

Certain chemical groups named herein are preceded by a shorthand notation indicating the total number of carbon atoms that are to be found in the indicated chemical group. For example; $C_1$-$C_8$ alkyl describes an alkyl group, as defined below, having a total of 1 to 8 carbon atoms, and $C_3$-$C_{12}$ cycloalkyl describes a cycloalkyl group, as defined below, having a total of 3 to 12 carbon atoms. The total number of carbons in the shorthand notation does not include carbons that may exist in substituents of the group described. In addition to the foregoing, as used herein, unless specified to the contrary, the following terms have the meaning indicated.

"Alkyl" means a straight chain or branched, noncyclic or cyclic, unsaturated or saturated aliphatic hydrocarbon containing from 1 to 18 carbon atoms, while the term "$C_{1-8}$ alkyl" has the same meaning as alkyl but contain from 1 to 8 carbon atoms. Representative saturated straight chain alkyls include methyl, ethyl, n-propyl, n-butyl, n-pentyl, n-hexyl, and the like, while saturated branched alkyls include isopropyl, sec-butyl, isobutyl, tert-butyl, heptyl, n-octyl, isopentyl, 2-ethyl-hexyl and the like. Representative saturated cyclic alkyls include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like; unsaturated cyclic alkyls include cyclopentenyl and cyclohexenyl, and the like. Cyclic alkyls, also referred to as "homocyclic rings," include di- and poly-homocyclic rings such as decalin and adamantyl. Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; representative straight chain and branched alkynyls include acetylenyl, propynyl, 1-butynyl, 2-butynyl, 1-pentynyl, 2-pentynyl, 3-methyl-1 butynyl, and the like.

It is understood that within the context of the compounds described herein that the terms alkyl, aryl, arylalkyl, heterocycle, homocycle, and heterocycloalkyl are taken to comprise unsubstituted alkyl and substituted alkyl, unsubstituted aryl and substituted aryl, unsubstituted arylalkyl and substituted arylalkyl, unsubstituted heterocycle and substituted heterocycle, unsubstituted homocycle and substituted homocycle, unsubstituted heterocycloalkyl and substituted heterocyclealkyl, respectively, as defined herein, unless otherwise specified.

As used herein, the term "substituted" in the context of alkyl, aryl, arylalkyl, heterocycle, and heterocycloalkyl means that at least one hydrogen atom of the alky, aryl, arylalkyl, heterocycle or heterocycloalkyl moiety is replaced with a substituent. In the instance of an oxo substituent ("=O") two hydrogen atoms are replaced. A "substituent" as used within the context of this disclosure includes oxo, halogen, hydroxy, cyano, nitro, amino, alkylamino, dialkylamino, alkyl, alkoxy, thioalkyl, haloalkyl, substituted alkyl, heteroalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocycloalkyl, substituted heterocycloalkyl, —NR$_a$R$_b$, —NR$_a$C(=O)R$_b$, —NR$_a$C(=O)NR$_a$R$_b$, —NR$_a$C(=O)OR$_b$ —NR$_a$S(=O)$_2$R$_b$, —ORR$_a$, —C(=O)R$_a$—C(=O)OR$_a$, —C(=O)NR$_a$R$_b$, —OCH$_2$C(=O)NR$_a$R$_b$, —OC(=O)NR$_a$R$_b$, —SH, —SR$_a$, —SOR$_a$, —S(=O)$_2$NR$_a$R$_b$, —S(=O)$_2$R$_a$, —SR$_a$C(=O)NR$_a$R$_b$, —OS(=O)$_2$R$_a$ and —S(=O)$_2$OR$_a$ (also written as —SO$_3$R$_a$), wherein R$_a$ and R$_b$ are the same or different and independently hydrogen, alkyl, haloalkyl, substituted alkyl, alkoxy, aryl, substituted aryl, arylalkyl, substituted arylalkyl, arylalkoxy, heteroaryl, substituted heteroaryl, heteroarylalkyl, substituted heteroarylalkyl, heterocycle, substituted heterocycle, heterocycloalkyl or substituted heterocycloalkyl. The definitions of R$_a$ and R$_b$ above apply to all uses of these substituents throughout the description.

Representative substituents include (but are not limited to) alkoxy (i.e., alkyl-O—, including $C_{1-8}$ alkoxy e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, alkyloxycarbonyloxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonyl-phenylthio), amino (e.g., amino, mono- and di-$C_1$-$C_3$ alkanylamino, methylphenylamino, methylbenzylamino, $C_1$-$C_3$ alkanylamido, acylamino, carbamamido, ureido, guanidino, nitro and cyano). Moreover, any substituent may have from 1-5 further substituents attached thereto.

"Aryl" means an aromatic carbocyclic moiety such as phenyl or naphthyl (i.e., naphthalenyl) (1- or 2-naphthyl) or anthracenyl (e.g., 2-anthracenyl).

"Arylalkyl" (e.g., phenylalkyl) means an alkyl having at least one alkyl hydrogen atom replaced with an aryl moiety, such as —$CH_2$-phenyl, —CH═CH-phenyl, —C($CH_3$)═CH-phenyl, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl (including 6-quinolinyl), isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined herein. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "optionally substituted" as used in the context of an optionally substituted heterocycle (as well heteroaryl) means that at least one hydrogen atom is replaced with a substituent. In the case of a keto substituent ("—C(═O)—") two hydrogen atoms are replaced. When substituted, one or more of the above groups are substituted.

"Substituents" within the context of description herein are also described above and include halogen, hydroxy, cyano, nitro, amino, alkylamino, dialkylamino, alkyl, alkoxy, alkylthio, haloalkyl, aryl, arylalkyl, heteroaryl, heteroarylalkyl, heterocycle and heterocycloalkyl, as well as —$NR_aR_b$, —$NR_aC(═O)R_b$, —$NR_aC(═O)NR_aR_b$, —$NR_aC(═O)OR_b$—$NR_aS(═O)_2R_b$, —$OR_a$, —C(═O)$R_a$—C(═O)O$R_a$, —C(═O)$NR_aR_b$, —OCH$_2$C(═O)$NR_aR_b$, —OC(═O)$NR_aR_b$, —SH, —$SR_a$, —$SOR_a$, —S(═O)$_2NR_aR_b$, —S(═O)$_2R_a$, —OS(═O)$_2R_a$ and —S(═O)$_2OR_a$. In addition, the above substituents may be further substituted with one or more of the above substituents, such that the substituent is a substituted alkyl, substituted aryl, substituted arylalkyl, substituted heterocycle or substituted heterocycloalkyl. $R_a$ and $R_b$ in this context may be the same or different and independently hydrogen, alkyl, haloalkyl, substituted alkyl, alkoxy, aryl, substituted aryl, arylalkyl, substituted arylalkyl, heterocycle (including heteroaryl), substituted heterocycle (including substituted heteroaryl), heterocycloalkyl, or substituted heterocycloalkyl.

"Heterocycloalkyl" means an alkyl having at least one alkyl hydrogen atom replaced with a heterocycle, such as —$CH_2$-morpholinyl, —$CH_2CH_2$piperidinyl, —$CH_2$azepineyl, —$CH_2$pirazineyl, —$CH_2$pyranyl, —$CH_2$furanyl, —$CH_2$pyrrolidinyl, and the like.

"Homocycle" (also referred to herein as "homocyclic ring") means a saturated or unsaturated (but not aromatic) carbocyclic ring containing from 3-7 carbon atoms, such as cyclopropane, cyclobutane, cyclopentane, cyclohexane, cycloheptane, cyclohexene, and the like.

"Halogen" or "halo" means fluoro, chloro, bromo, and iodo.

"Haloalkyl," which is an example of a substituted alkyl, means an alkyl having at least one hydrogen atom replaced with halogen, such as trifluoromethyl and the like.

"Haloaryl," which is an example of a substituted aryl, means an aryl having at least one hydrogen atom replaced with halogen, such as 4-fluorophenyl and the like.

"Alkoxy" means an alkyl moiety attached through an oxygen bridge (i.e., —O-alkyl) such as methoxy, ethoxy, and the like.

"Haloalkoxy," which is an example, of a substituted alkoxy, means an alkoxy moiety having at least one hydrogen atom replaced with halogen, such as chloromethoxy and the like.

"Alkoxydiyl" means an alkyl moiety attached through two separate oxygen bridges (i.e., —O-alkyl-O—) such as —O—$CH_2$—O—, —O—$CH_2CH_2$—O—, —O—$CH_2CH_2CH_2$—O—, —O—CH($CH_3$)$CH_2CH_2$—O—, —O—$CH_2$C($CH_3$)$_2CH_2$—O—, and the like.

"Alkanediyl" means a divalent alkyl from which two hydrogen atoms are taken from the same carbon atom or from different carbon atoms, such as —$CH_2$—, —$CH_2CH_2$—, —$CH_2CH_2CH_2$—, —CH($CH_3$)$CH_2CH_2$—, —$CH_2$C($CH_3$)$_2CH_2$—, and the like.

"Thioalkyl" means an alkyl moiety attached through a sulfur bridge (i.e., —S-alkyl) such as methylthio, ethylthio, and the like.

"Alkylamino" and "dialkylamino" mean one or two alkyl moieties attached through a nitrogen bridge (i.e., —N-alkyl) such as methylamino, ethylamino, dimethylamino, diethylamino, and the like.

"Carbamate" is FOC(═O)$NR_aR_b$.

"Cyclic carbamate" means any carbamate moiety that is part of a ring.

"Amidyl" is —$NR_aR_b$.

"Hydroxyl" or "hydroxy" refers to the —OH radical.

"Sulfhydryl" or "thio" is —SH.

"Amino" refers to the —$NH_2$ radical.

"Nitro" refers to the —$NO_2$ radical.

"Imino" refers to the ═NH radical.

"Thioxo" refers to the ═S radical.

"Cyano" refers to the —C≡N radical.

"Sulfonamide refers to the radical —S(═O)$_2NH_2$.

"Isocyanate" refers to the —N═C═O radical.

"Isothiocyanate" refers to the —N═C═S radical.

"Azido" refers to the —N═N+═N— radical.

"Carboxy" refers to the —$CO_2$H radical (also depicted as —C(═O)OH).

"Hydrazide" refers to the —C(=O)NR$_a$—NR$_a$R$_b$ radical.

"Oxo" refers to the =O radical.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of structure (I), as well as any and all substructures described herein is intended to encompass any and all pharmaceutically suitable salt forms.

Also contemplated are prodrugs of any of the compounds described herein. Prodrugs are any covalently bonded carriers that release a compound of structure (I), as well as any of the substructures herein, in vivo when such prodrug is administered to a subject. Prodrugs are generally prepared by modifying functional groups in a way such that the modification is cleaved, either by routine manipulation or by an in vivo process, yielding the parent compound. Prodrugs include, for example, compounds described herein when, for example, hydroxy or amine groups are bonded to any group that, when administered to a subject, is cleaved to form the hydroxy or amine groups. Thus, representative examples of prodrugs include (but are not limited to) acetate, formate and benzoate derivatives of alcohol and amine functional groups of the compounds of structure (I), as well as any of the substructures herein. Further, in the case of a carboxylic acid (—COOH), esters may be employed, such as methyl esters, ethyl esters, and the like. Prodrug chemistry is conventional to and routinely practiced by a person having ordinary skill in the art.

Prodrugs are typically rapidly transformed in vivo to yield the parent compound (i.e., a bioactive agent of formula I or subformulae Ia-Ih), for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

With regard to stereoisomers, the compounds of structure (I), as well as any substructure herein, may have one or more chiral centers and may occur in any isomeric form, including racemates, racemic mixtures, and as individual enantiomers or diastereomers. In addition, the compounds of structure (I), as well as any substructure thereof, include E and Z isomers of all double bonds. All such isomeric forms of the compounds are included and contemplated, as well as mixtures thereof. Furthermore, some of the crystalline forms of any compound described herein may exist as polymorphs, which are also included and contemplated by the present disclosure. In addition, some of the compounds may form solvates with water or other organic solvents. Such solvates are similarly included within the scope of compounds and compositions described herein.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatises that detail the synthesis of reactants useful in the preparation of compounds and bioactive agents described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds and bioactive agents described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J.

C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the compounds and bioactive agents described herein is P. H. Stahl & C. G. Wermuth "Handbook of Pharmaceutical Salts", Verlag Helvetica Chimica Acta, Zurich, 2002.

Synthesis of Bioactive Compounds

Synthesis of Hydrazide Compounds

The following reaction schemes illustrate methods to make hydrazide compounds (I.e., compounds having formula A and related structures and substructures). A person having ordinary skill in the chemical art would be able to make the compounds described herein by similar methods or other methods practiced by a person skilled in the art. In general, starting components may be obtained from sources such as Sigma Aldrich (St. Louis, Mo.), or synthesized according to methods and techniques with which a skilled person is familiar (see, e.g., Smith and March, *March's Advanced Organic Chemistry: Reactions, Mechanisms, and Structure,* 5th edition (Wiley Interscience, New York)). The various substituents (e.g., $R^1$, $R^2$, $R^3$, $R^4$, $R^5$, and W and D, etc.) of the compounds may be attached to a starting component or reactant or to an intermediate component or reactant.

An exemplary reaction scheme for synthesis of a hydrazide compound is provided in Reaction Scheme 1. In the Scheme, W of the formula A(1) is nitrogen and D of formula A(1) is nitrogen.

REACTION SCHEME 1

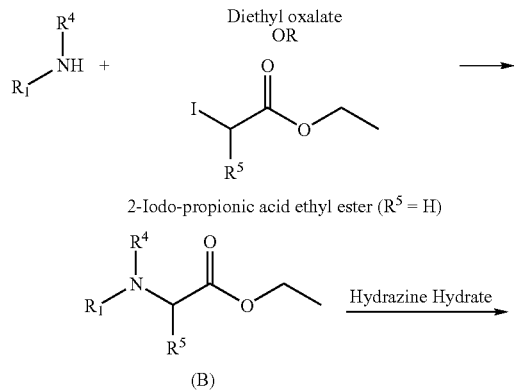

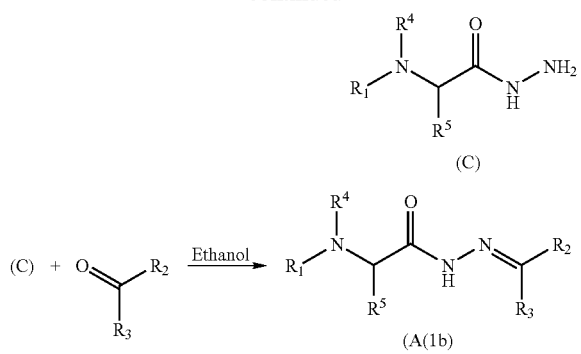

In general, compounds of formula (A) are prepared by first combining an $R^1NH R^4$ with diethyl oxalate or with a compound such as $R^5$-substituted ethyl iodoacetate, wherein $R^5$ is for example, methyl. The definitions of $R^1$, $R^2$, $R^3$, and $R^4$ are provided above. The amount of each reactant is 10 mmol. The reaction mixture is stirred overnight at elevated temperature. Upon cooling, the solid material is filtered and recrystallized from hexane to yield a compound of formula (B). The compound of formula (B) solubilized in ethanol is refluxed with 12 mmol hydrazine hydrate for about 10 hours. The solvent and excess reagent are then distilled under vacuum. The product is recrystallized from ethanol to yield the compound of formula (C). The compound of formula (C) is then combined with a carbonyl-containing reactant to which $R^2$ and $R^3$ are attached (e.g., a ketone or an aldehyde) in ethanol and then refluxed for about 3 hours to yield the desired compound of Formula (A(1b)). When $R^5$ is hydrogen, ethyl iodoacetate may be combined with $R^1NH R^4$.

Alternatively, compounds of formula A(I), such as A(Ib) wherein $R^5$ is an alkyl, which may be substituted or unsubstituted, saturated linear or branched, can be prepared according to the following Reaction Scheme 2 wherein $R_1$, $R^2$, $R^3$, $R^4$ and $R^5$ are as described above in the description of the bioactive agents. In this exemplary reaction scheme 2, $R^5$ is methyl.

REACTION SCHEME 2

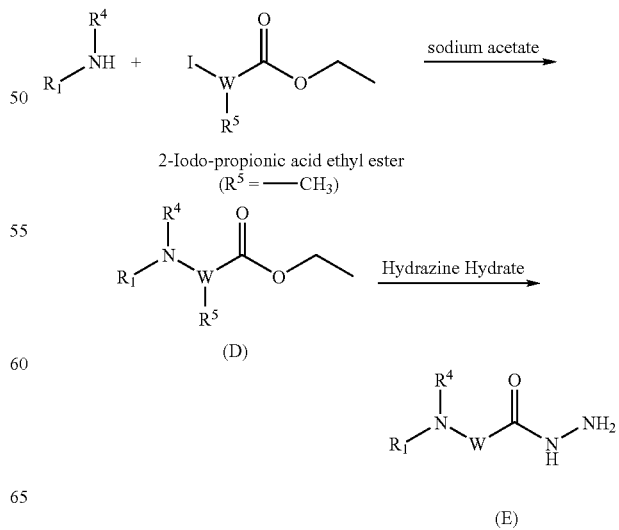

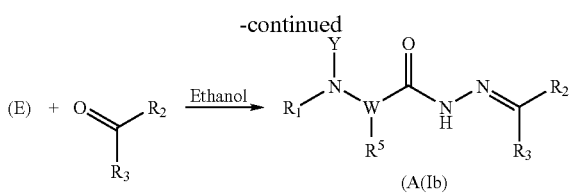

In the above reaction scheme 2, a reactant $R^1NHR^4$ is combined with a compound such as $R^5$-substituted ethyl iodoacetate, wherein $R^5$ is for example, methyl. The definitions of $R^1$, $R^2$, $R^3$, and $R^4$ are provided above. Each reactant at 10 mmol is combined with 20 mmole sodium acetate. The reaction mixture is stirred for about 3 hours at elevated temperature. Upon cooling, the solid material is filtered and recrystallized from hexane to yield a compound of formula (D). The compound of formula (D) solubilized in ethanol is refluxed with 12 mmol hydrazine hydrate for about 10 hours. The solvent and excess reagent are then distilled under vacuum. The product is recrystallized from ethanol to yield the compound of formula (E). The compound of formula (E) is then combined with a carbonyl-containing reactant to which $R^2$ and $R^3$ are attached (e.g., a ketone or an aldehyde) in ethanol and then refluxed for about 3 hours to yield the desired compound of Formula (A(1b)). When $R^5$ is hydrogen, ethyl iodoacetate may be combined with $R^1NHR^4$.

Compounds of Formula (A), wherein $R^5$ is oxo, each of W and B is nitrogen, and $R^6$ is hydrogen can be prepared according to the following Reaction Scheme 3 wherein $R^1$, $R^2$, $R^3$ and $R^4$ are as described above in the description of the bioactive agents.

REACTION SCHEME 3

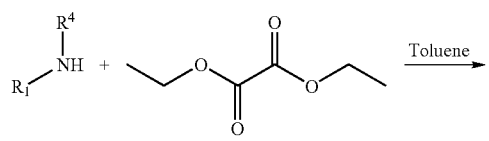

diethyl oxalate

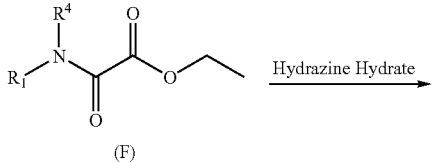

(F)

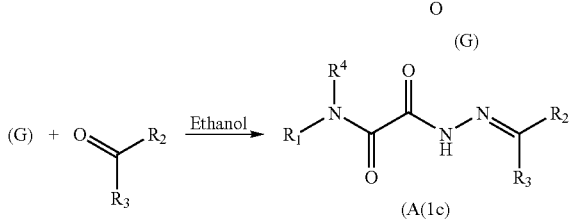

In general, compounds of Formula (A(1c)) are prepared by first combining reactant $R^1NHR^4$ with diethyl oxalate, each at 10 mmol in toluene. The resulting reaction mixture is then stirred at an elevated temperature for about 3 hours. Upon cooling, the solid material is filtered and recrystallized from hexane to yield the compound of formula (F). A solution of the compound of formula (F) in ethanol is then refluxed with 12 mmol hydrazine hydrate for about 10 hours. The solvent and excess reagent are then distilled under vacuum. The product is then recrystallized from ethanol to yield the compound of formula (G). The compound of formula (G) is then combined with a carbonyl-containing reactant to which $R^2$ and $R^3$ are attached (e.g., a ketone or an aldehyde) in ethanol and then refluxed for a period of time of about 3 hours to yield the desired product of Formula (A(1c)).

Compounds of Formula (A), wherein each of W and B is nitrogen, $R^6$ is hydrogen and $R^5$ is, for example, alkyl, phenyl, carboxy, —C(=O)NHNR$^9$R$^{10}$, —C(=O)NHN(=R$^9$), —NR$^9$R$^{10}$; —C(=O)NHNHC(=S)NR$^9$R$^{10}$, —C(=O)R$^9$ or —CH$_2$(CH)$_z$R$^9$ wherein z is 0-7, and wherein each $R^9$, and $R^{10}$ is the same or different and independently H, $C_{1-8}$ alkyl, cycloalkyl, phenyl, alkylphenyl (see, for example, structures of formula A(2) wherein $R^4$ is hydrogen) can be prepared according to the following Reaction Scheme 4. $R^1$, $R^2$, and are as described above in the description of the bioactive agents.

REACTION SCHEME 4

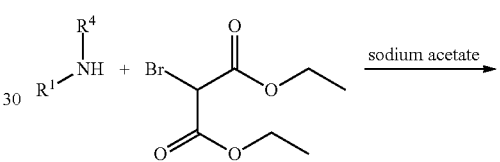

(I)

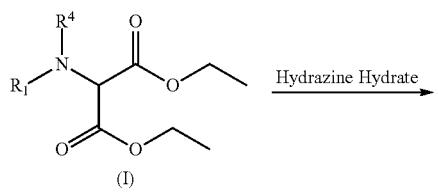

(J)

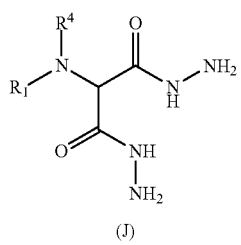

(K)

-continued

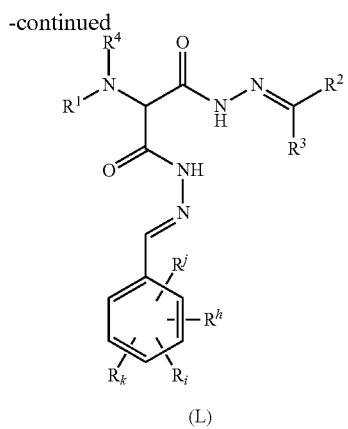

(L)

In Reaction Scheme 4, reactant $R^1NHR^4$ is combined with diethyl bromomalonate, each at 10 mmol. The resulting reaction mixture is then stirred at an elevated temperature for about 8 hours. Upon cooling, the solid material is filtered and recrystallized from hexane to yield the compound of formula (I). A solution of the compound of formula (I) in ethanol is then refluxed with 12 mmol hydrazine hydrate for about 10 hours. The solvent and excess reagent are then distilled under vacuum. The product is then recrystallized from ethanol to yield the compound of formula (J). The compound of formula (J) is then combined with a carbonyl-containing reactant to which $R^2$ and $R^3$ are attached (e.g., a ketone or an aldehyde) in ethanol and then refluxed for about 3 hours to yield the desired product of formula (K). The compound of formula (K) is then combined with a substituted or unsubstituted phenyl group (wherein $R_i$, $R_j$, $R_k$, and $R_h$ may be the same or different and independently any of the substituents described in the definitions including but not limited to halo, alkyl, carboxyl, alkoxy, hydroxyl, $-S(=O)_2OR_a$, $-NR_aR_b$, etc.) and refluxed for a period of time. The product is then recrystallized from ethanol to yield the compound of formula (L).

The structures may be characterized and confirmed using any number of analytical techniques practiced in the art including $^1$H-NMR and mass spectrometry.

Conjugation

Conjugation of a compound having a structure of formula (A) or any related structure or substructure described herein to a macromolecular moiety (M) via a spacer J may be performed using any number of procedures and techniques described herein and practiced by a person skilled in the art. Each of the spacer J and the macromolecular moiety M and the conjugation procedure are selected such that the potency and water solubility of the compound of formula A are not adversely affected in a significant manner. The potency (such as indicated by $IC_{50}$) and solubility of the compound may be determined in a routine manner according to methods described herein and practiced in the art.

A person skilled in the art will readily understand that the valency of a substituent of compound A (e.g., $R^1$, $R^2$, $R^3$, $R^4$, or $R^5$ of a compound of formula A) described herein to which the spacer J will attach adjusts to retain stability of the bioactive agent. In certain instances, conjugation of the cell binding moiety via J to any one of the substituents described herein may require that an atom of the substituent be removed. For example if the first end of J attaches to a compound A at substituent $R^5$, wherein $R^5$ is $-C(=O)NHNR^{11}R^{12}$ and $R^{11}$ and $R^{12}$ are each hydrogen, then one hydrogen may be removed such that the first end of J bonds to the nitrogen atom.

The first end of spacer J may be attached first to a compound of formula A and then the intermediate compound A-J may be reacted with the macromolecular moiety M. Alternatively, the second end of spacer J may be attached first to a macromolecular moiety M and the intermediate J-M is reacted with a compound of formula A to produce the bioactive agent of formula I [$(A-(J)_n]_n-M$].

An exemplary reaction scheme for attaching a compound of formula A to J to form the intermediate A-J includes a reaction as described in Reaction 4 to form a compound of formula K to which the first end of J may be attached. The number (n) of A-J intermediates that may be attached to the macromolecular moiety M may be 1, 2, 3, 4, 5, 6, 7, 8, 9, 10, or any integer between 1 and 500, 1 and 400, 1 and 300, 1 and 250, 1 and 200, 1 and 100, 1 and 50, 1 and 25, 1 and 20, 1 and 15. The number of A-J intermediates that may attach to a macromolecular moiety may depend, in part, on the nature of the macromolecular moiety. For example, a synthetic polymer, such as PEI or polyamidoamine (for example, PAMAM™) described herein, has numerous reactive groups to which the second end of J may be attached. By contrast, a peptide or a disaccharide may have only one point of attachment with which the second end of J may react. Exemplary conjugation methods are described in Examples 1, 7, 8, and 9.

Macromolecular Cell Interacting Moieties

As described herein, the macromolecular moiety (M) is intended to encompass molecules with a molecular weight of 150 daltons (such as small peptides) or greater. The macromolecular moiety may be a peptide (2, 3, 4, 5, 6, 10, 15, or 20 amino acids), a lipid, PEGylated lipid, fatty acid ester, or a lipid like structure in which a fatty acid may be replaced by polyethylene glycol, or a low molecular weight lipophilic aliphatic/aromatic chain. In certain embodiments, the macromolecular moiety M may be any one of a lectin, a lectin-mimetic, a cell receptor ligand, polylysine, a saccharide (e.g., a monosaccharide, disaccharide, or a polysaccharide), dietary fiber, an aminoglycoside, an amino polysaccharide, an amino dextran, a synthetic polymer, an antibody, and a polypeptide or peptide capable of binding to, associating with, or in some manner interacting with, a cell membrane on the basis of a biological, chemical, and/or physical property. The macromolecular moiety interacts with, associates with, or binds to a cellular carbohydrate, polypeptide, or lipid or other macromolecule or portion thereof that is extracellular. The macromolecular moiety may interact with CFTR or with a lipid, carbohydrate, or cell membrane polypeptide within sufficient proximity of CFTR to permit interaction between the CFTR inhibitor moiety of the bioactive agent such that CFTR activity is inhibited. Preferably, the macromolecular moiety is not transported or internalized into the cell such that the bioactive agent is also internalized or transported into the cell. A macromolecular moiety has sufficient capability to interact with the cell or with a cell surface molecule, such that the bioactive agent is retained for a time sufficient at the cell surface for compound A to inhibit CFTR activity (i.e., block, reduce, decrease transport of chloride or occlude the chloride channel or pore in a statistically or biologically significant manner) with minimum absorption by the cell or wash out from the intestine.

Macromolecular moieties described herein may be obtained from commercial sources or may be chemically synthesized according to the nature of the moiety using methods practiced in the art for making a particular moiety. Alternatively, macromolecular moieties that are polypeptides or peptides, may be made by recombinant methods known in the art (see, e.g., Sambrook et al. (*Molecular Cloning: A Laboratory Manual*, 3d Ed., Cold Spring Harbor Laboratory Press (2001); (Ausubel et al. (eds.), *Current Protocols in Molecular Biology*, John Wiley and Sons, Inc., NY, 1987)). (See also, e.g., regarding targeting drugs to cells, Schrama et al., *Nat. Rev. Drug Discov.* 5:147-59 (2006); Hilgenbrink et al., *J. Pharm. Sci.* 94:2135-46 (2005); Peelman et al., *Trends Pharmacol. Sci.* 27:218-25 (2006)).

Lectins

In one embodiment, the macromolecular moiety is a lectin, which may be a plant lectin (including a legume lectin, cereal lectin, peanut lectin, jacalin and others described herein) or animal lectin (e.g., a galectin, C-type, R-type, calnexin, calreticulin, M-type, L-type, P-type, I-type, F-box lectin, ficolin, chitinase-like lectins, F-type, intelectins). Lectins are carbohydrate-binding proteins or glycoproteins that specifically bind certain sugar moieties (see, e.g., Loris et al., *Biochem. Biophys. Acta* 1383:9-36 (1998); Sharon and Lis *Lectins, 2nd* ed. Kluwer Academic (2003); *The Lectins: Properties, Functions, and Applications in Biology and Medicine*, Liener et al., eds., Academic Press, Inc., Orlando, (1986)). The lectins useful for making and using the bioactive agents described herein may bind to CFTR or may bind to another glycoprotein or glycolipid present in the cellular outer membrane (see also, e.g., Bies et al., *Adv. Drug Deliv. Rev.* 56:425-35 (2004); Clark et al., *Adv. Drug. Deliv. Rev.* 43:207-23 (2000)). Lectins that are known toxins such as ricin are excluded from the lectins described herein.

Exemplary lectins that may be used as cell-binding moieties of the bioactive agents described herein include but are not limited to jack bean lectin (*Canavalia ensiformis*) (commonly known as Concanavalin A), a wheat lectin such as a wheat germ lectin (e.g., from *Triticum vulgaris*), a tomato lectin (e.g., from *Lycopersicon esculentum*) (see, e.g., Kilpatrick et al., *FEBS Lett.* 185:299-305 (1985); Kilpatrick et al., *Anal Biochem.* 134:205-209 (1983); Nachbar et al., *J. Biol. Chem.* 255:2056-61 (1980)), an asparagus pea lectin (e.g., from *Tetragonolobus purpureas* (*Lotus tetragonolobus*)); a scarlet runner bean lectin, a pea lectin, a chick pea lectin, a soybean lectin, a lentil lectin, a peanut lectin, and a potato lectin. Any one of the lectins described herein or known in the art may be obtained from a commercial vendor or may be purified from the plant or animal source using methods practiced by a skilled artisan (see, e.g., Kilpatrick et al., supra; Nachbar et al., supra).

Synthetic Polymers

In certain embodiments, the cell binding moiety is a synthetic polymer. Exemplary synthetic polymers include a polyoxyalkyl polyether, a polyethylene glycol (PEG), a polypropylene glycol, a polyhydroxyethyl glycerol, a dendrimer, a polyalkylamine, a polyalkylimine, polyethyleneimine, and polylysine. Synthetic polymers of differing molecular weights are available depending upon the extent of polymerization.

In one embodiment, the synthetic polymer that is a macromolecular moiety M includes a dendrimer, which is a regularly branched fully synthetic polymer molecule that resembles the branches of a tree (see, e.g., Tomalia et al., *Polymer J.* 17; 117-32 (1985); Jiang et al., *Nature* 388:454-56 (1997)). Dendrimers are nearly perfectly monodisperse (i.e., consistent in size and form) macromolecules that have a regular and highly branched three-dimensional architecture. Dendrimers have a high degree of molecular uniformity, narrow molecular weight distribution, specific size and shape characteristics, and a highly-functionalized terminal surface. The architectural components may be referred to as the core, branches, and end (or terminal) groups. The functional groups at the terminal surface can be attached to the second of the spacer J described herein. The term "generation" relates to the manufacturing process by which dendrimers are made and indicates the size and branching complexity of the dendrimer. Dendrimers are manufactured according to a series of repetitive steps starting with a central initiator core, and each subsequent growth step represents a new "generation" of polymer with a larger molecular diameter, twice the number of reactive surface sites, and approximately double the molecular weight of the preceding generation. In one embodiment, a dendrimer is a PAMAM™ dendrimer (Dendritech® Inc., Midland, Mich.), which represents a class of macromolecular architecture also called "dense star" polymers.

In another embodiment, the synthetic polymer is a polyalkylamine, such as polyethyleneimine (PEI), which is known to bind to cells. A monomer of ethyleneimine consists of a three-membered ring with a formula of $C_2H_5N$. In a polyethyleneimine, a monomer has two corners of the molecule consisting of —$CH_2$— linkages, and the third corner is a secondary amine group, =NH. In the presence of a catalyst this monomer is converted into a highly branched polymer with about 25% primary amine groups, 50% secondary amine groups, and 25% tertiary amine groups. Thus, the polymer has an overall positive charge. In still another embodiment, the synthetic polymer is a polylysine, which has an overall positive charge. The polylysine may be a poly-L-lysine or a poly-D-lysine. When a synthetic polymer is conjugated to a CFTR inhibitor compound described herein, the bioactive agent may be positively charged, negatively charged, or may be zwitterionic in nature.

Cell Receptor Ligands and Antibodies

In certain embodiments, the macromolecular moiety is a cell receptor ligand or an antibody. Exemplary cell receptor ligands include transferrin or a carbohydrate that will bind to a lectin expressed by a gastrointestinal cell that expresses CFTR. For example, the macromolecular moiety of the bioactive agent may be lactose, which is capable of binding to an endogenous lectin. The ligand or antibody or other polypeptide may interact with CFTR or with a lipid, carbohydrate, or cell membrane polypeptide within sufficient proximity of CFTR to permit interaction between the CFTR inhibitor moiety of the bioactive agent such that CFTR activity is inhibited.

Antibodies that may be useful as macromolecular moieties include antibodies that specifically bind to a cell surface polypeptide, such as a cell receptor, or that specifically bind to CFTR or to a protein that co-expresses with CFTR. Antibodies that bind to cell receptors and to CFTR may be obtained from a commercial source or may be prepared according to methods routinely practiced in the art (*Current Protocols in Immunology*, 1:2.5.1-2.6.7 (John Wiley & Sons 1991); U.S. Pat. Nos. 4,902,614, 4,543,439, and 4,411,993; *Monoclonal Antibodies, Hybridomas: A New Dimension in Biological Analyses*, Plenum Press, Kennett et al. (eds.) (1980); and *Antibodies: A Laboratory Manual*, Harlow and Lane (eds.), Cold Spring Harbor Laboratory Press (1988); WO 92/02551; U.S. Pat. No. 5,627,052; Babcook et al., *Proc. Natl. Acad. Sci. USA* 93:7843-48 (1996); Winter et al., *Annu. Rev. Immunol.* 12:433-55 (1994); Burton et al., *Adv. Immunol.* 57:191-280 (1994); U.S. Pat. No. 5,223,409; Huse et al., *Science* 246:1275-81 (1989)). The antibody is preferably a fully human, humanized, or a chimeric antibody (with a human Fc portion) or may be an antigen binding fragment thereof, for example, Fab, Fab', F(ab')$_2$, or an Fv or a single chain Fv antigen binding fragment. If desired, the Fc portion of an antibody may be genetically engineered to reduce Fc binding to receptors on immune cells or to reduce complement activating activity (see, e.g., Wines et al., *J. Immunol.* 164:5313-18 (2000); Chappel et al., *Proc. Natl. Acad. Sci. USA* 88:9036

(1991); Canfield et al., *J. Exp. Med.* 173:1483 (1991); Duncan et al *Nature* 332:563-64 (1988); Morgan et al., *Immunology* 86:319-24 (1995)).

Peptides

Peptides that may be used as a macromolecular moiety include peptides that bind to or interact with a cell outer membrane, or a component thereof. The peptide may interact with CFTR or with a lipid, carbohydrate, or polypeptide within sufficient proximity of CFTR to permit interaction between the CFTR inhibitor moiety of the bioactive agent such that CFTR activity is inhibited. Peptides that may be used as the macromolecular moiety may be derived from ligands that react with cell receptors. Alternatively, peptides may be identified from screening combinatorial peptide libraries.

A macromolecular moiety that may be conjugated to a CFTR inhibitor compound includes a peptide known to interact with the cell membrane. Such a peptide include penetratin (PEN) and TAT, derived from the HIV-1 TAT protein (see, e.g., Tseng et al., *Molecular Pharmacology* 62:864-72 (2002); Richard et al., *J. Biol. Chem.* 278:585-90 (2003) Epub 2002 Oct. 30). Without wishing to be bound by theory, a peptide that is capable of binding to a cell membrane may be useful because of its membrane binding capability and yet when conjugated to a CFTR inhibitor does not enter the cell.

Methods for Characterizing the Bioactive Agents

The bioactive agents described herein are capable of blocking or impeding the CFTR pore or channel and inhibiting ion transport by CFTR located in the outer cell membrane of a cell. Also provided herein are methods of inhibiting ion transport by CFTR, which comprises contacting a cell that has CFTR in the outer membrane with any one of the bioactive agents described herein, under conditions and for a time sufficient for the CFTR and the compound to interact. Bioactive agents may be identified and/or characterized by such a method of inhibiting ion transport by CFTR, performed with isolated cells in vitro. Conditions for a particular assay include temperature, buffers (including salts, cations, media), and other components that maintain the integrity of the cell and the bioactive agent, which a person skilled in the art will be familiar and/or which can be readily determined. A person skilled in the art also readily appreciates that appropriate controls can be designed and included when performing the in vitro methods described herein.

Methods for characterizing a bioactive agent, such as determining an effective concentration, may be performed using techniques and procedures described herein and routinely practiced by a person skilled in the art. Exemplary methods include short circuit apical chloride ion current measurements and patch-clamp analysis (see, e.g., Muanprasat et al., *J. Gen. Physiol.* 124:125-37 (2004); Ma et al., *J. Clin. Invest.* 110: 1651-58 (2002); see also, e.g., Carmeliet, *Verh. K. Acad. Geneeskd. Belg.* 55:5-26 (1993); Hamill et al., *Pflugers Arch.* 391:85-100 (1981)). The bioactive agents may also be analyzed in animal models, for example, a closed intestinal loop model of cholera, suckling mouse model of cholera, and in vivo imaging of gastrointestinal transit (see, e.g., Takeda et al., *Infect. Immun.* 19:752-54 (1978)).

Methods of Using the Bioactive Agents and Pharmaceutical Compositions

As described herein, the bioactive agents are capable of inhibiting CFTR activity (i.e., inhibiting, reducing, decreasing, blocking transport of chloride ion in the CFTR channel or pore in a statistically significant or biologically significant manner) in a cell and may be used for treating diseases, disorders, and conditions that result from or are related to aberrantly increased CFTR activity. Accordingly, methods of inhibiting ion transport by CFTR are provided herein that comprise contacting a cell (e.g., a gastrointestinal cell) that comprises CFTR in the outer membrane of the cell (i.e., a cell that expresses CFTR and has channels or pores formed by CFTR in the cell membrane) with any one or more of the bioactive agents described herein, under conditions and for a time sufficient for CFTR and the compound to interact.

The cell may be obtained from a subject or from a biological sample. A biological sample may be a blood sample (from which serum or plasma may be prepared and cells isolated), biopsy specimen, body fluids (e.g., lung lavage, ascites, mucosal washings, synovial fluid), bone marrow, lymph nodes, tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., immune cells, virus infected cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiable cell lines, transformed cell lines, and the like.

Diseases and disorders that may be treated by administering a bioactive agent described herein include aberrantly increased intestinal fluid secretion, such as secretory diarrhea. Secretory diarrhea can result from exposure to a variety of enteropathogenic organisms (i.e., enteric pathogen) including, without limitation, bacteria such as cholera (*Vibrio cholera*), *E. coli* (particularly enterotoxigenic (ETEC)), *Shigella, Salmonella, Campylobacter, Clostridium difficile*; parasites (e.g., *Giardia, Entamoeba histolytica, Cryptosporidiosis, Cyclospora*); and diarrheal viruses (e.g., rotavirus, Group A and Group C; norovirus, sapovirus). Secretory diarrhea may also be a disorder or sequelae associated with food poisoning, or exposure to a toxin including an enterotoxin such as cholera toxin, a *E. coli* toxin, a *Salmonella* toxin, a *Campylobacter* toxin, or a *Shigella* toxin.

Other secretory diarrheas that may be treated by administering the bioactive agents described herein include diarrhea associated with or that is a sequelae of AIDS, diarrhea that is a condition related to the effects of anti-AIDS medications such as protease inhibitors, diarrhea that is a condition or is related to administration of chemotherapeutic compounds, inflammatory gastrointestinal disorders, such as ulcerative colitis, inflammatory bowel disease (IBD), Crohn's disease, diverticulosis, and the like. Intestinal inflammation modulates the expression of three major mediators of intestinal salt transport and may contribute to diarrhea in ulcerative colitis both by increasing transepithelial Cl⁻ secretion and by inhibiting the epithelial NaCl absorption (see, e.g., Lohi et al., *Am. J. Physiol. Gastrointest. Liver Physiol.* 283:G567-75 (2002)).

Methods are provided herein for treating a disease or disorder associated with aberrantly increased ion transport by cystic fibrosis transmembrane conductance regulator (CFTR), wherein the methods comprise administering to a subject any one (or more) bioactive agent described herein, wherein ion transport (particularly chloride ion transport) by CFTR is inhibited. A subject in need of such treatment includes humans and non-human animals. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The bioactive agents may be formulated in a pharmaceutical composition for use in treatment, which includes preventive treatment, of a disease or disorder manifested by increased intestinal fluid secretion, such as secretory diarrhea. A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, $21^{st}$ Ed. Mack Pub. Co., Easton, Pa. (2005)). In general, the type of excipient is selected based on the mode of administration. Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

A composition comprising any one of the bioactive agents having a structure of formula I or subformulae I(a)-I(h) as described herein (such as a malonic hydrazide compound conjugated to a macromolecular moiety such as a lectin) may be formulated for sustained or slow release. Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

The dose of the composition for treating a disease or disorder associated with aberrant CFTR function, including but not limited to intestinal fluid secretion, secretory diarrhea, such as a toxin-induced diarrhea, or secretory diarrhea associated with or a sequelae of an enteropathogenic infection, Traveler's diarrhea, ulcerative colitis, irritable bowel syndrome (IBS), AIDS, chemotherapy and other diseases or conditions described herein may be determined according to parameters understood by a person skilled in the medical art. Accordingly, the appropriate dose may depend upon the subject's condition, that is, stage of the disease, general health status, as well as age, gender, and weight, and other factors considered by a person skilled in the medical art.

Pharmaceutical compositions may be administered in a manner appropriate to the disease or disorder to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose (or effective dose) and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Clinical assessment of the level of dehydration and/or electrolyte imbalance may be performed to determine the level of effectiveness of a bioactive agent and whether dose or other administration parameters (such as frequency of administration or route of administration) should be adjusted.

Optimal doses may generally be determined using experimental models and/or clinical trials. The optimal dose may depend upon the body mass, weight, or blood volume of the subject. In general, the amount of a small molecule compound conjugate as described herein, that is present in a dose, ranges from about 0.01 µg to about 1000 µg per kg weight of the host. The use of the minimum dose that is sufficient to provide effective therapy is usually preferred. Subjects may generally be monitored for therapeutic effectiveness using assays suitable for the condition being treated or prevented, which assays will be familiar to those having ordinary skill in the art and are described herein.

Other embodiments and uses will be apparent to one skilled in the art in light of the present disclosures. The following examples are provided merely as illustrative of various embodiments and shall not be construed to limit the invention in any way.

EXAMPLES

Example 1

Synthesis of a Lectin-Malonic Hydrazide Conjugate

A malonic acid hydrazide intermediate that is formed during the synthesis of highly polar malonic acid hydrazides (see Sonawane et al, *FASEB J.* 20:130-32 (2006)) was reacted with the homo-bifunctional crosslinker DIDS to yield the reactive CFTR inhibitor, MalH-DIDS. The DIDS linker is very polar and relatively rigid, which renders MalH-DIDS highly water soluble. MalH-DIDS was conjugated to several lectins (and to albumin as a control) in an alkaline carbonate buffer and then purified by gel filtration, affinity chromatography, and/or dialysis.

Synthesis of a Malonic Hydrazide Compound Linked to the Bifunctional Cross-Linker DIDS (4,4'-diisothiocyanatostilbene-2,2'-disulfonic acid)

2-naphthalenylamino-[(3,5-dibromo-4-dihydroxyphenyl)methylene]hydrazide [[[4-[2-(4-isothiocyanato-2-sulfophenypethenyl]-2-sulfophenyl]amino]thioxomethyl]hydrazide-propanedioic acid, disodium salt (MalH-DIDS): A mixture of dihydrazide intermediate 4 (Sonawane et al, (2006), supra) (5 mmol) and 4,4'-diisothiocyanatostilbene-2,2'-disulfonic acid disodium salt hydrate (15 mmol) in DMF (5 ml) was refluxed for 4 h. After cooling, the reaction mixture was added dropwise to a stirred solution of EtOAc:EtOH (1:1), filtered, washed with ethanol, and further purified by column chromatography to give MalH-DIDS (43%) as a pale yellow solid.

$^1$H and $^{13}$C NMR spectra were obtained in CDCl$_3$ or DMSO-d$_6$ using a 400 MHz Varian Spectrometer referenced to CDCl$_3$ or DMSO. Mass spectrometry was performed using a Waters LC/MS system (Alliance HT 2790+ZQ, HPLC, Waters model 2690, Milford, Mass.). Flash chromatography was performed using EM silica gel (230-400 mesh), and thin layer chromatography was performed on Merk silica gel 60 F254 plates (Merk, Darmstadt, Germany).

The MalH-DIDS compound had the following properties: mp>300° C.; $^1$H NMR (DMSO-d$_6$): δ 4.98, 5.63 (d, 1H, J=9.88, 8.51 Hz, COCH), 6.33-6.51 (m, 1H, Ar—H), 6.71, 6.84 (m, 1H, Ar—H), 7.03-7.37 (m, 4H, Ar—H & Ar—NH), 7.42-7.65 (m, 4H, Ar—H), 7.77-7.92 (m, 3H, Ar—H), 7.98-8.11 m, 1H), 8.93 (s, 1H), 9.13, 9.15, 9.21 (three s, 1H), 11.62, 11.70 (two s, 1H), 11.98, 12.00, 12.21 (s, 1H). All signals between 8.93-12.21 and 4.98, 5.63 were D$_2$O exchangeable; MS (ES$^+$) (m/z): [M–1]$^-$ calculated for C$_{36}$H$_{25}$Br$_2$N$_7$O$_9$S$_4$, 987.71. found 986.44.

Conjugation to Lectins

MalH-DIDS was then conjugated to different lectins. The following lectins were purchased from Sigma-Aldrich, St. Louis, Mo.: concanavalin A (ConA) (agglutinin from jack beans (*Canavalia ensiformis*)); wheat germ (from *Triticum vulgaris*); tomato (from *Lycopersicon esculentum*); and asparagus pea (from *Tetragonolobus purpureas* (Lotus *tetragonolobus*)). Each lectin (100 nM in 1 ml 50 mM carbonate buffer, pH 8-9) was combined with MalH-DIDS (600 nM in 150 mM ml carbonate buffer, pH 8-9) and each reaction was stirred slowly at room temperature for 30-60 minutes. Unreacted MalH-DIDS was removed either by gel filtration (Sephadex G25, NAP-5 or NAP-10 columns) or by dialysis against PBS. For some preparations, MalH-lectin conjugates were further purified by affinity column chromatography using D-mannose-agarose (Sigma Aldrich, St. Louis, Mo.).

According to molar absorbance data, MalH-DIDS:protein ratios were 3.8:1 (MalH:ConA), 3.2:1 (MalH:wheat), 4.2:1 (MalH:tomato), and 3.4:1 (MalH:asparagus pea). LC/MS analysis showed absence of unconjugated MalH-DIDS.

For TMR labeling, MalH-ConA was reacted with tetramethylrhodamine succinimidyl ester (Molecular Probes, Eugene, Oreg.) (1:3 mole:mole) in carbonate buffer, pH 8.5, for 1 hr. The reaction mixture was then purified by gel filtration (Sephadex® G25 in a NAP-5™ or NAP-10™ column, GE Healthcare). Some preparations were further purified by affinity chromatography as described above.

Example 2

MalH-Lectin Conjugate Inhibits CFTR Transport Activity

This Example describes that the lectin moiety of a MalH-lectin conjugate binds to cell surface carbohydrates and that the conjugate inhibits the activity of CFTR.

Short-Circuit Current Measurements.

T84 (a human carcinoma line (colonic epithelial cells); American Type Culture Collection (ATCC), Manassas, Va.) and Fischer rat thyroid (FRT), epithelial cells that stably expressed human wildtype CFTR), were cultured on Snapwell filters with 1 cm$^2$ surface area (Coming-Costar) to resistance>1,000 Ωcm$^2$ as described (see, e.g., Muanprasat et al., *J. Gen. Physiol.* 124:125-37 (2004); Ma et al., *J. Clin. Invest.* 110:1651-58 (2002); Zegarra-Moran et al., *Br. J. Pharmacol.* 137:504-512 (2002)). Filters were mounted in an Easymount Chamber System (Physiologic Instruments, San Diego). When apical Cl$^-$ current measurements were determined in FRT cells, the basolateral hemichamber contained the following buffer: 130 mM NaCl, 2.7 mM KCl, 1.5 mM KH$_2$PO$_4$, 1 mM CaCl$_2$, 0.5 mM MgCl$_2$, 10 mM Na-HEPES, 10 mM glucose (pH 7.3). The basolateral membrane was permeabilized with amphotericin B (250 μg/ml) for 30 min. In the apical solution, 65 mM NaCl was replaced by sodium gluconate, and CaCl$_2$ was increased to 2 mM. Short-circuit current in T84 cells was measured without amphotericin B or a transepithelial Cl$^-$ gradient. Solutions were bubbled with 95% O$_2$/5% CO$_2$ and maintained at 37° C. Current was recorded using a DVC-1000 voltage-clamp (World Precision Instruments, Sarasota, Fla.) using Ag/AgCl electrodes and 1 M KCl agar bridges.

CFTR inhibition was measured in FRT epithelial cells that expressed human wildtype CFTR. FIG. 1A shows concentration-dependent inhibition of CFTR-mediated apical membrane chloride current by MalH-ConA and MalH-wheat, which was added to the solution that bathed the apical cell surface. CFTR chloride current was inhibited by MalH-ConA at an IC$_{50}$ of 50-100 nM and by MalH-wheat at an IC$_{50}$ of 100-300 nM; complete inhibition was observed at higher concentrations. Unconjugated MalH-DIDS inhibited CFTR chloride current rapidly, but at an IC$_{50}$ of 1000 nM (see FIG. 1B). Without wishing to be bound by theory, the substantial improvement in inhibition potency of MalH-ConA compared with the unconjugated malonic hydrazide may be due to anchoring of the ConA lectin moiety to the cell membrane carbohydrates that comprise the cell surface glycocalyx. Inhibition of CFTR activity by the negative controls, ConA alone or by a MalH-albumin conjugate, is also shown in FIG. 1. Other MalH-lectin conjugates, MalH-tomato, from *Lycopersicum esculentum* agglutinin, and MalH-asparagus, asparagus pea from *Lotus tetragonolobus* agglutinin also exhibited submicromolar $IC_{50}$ values of ~240 and 320 nM, respectively.

Example 3

Increased Potency of Small Molecule Compounds to Inhibit CFTR

This Example describes that the increased effectiveness of MalH-lectin conjugates to inhibit CFTR transport activity results from binding of the lectin moiety of a MalH-lectin conjugate to carbohydrate.

Carbohydrate binding to lectins is generally preserved following conjugation with various small molecules (see, e.g., Gunther et al., *Proc. Natl. Acad. Sci. USA* 70:1012 (1973); Gabor et al., *Adv. Drug Deliv. Rev.;* 56:459-80 (2004); Smart J. D., *Adv. Drug Deliv. Rev.* 56:481-89 (2004)). To show that the high CFTR inhibition potency of MalH-ConA was due to lectin-carbohydrate binding, competition studies using unconjugated ConA was performed. Short circuit current experiments were performed as described in Example 2. Addition of excess ConA (5 μM) greatly reduced the potency of subsequently added MalH-ConA. Representative apical membrane current data are shown in the left panel of FIG. 2A, and the average concentration-inhibition data are summarized in the right panel. For comparison, experiments were performed with MalH-DIDS in the absence and presence of 5 μM ConA. The concentration-inhibition data for MalH-DIDS are presented in FIG. 2A (right panel). ConA pretreatment did not affect MalH-DIDS potency. Inhibition of chloride current by MalH-ConA was determined in the presence of 20 or 200 mM mannose. As shown in FIG. 2B, reduced MalH-ConA inhibition potency was observed after disruption of ConA-carbohydrate binding by 20 mM and 200 mM mannose. However, 200 mM mannose did not affect the CFTR inhibitory potency of MalH-DIDS (FIG. 2B, right panel).

The effect of binding of ConA with carbohydrate to the potency of the MalH-lectin conjugate also was determined in experiments in which ConA was denatured. ConA is a tetramer at pH ~7 and higher, and a dimer at pH below ~6 (see, e.g., Mandal et al., *Biochemistry* 32:5116-20 (1993)). Each ConA monomer (molecular weight, 26,500) contains a single saccharide binding site, a transition metal ion binding site, and a $Ca^{2+}$ binding site (Brewer et al., *Biochemistry* 22:3691-702 (1983); Goldstein et al., *Biochemistry* 4:876 (1964)). In pH-denaturation experiments, MalH-ConA was incubated overnight at pH 5.2, resulting in significant reduction in MalH-ConA inhibition potency (see FIG. 3A, top). Denaturation of ConA at very low pH (1.5 for 15-30 min) completely abolished the capability of MalH-ConA to inhibit CFTR. Incubations of MalH-DIDS at either pH 1.5 or pH 5.2 did not affect the capability of MalH-DIDS to inhibit CFTR (see FIG. 3B, top). Denaturation of MalH-ConA by heat (100° C. for 5 min) abolished its CFTR inhibition activity (see FIG. 3A, middle); whereas, heat treatment did not affect inhibition of CFTR by MalH-DIDS (see FIG. 3B, middle). Similar results were observed for MalH-wheat (MalH conjugated to wheat germ lectin) and MalH-tomato (MalH conjugated to tomato lectin) when each was heat denatured, resulting in complete loss in the capability of either conjugate to inhibit CFTR.

Short circuit current experiments were also performed after treating MalH-ConA with pronase and after incubation in EDTA. A sample of MalH-ConA was digested with pronase for 8 hours at pH 8 and at 37° C. according to the method described in Doyle et al., *Carbohydr. Res.* 29:265-70 (1973)). Denaturation of ConA was confirmed by SDS-PAGE. The pronase-denatured compound did not inhibit CFTR (FIG. 3A, bottom), whereas the potency of similarly treated MalH-DIDS was not affected (FIG. 3B, bottom). Lastly, ConA binding to carbohydrate was reduced by chelation of divalent cations ($Ca^{2+}$ and $Mg^{2+}$) (see, e.g., Goldstein et al., supra; Sumner et al., *J. Biol. Chem.* 115:583 (1936)). EDTA greatly reduced ConA-MalH inhibition potency as shown in FIG. 3A, bottom. Treatment of MalH-DIDS with EDTA did not affect the potency of MalH-DIDS. The concentration-inhibition data for each point is the mean ±SE of measurements for 3-8 cell culture samples.

Example 4

External CFTR Occlusion by MalH-Lectin Conjugates

This Example describes that MalH-lectin acts at the external site of the CFTR channel.

The voltage-sensitivity of blocking CFTR by MalH-ConA was measured by whole-cell patch-clamp. Patch-clamp experiments were carried out at room temperature on FRT cells that stably expressed wildtype CFTR. Whole-cell and outside-out configurations were used (see, e.g., Hamill et al., *Pflugers Arch.* 391:85-100 (1981)). For whole-cell experiments, the pipette solution contained 120 mM CsCl, 10 mM TEA-Cl, 0.5 mM EGTA, 1 mM $MgCl_2$, 40 mM mannitol, 10 mM Cs-HEPES and 3 mM MgATP (pH 7.3). For outside-out patches, the pipette solution contained 50 mM N-methyl-D-glucamine chloride (NMDG-Cl), 2 mM $MgCl_2$, 10 mM EGTA, 10 mM Hepes, 1 mM ATP (pH 7.3). This pipette solution was supplemented with 125 nM catalytic subunit of protein kinase A. The bath solution in all experiments was 150 mM NaCl, 1 mM $CaCl_2$, 1 mM $MgCl_2$, 10 mM glucose, 10 mM mannitol, 10 mM Na-Hepes (pH 7.4). The cell membrane was clamped at specified voltages using an EPC-7 patch-clamp amplifier (List Medical). Data were filtered at 500 Hz (whole cell) or 200 Hz (outside-out) and digitized at 1000 Hz using an Instrutech ITC-16 AD/DA interface (InstruTECH, Port Washington, N.Y.) and the PULSE software (HEKA Instruments, Inc., Southboro, Mass.). Inhibitors were applied by extracellular perfusion.

Membrane currents were induced at different membrane potentials (from −100 to +100 mV) in 20 mV steps. Currents were recorded under resting conditions, after CFTR activation with 20 μM forskolin, and following addition of 250 nM MalH-ConA. Kinetics of blocking by MalH-ConA (250 nM) were compared with GlyH-101 (5 μM) after stepping the membrane potential to +80 mV. As shown in FIG. 4, CFTR stimulation by forskolin produced typical CFTR membrane currents with a linear current-voltage relationship (FIG. 4A, middle panel). MalH-ConA (250 nM) produced a voltage-dependent block of CFTR current (FIG. 4A, lower panel), with greater inhibition of membrane current at positive membrane potentials as shown in FIG. 4B. This inward rectification behavior is similar to the behavior observed for GlyH-101 ($N^2$-naphthalenyl-[3,5-[dibromo-2,4-dihydroxyphenyl) methylene]glycine hydrazide) (see U.S. Patent Application Publication No. 2005/0239740) at much higher concentrations. Similar inward rectification was found for MalH-tomato. The kinetics of block and unblock of CFTR current by MalH-ConA was seen from the relaxations produced by the voltage steps. Changes in membrane potential to more positive values produced a time-dependent decrease in current, with time-dependent activation seen when stepping the membrane potential to negative values. The kinetics of current relaxations were considerably slower than those observed with GlyH-101 (FIG. 4A, inset). The current decay with MalH-ConA fitted to a single exponential function with time constant of 150-200 ms, much faster than that of 8-10 ms found for GlyH-101. Without wishing to be bound by any particular theory, the slower kinetics of block and unblock by MalH-ConA compared with GlyH-101 may reflect the larger size of MalH-ConA and the possibility that the lectin conjugate interacts at multiple sites with surface carbohydrates, retarding its access to and exit from the pore.

Figure 4:
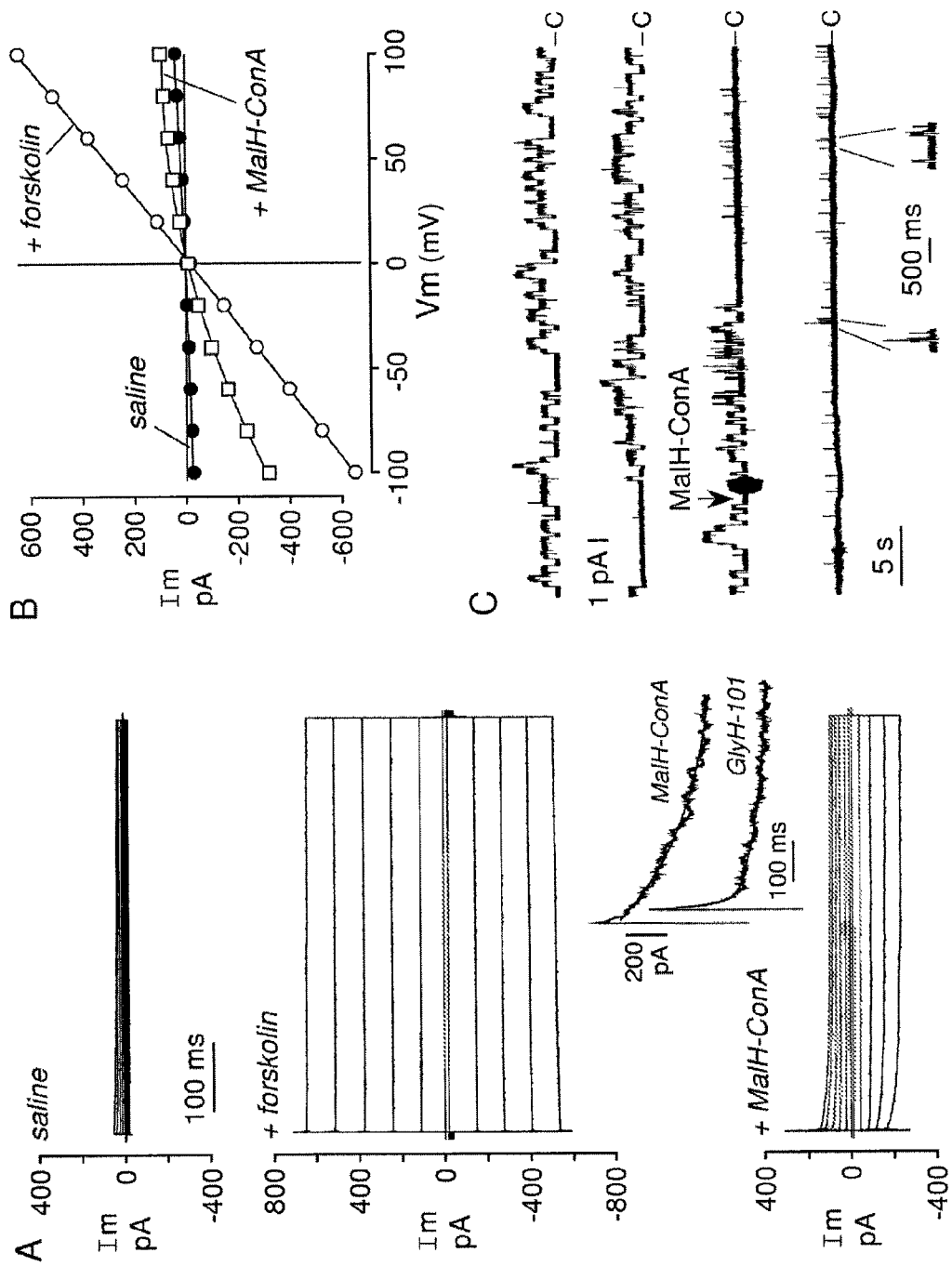
FIGS. 4A-4C present electrophysiological analysis of CFTR inhibition by MalH-lectin.

Single channel recordings were done to evaluate MalH-ConA block at the microscopic level. Because MalH-ConA does not cross the plasma membrane, the outside-out configuration of the patch-clamp technique was used to allow access to the extracellular side of membrane. CFTR was activated by inclusion of ATP and the catalytic subunit of protein kinase A in the pipette (cytosolic side) solution. Addition of MalH-ConA (100 nM) to membrane patches reduced CFTR Cl⁻ conductance with shortening of open time duration as shown in FIG. 4C. The mean open time decreased from 795±94 to 51±10 ms.

Example 5

Lectin Conjugation Retards Washout of MalH-Lectin CFTR Inhibitors

This Example describes reversibility of MalH-ConA inhibition of CFTR chloride current.

Figure 5A:
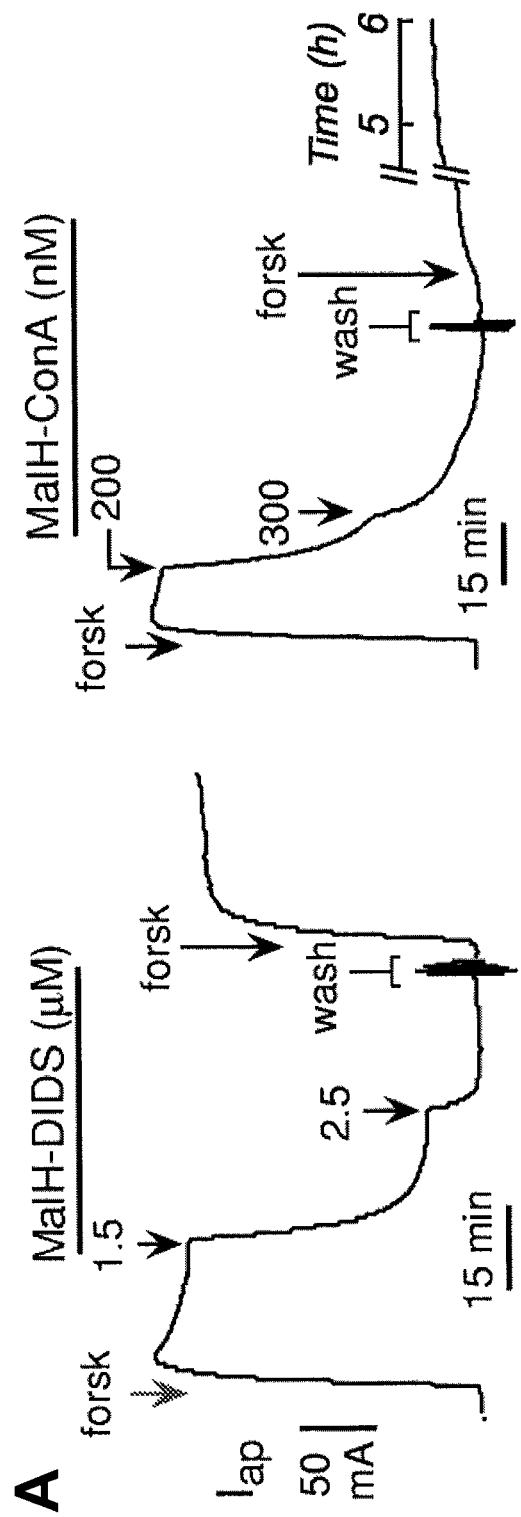
FIG. 5A-5D present data indicating the slow-washout of MalH-ConA.

Following forskolin-stimulation of CFTR chloride current in the whole cell patch clamp assay, cells were incubated with MalH-DIDS or MalH-ConA to achieve 95-100% inhibition, followed by washout and forskolin re-addition (see FIG. 5A). Near-complete and rapid reversal of CFTR inhibition was seen in cells incubated with MalH-DIDS, whereas limited and slow reversal over six hours was observed when cells were incubated with MalH-ConA. The kinetics of reversal of CFTR inhibition by MalH-ConA was also studied by measuring apical membrane chloride current at different times after PBS wash. Cells were treated with 300 nM MalH-ConA for 15 min, washed thoroughly with PBS, and assayed for apical membrane chloride current at different times. Chloride current increased slowly with incubation time, with 50% 'reversal' at approximately 8 h.

Figure 5B:
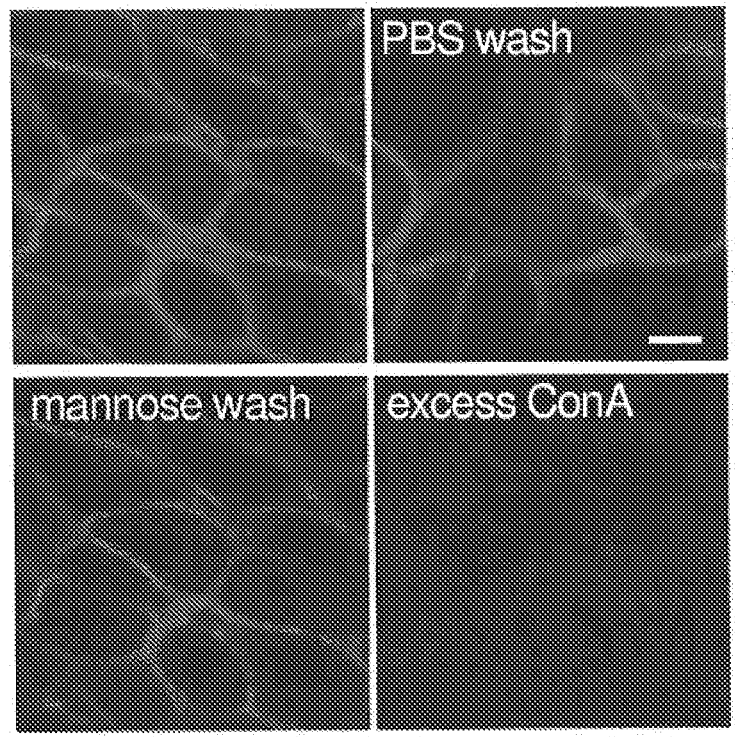

The reversibility of MalH-ConA binding to cells was determined directly by imaging cell fluorescence after incubating the cells with TMR-labeled MalH-ConA (see Example 1), followed by washing. The TMR conjugation procedure did not affect MalH-ConA inhibition potency. FIG. 5B shows TMR fluorescence images of FRT cells after labeling at 4° C. for 3 min with MalH-TMR-ConA (100 µg/ml) and washed with PBS for 5 or 30 min or following addition of 200 mM mannose. Fluorescence images were also taken after cells were preincubated with ConA prior to labeling.

Figure 5C:
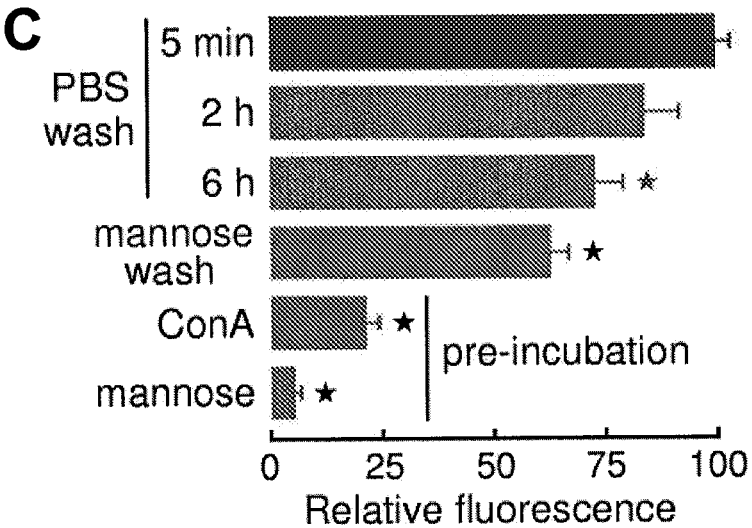

Little reduction in fluorescence was seen after PBS washout, but greater than 35% reduction was observed after the mannose wash. Addition of excess of free ConA prior to TMR-MalH-ConA labeling abolished most of the signal. FIG. 5C summarizes relative cell TMR fluorescence measured at various washout times and conditions, and for ConA or mannose pre-incubation.

Figure 5D:
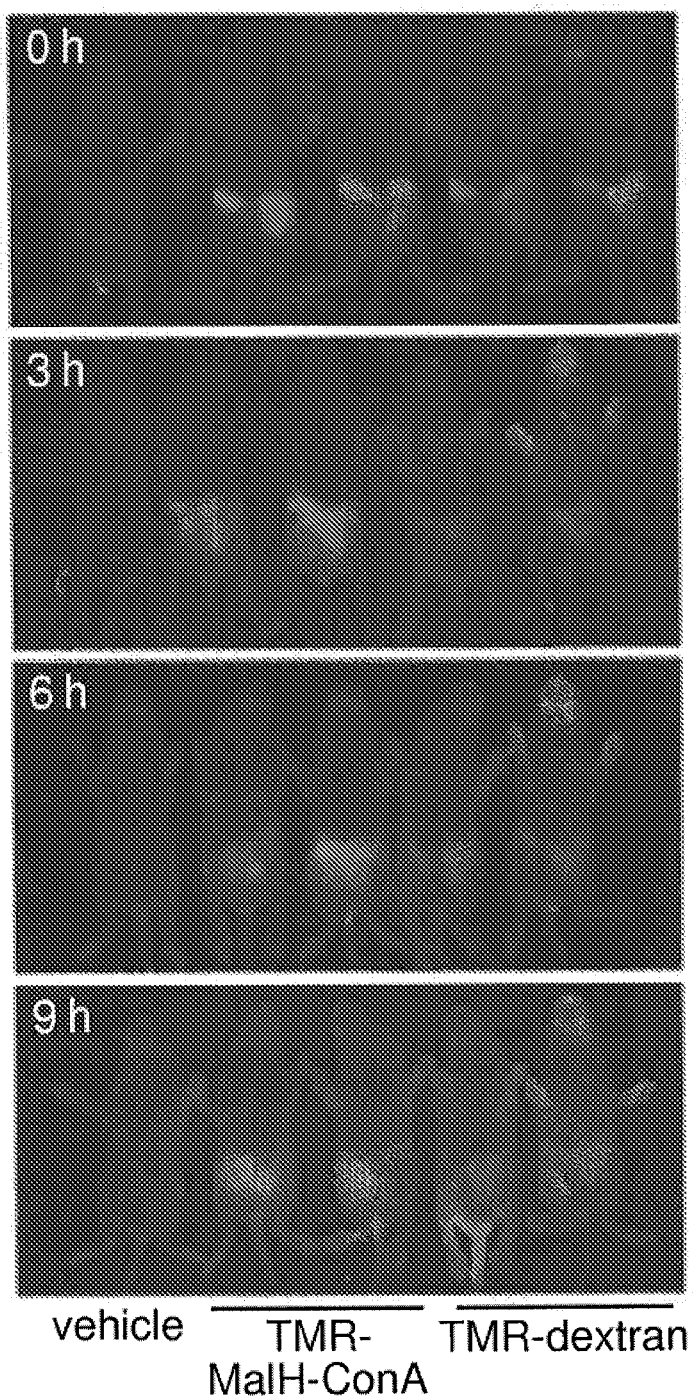

MalH-ConA washout in vivo was investigated in small, suckling mice by whole body fluorescence imaging. In vivo imaging of gastrointestinal transit was performed using Balb-C mice (age 3-4 days) that were gavaged with solutions containing epi-fluorescent TMR-dextran or TMR-MalH-ConA. At specified times the mice were anesthetized with isoflurane. Whole body epifluorescence images were collected using a Kodak model 4000 multimodal-imaging system equipped with an excitation/emission bandpass filters at 535 and 600 nm, respectively. Exposure time was 5 min. Images were acquired at different times following gavage with TMR-MalH-ConA or TMR-dextran, each together with cholera toxin to increase intestinal transit. FIG. 5D shows that TMR-MalH-ConA remained concentrated in the intestine for up to 9 h, over which time the fluorescence of TMR-dextran was largely gone. These observations support the conclusion from cell studies that the lectin conjugates are relatively resistant to washout.

Example 6

MalH-ConA Inhibits Cholera Toxin-Induced Intestinal Fluid Secretion

This Example describes that MalH-ConA inhibits intestinal fluid secretion that is induced by cholera toxin.

Figure 6A:
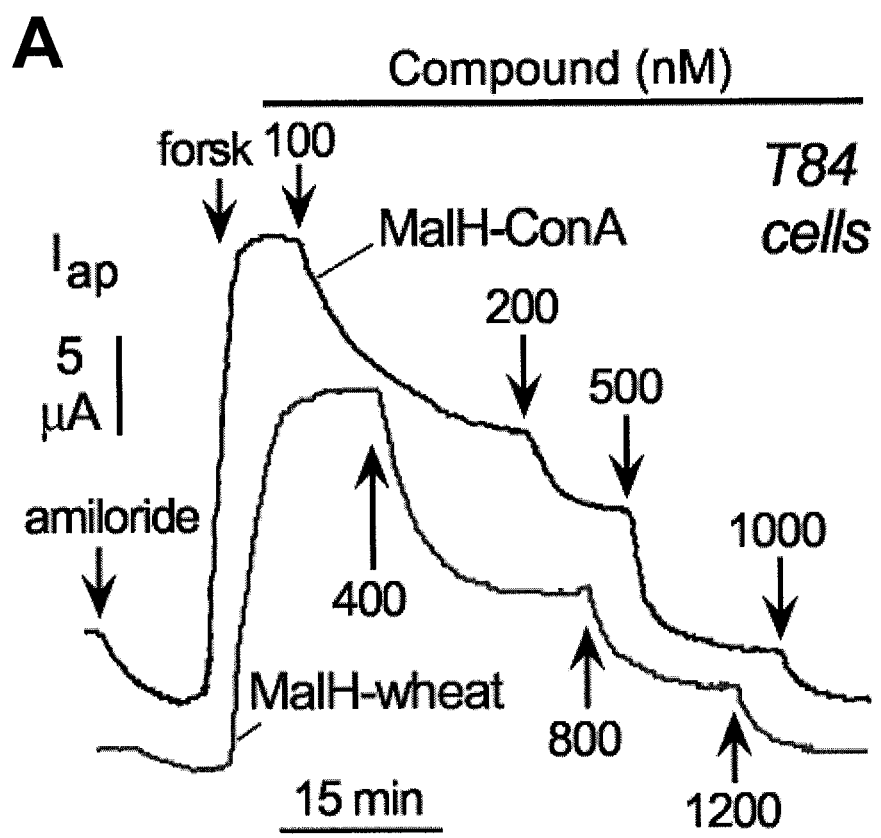
FIGS. 6A-6C present data showing that MalH-ConA and MalH-wheat effectively inhibited intestinal fluid secretion.

MalH-ConA and MalH-wheat inhibited short-circuit current in non-permeabilized T84 cells after CFTR stimulation (see Example 2). CFTR was activated by the addition of forskolin to T84 cells after epithelial sodium channel (EnaC) inhibition by amiloride in absence of chloride gradient. As shown in FIG. 6A, the $IC_{50}$ of MalH-ConA was approximately 200 nM and the $IC_{50}$ of MalH-wheat was approximately 400 nM. Nearly complete inhibition was observed at 1 µM of the lectin conjugates.

The capability of MalH-lectin to inhibit intestinal fluid secretion was examined in mice using a closed intestinal midjejunal loop model of cholera. Mice (CD1 strain, 28-34 g) were deprived of food for 24 h but given 5% sucrose in water ad libitum and then anaesthetized with 2.5% avertin intraperitoneally. Body temperature of the animals was maintained at 36-38° C. by applying a heating pad. A small abdominal incision was made, and three closed mid-jejunal loops (length 15-20 mm) were isolated by sutures. Loops were injected with 100 µl of PBS or PBS containing cholera toxin (1 µg) without or with test compounds. The abdominal incision was closed with suture and mice were allowed to recover from anesthesia. At 6 h the mice were anesthetized, intestinal loops were removed, and loop length and weight were measured to quantify net fluid accumulation. In some experiments, intestinal fluid absorption (without cholera toxin) was measured by injection of loops with 100 µL phosphate buffered saline containing 10 mM glucose, with or without test compounds, and the fluid remaining at 20 min was measured by the difference in weight of intact and empty loop. Mice were sacrificed by an overdose of avertin. All protocols were approved by the University of California at San Francisco Committee on Animal Research.

Figure 6B:
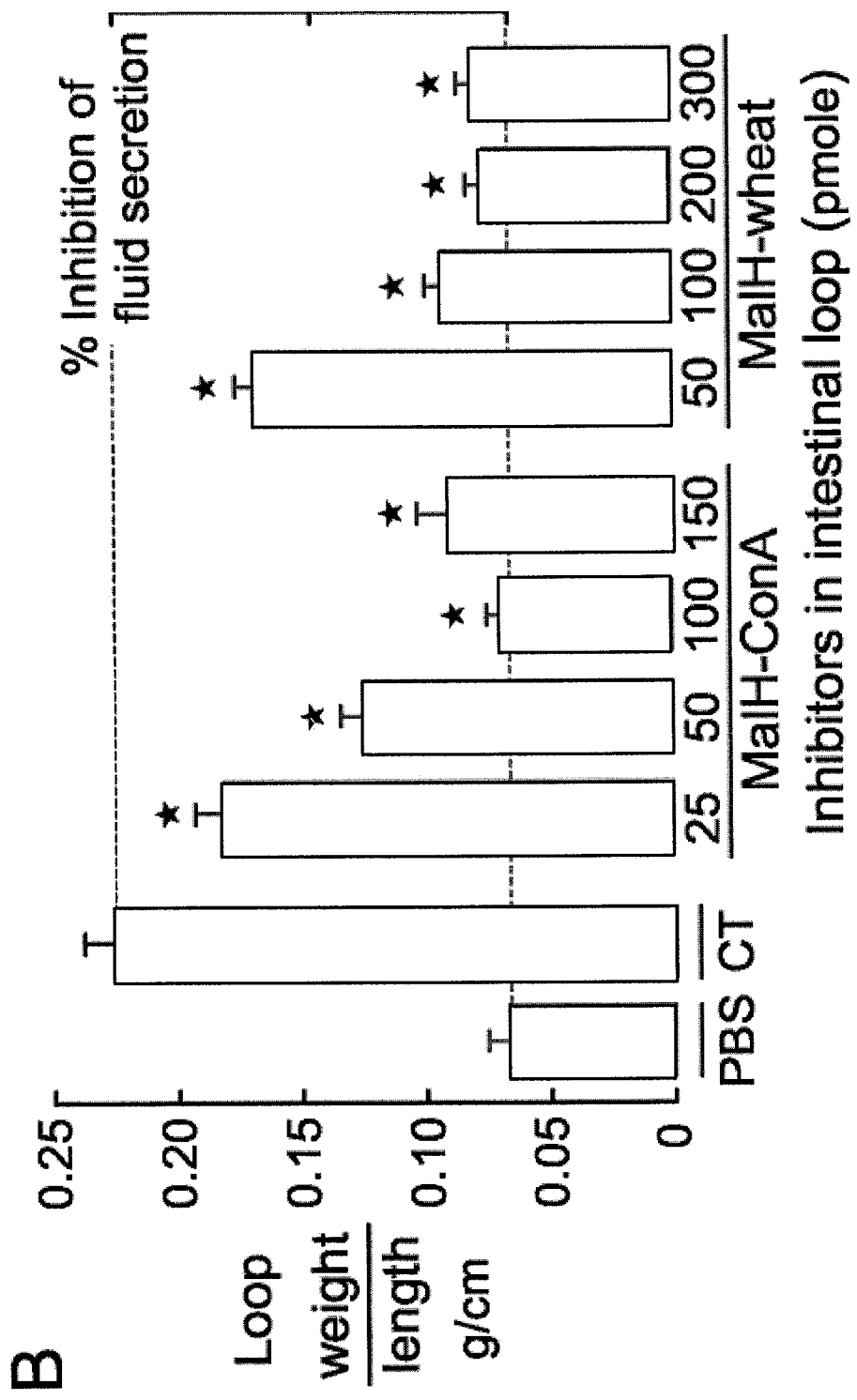

Loops were injected with saline or with cholera toxin containing different concentrations of MalH-ConA or MalH-wheat. Intestinal fluid accumulation at 6 h was measured. The data are presented in FIG. 6B. A loop weight to length ratio of approximately 0.07 g/cm, corresponding to 100% inhibition, was observed when the intestinal loops were injected with PBS, and a loop weight to length ratio of approximately 0.22 g/cm, corresponding to 0% inhibition was measured in cholera toxin-injected loops. MalH-ConA and MalH-wheat inhibited loop secretion in a dose-dependent manner with $EC_{50}$ of approximately 50 µmol/loop and 100 µmol/loop, respectively. Intestinal fluid absorption was also measured as described (Thiagarajah et al., *Gastroenterology* 126:511-19 (2004)) in which the amount of glucose-containing fluid absorbed in 20 min from closed intestinal loops was determined. Absorption was not significantly impaired by 500 nM MalH-ConA (44±4% vs. 41±3%).

Antidiarrheal studies were performed using a suckling mouse model of cholera. Equal numbers of newborn Balb-C mice from the same mother(s), each weighing 2-3 g (age 3-4 days), were gavaged using PE-10 tubing with 10 µg cholera toxin in a 50 µL volume containing 50 mM Tris, 200 mM NaCl and 0.08% Evans blue (pH 7.5) with or without MalH- ConA or MalH-wheat at 125 μmol, as modified from prior protocols (see Takeda et al., *Infect. Immun.* 19:752-754 (1978)). Some control mice were gavaged with buffer alone. Successful gastrointestinal gavage was confirmed by Evans blue localization. Mouse survival was determined hourly.

Figure 6C:
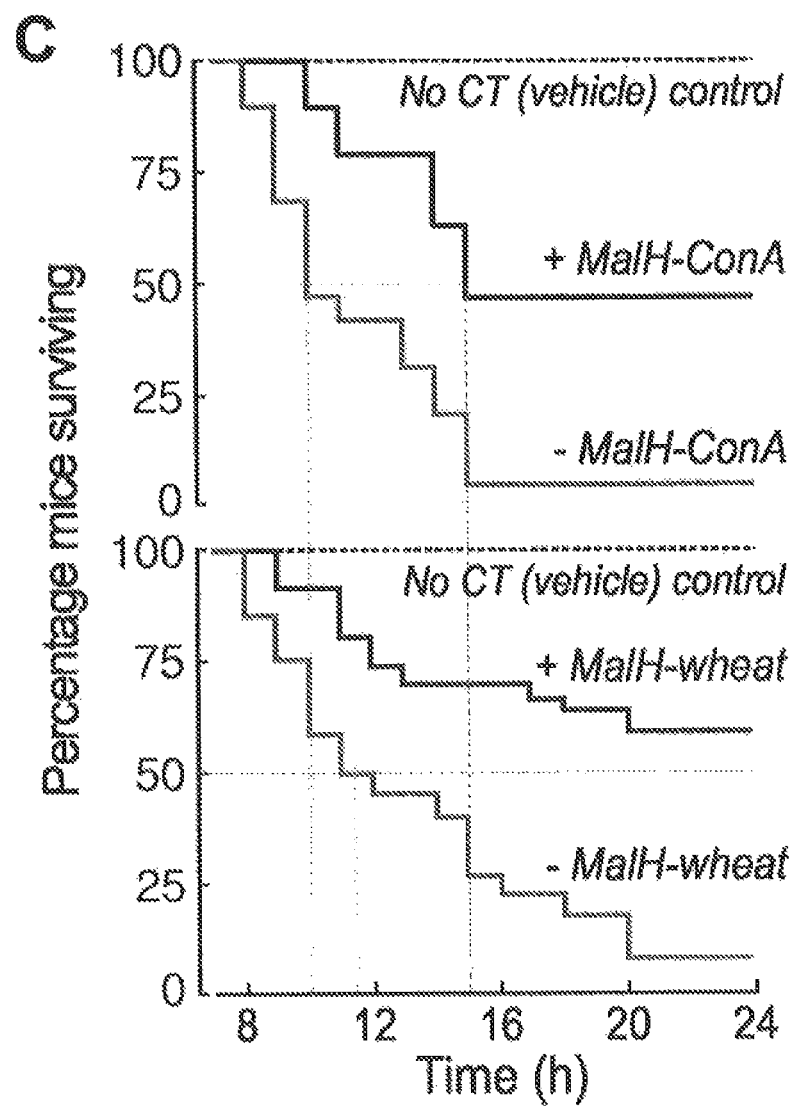
Figure 7A:
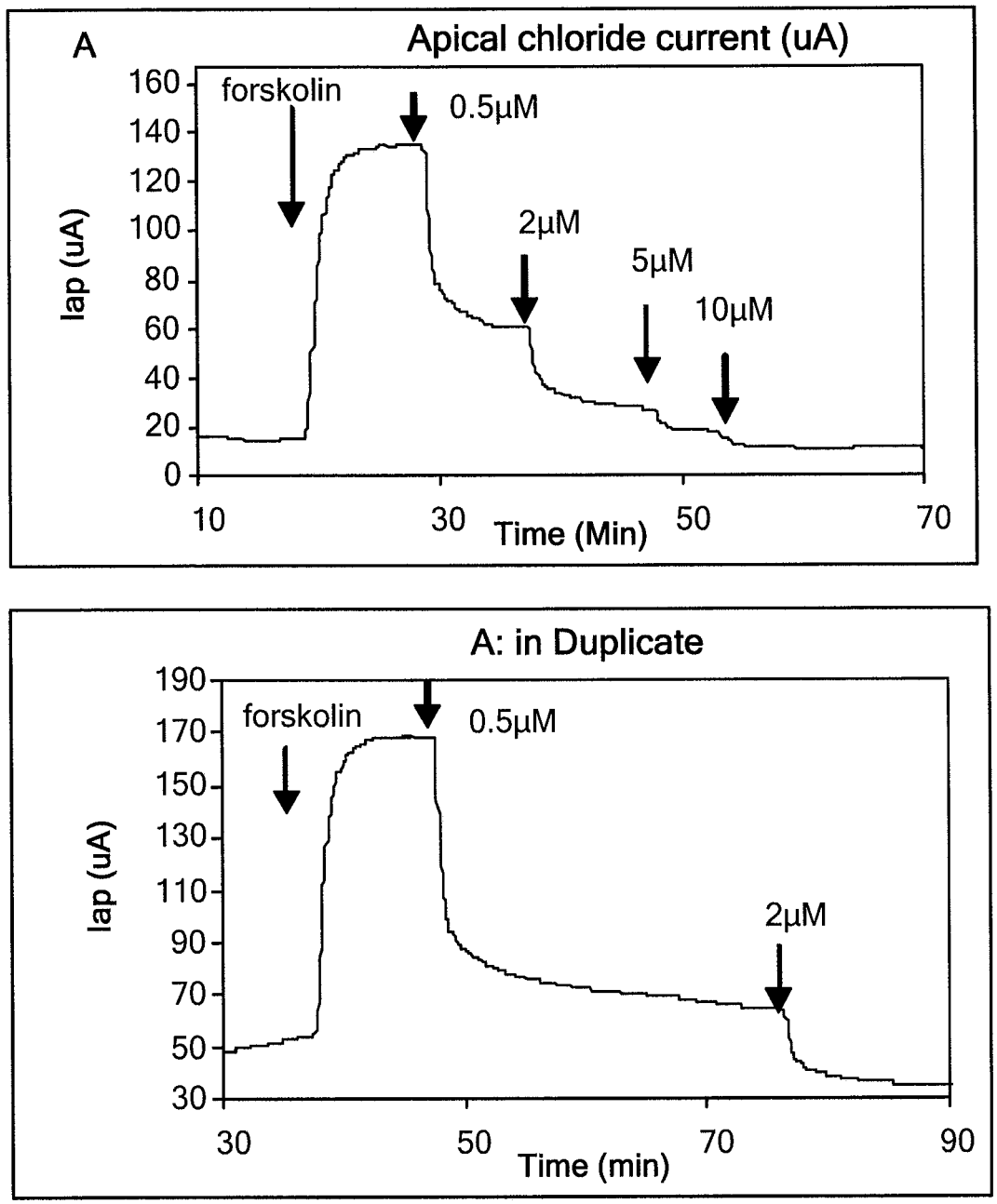
FIGS. 7A-D represent the effect on activity of CFTR by chlorophenyl-malonic hydrazide compounds conjugated to lectins.
Figure 7B:
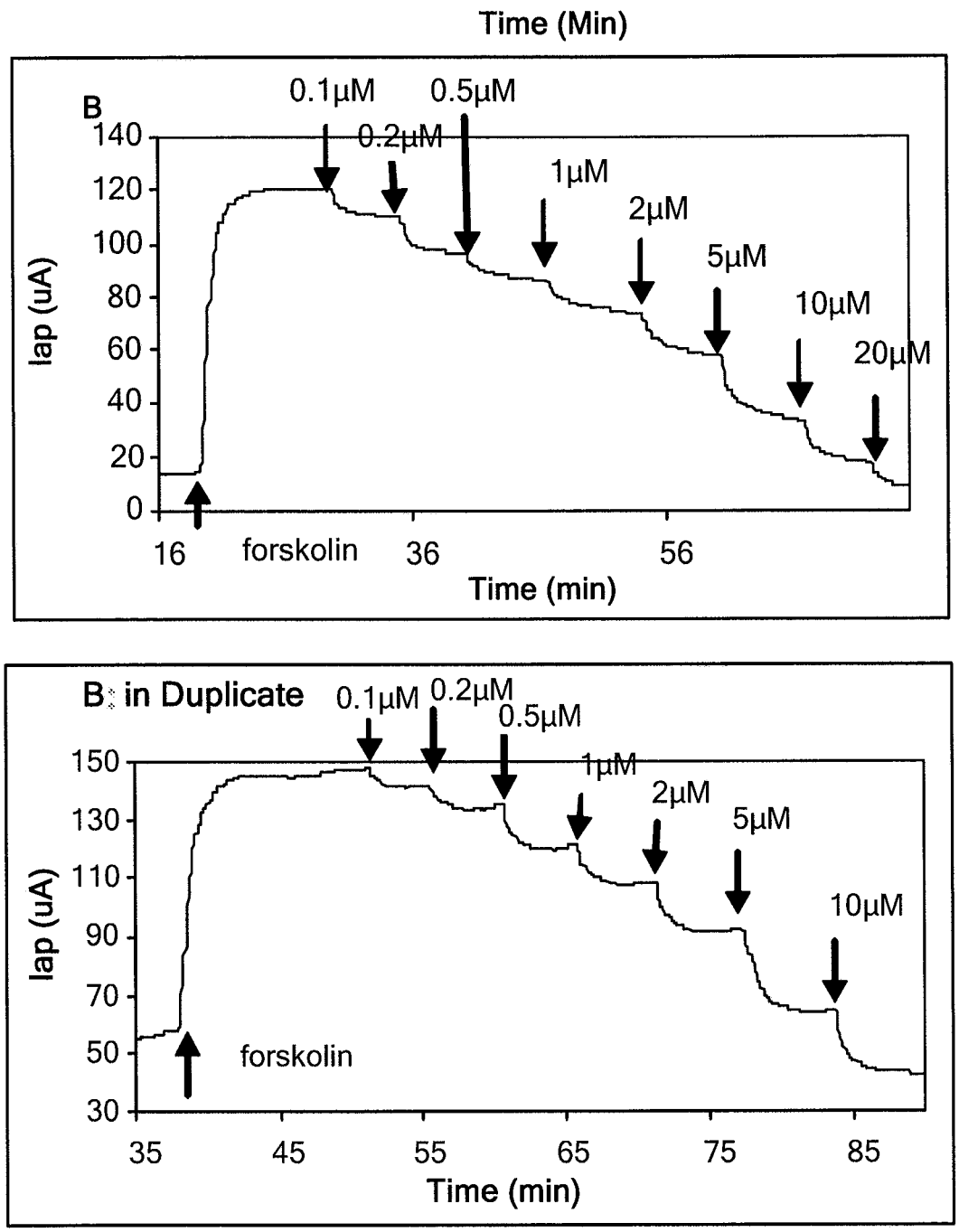
Figure 7C:
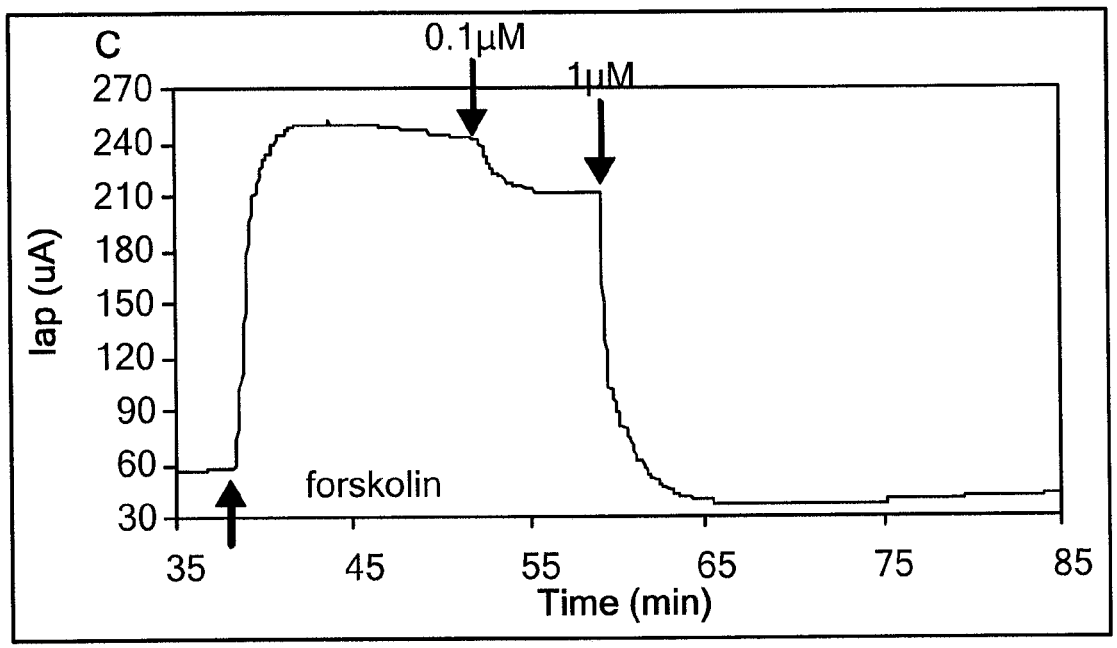
Figure 7D:
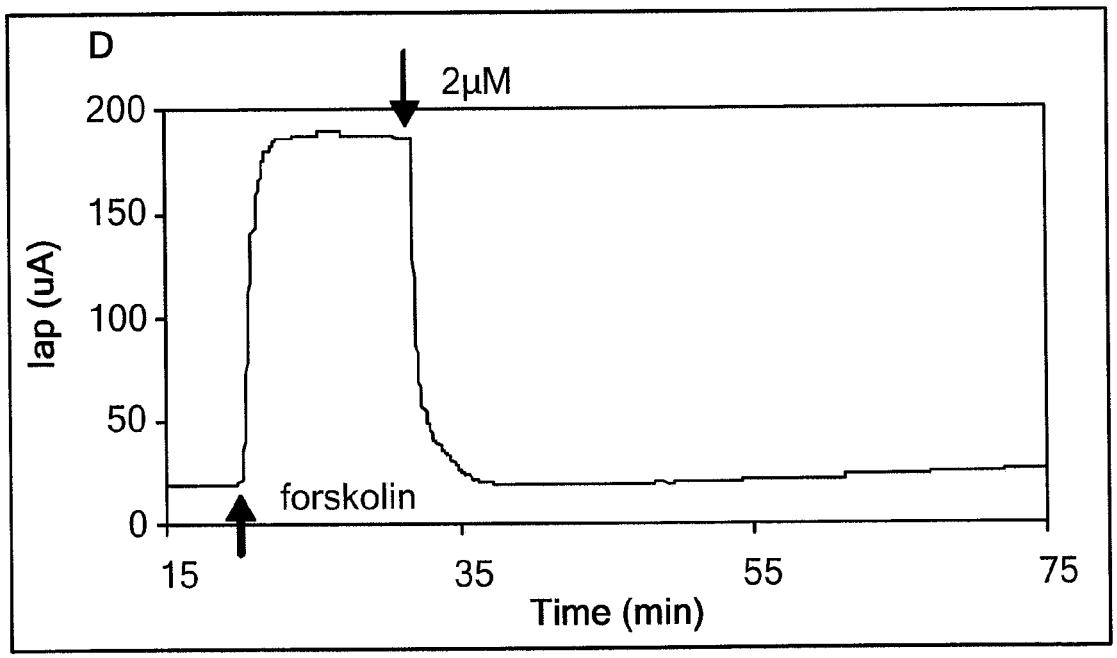

In initial studies, the mouse strain, gavage conditions, and cholera toxin dose were optimized to produce mortality in most cholera toxin-treated mice within 12 h, with no mortality in control mice at 24 h. Suckling Balb-C mice were gavaged with either vehicle or cholera toxin solution, with or without MalH-ConA or MalH-wheat. As summarized in FIG. 6C, all mice gavaged with vehicle alone survived to 24 h, whereas nearly all cholera toxin-treated mice died over this time. Inclusion of either MalH-ConA or MalH-wheat significantly improved survival in the cholera toxin-treated mice ($p<0.001$).

reflux, 2 hr, 57%; (d) 4,4'-diisothiocyanatostilbene-2,2'-disulfonic acid, TEA, reflux 2 h, 44%; (e) lectin, pH 8.5 (100 mM carbonate), 3 h.

Cl-Ph-MalH refers to the malonic acid hydrazide compound having 4-chlorophenyl as the $R^1$ substituent as shown in the reaction scheme. This compound was conjugated to Concanavalin A (D), wheat germ lectin (B), or tomato lectin (C). D refers to Cl-Ph-MalH conjugated to the linker DIDS. The capability of these conjugates to inhibit CFTR activity was determined in a Ussing chamber. The data are presented in FIG. 7.

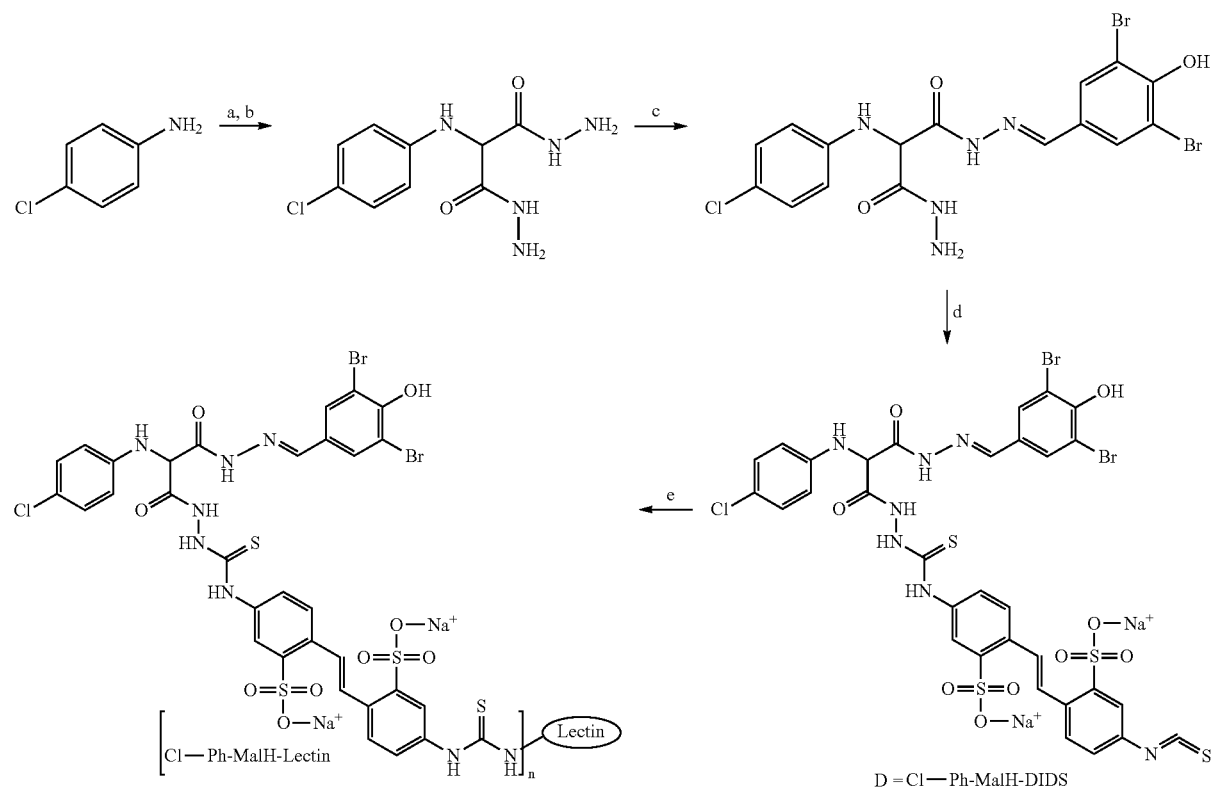

A = Cl—Ph-MalH-ConA (from Concanavalin A)
B = Cl—Ph-MalH-Wheat (from Wheat lectin)
C = Cl—Ph-MalH-Tomato (from Tomato lectin)

Example 7

Conjugation of Lectins to 4-Chlorophenyl-MalH

This Example describes conjugation of a 4-chlorophenyl malonic hydrazide compound via DIDS to Concanavalin A, wheat lectin and tomato lectin.

The following reaction scheme was used for preparing the conjugates. Conjugation was performed similarly to the method described in Example 1. Reagents and conditions included: a, Ethyl bromo malonate, triethylamine (TEA), ethanol, reflux, 8 hr, 55%; (b) hydrazine, methanol, reflux, 2 h, 68%; (c) 3,4-dibromo-4-hydroxybenzaldehyde, ethanol,

Example 8

Conjugation of Synthetic Polymers to Malonic Acid Hydrazide Compounds

This Example describes conjugation of synthetic polymers to malonic hydrazide compounds.

Malonic acid hydrazide compounds were attached at multiple sites to the dendrimer PAMAM™ (Dendritech® Inc., Midland, Mich.). The reaction scheme is shown below. Reagents and conditions included as follows: a) triethyl amine (TEA), ethanol, reflux, 8 hr, 59%. Short circuit current experiments were then performed with the MalH-PAMAM conjugate as described in Example 2. The MalH-PAMAM bioactive agent inhibited CFTR activity. The "R" attached to PAMAM indicates the R structure shown in the box.

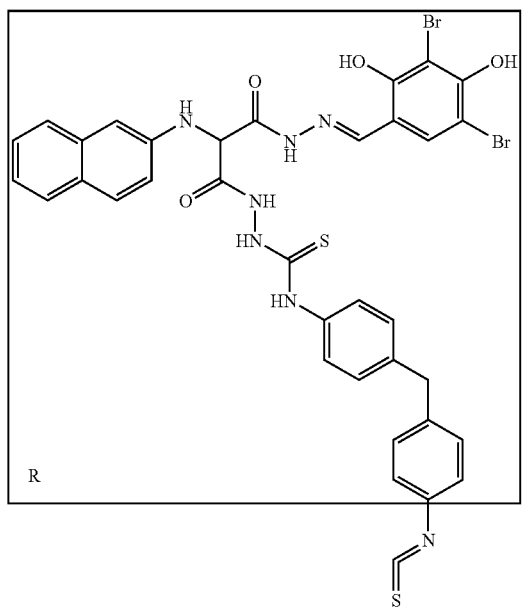
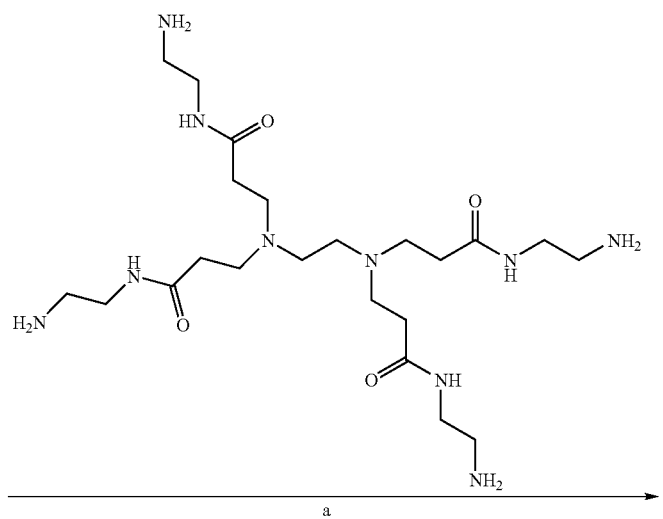
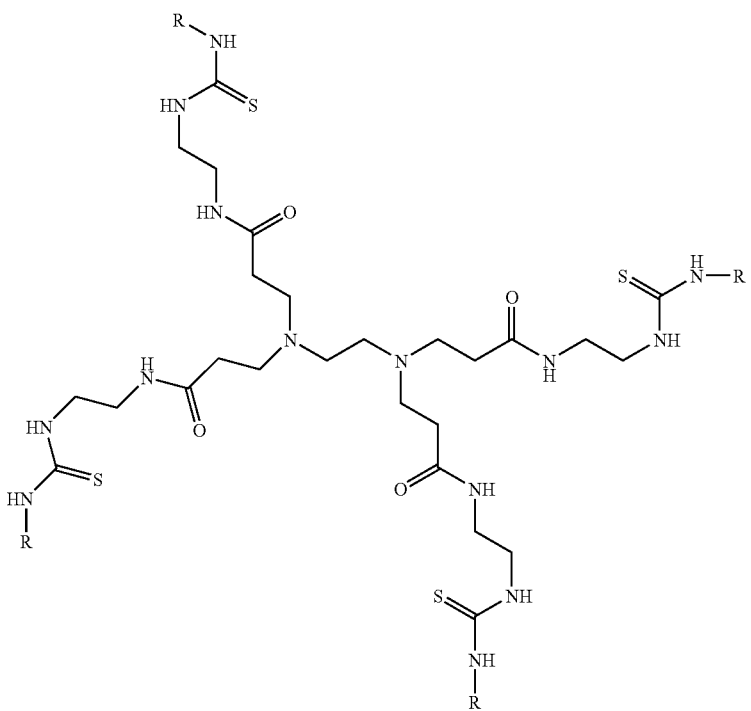

Dendrimers conjugated to a hydrazide compound are also prepared according to the reaction scheme below, using an ethylene spacer/linker.

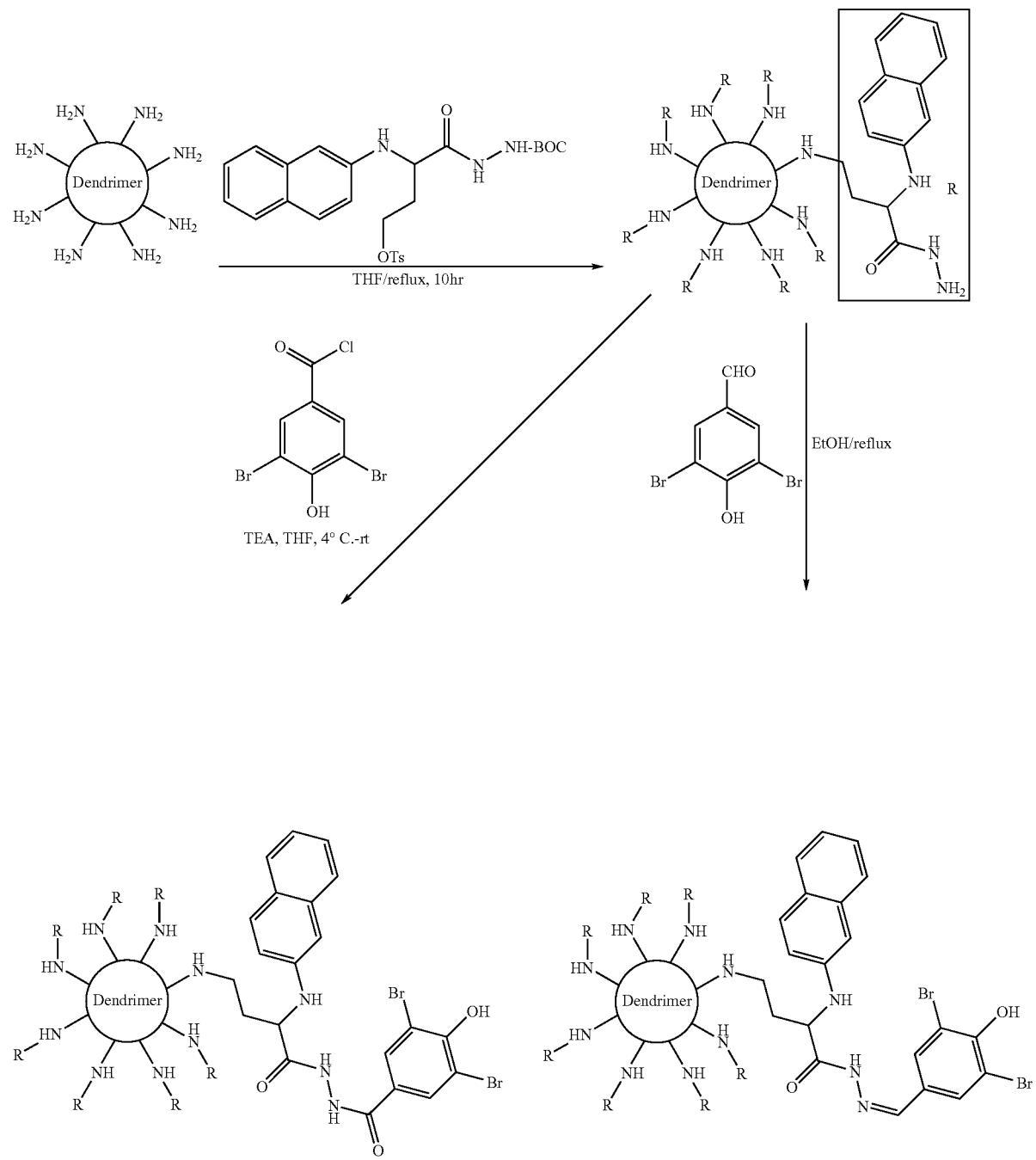

A Mal-H polyethyleneimine (PEI) conjugate is also prepared. The spacer J having the structure J30 is used to link the MalH compound to PEI as shown in the reaction schematic below. Reagents and conditions: a, triethyl amine (TEA), ethanol, reflux, 8 hr. The "R" attached to PEI indicates R structure shown in the box.

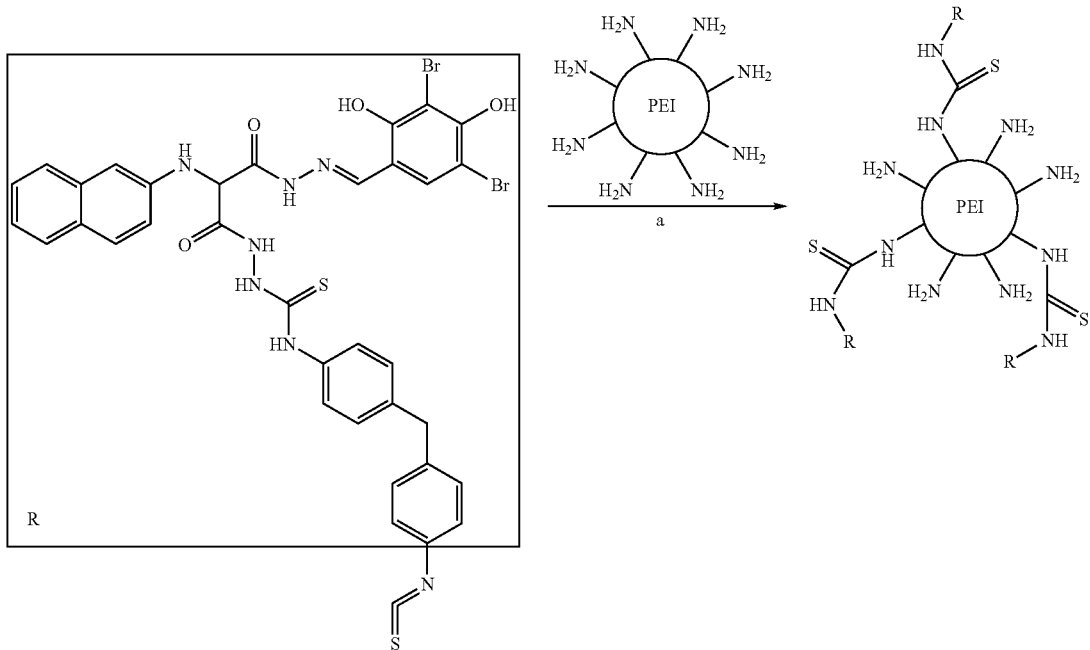
A general reaction scheme for a hydrazide compound disclosed herein that is conjugated to a polymer is shown below. Reagents and conditions for the reaction include: a, polymers (PEI/PAMAM), triethyl amine (TEA), ethanol, reflux, 6-9 hrs.
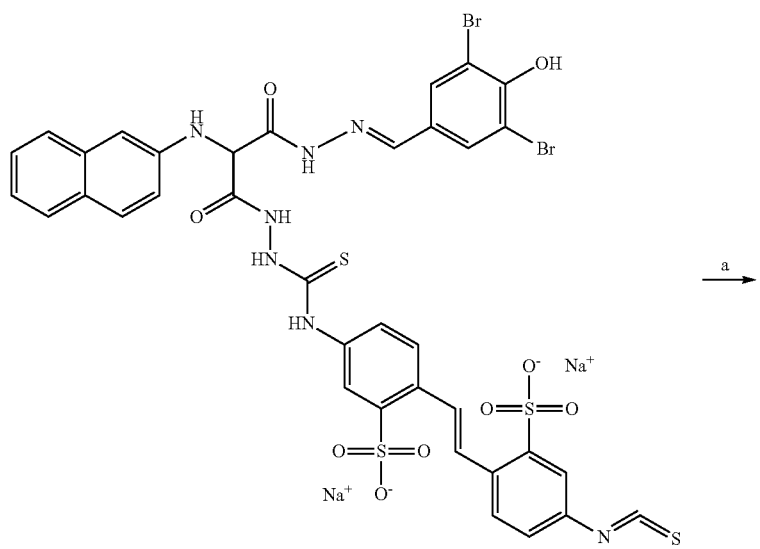

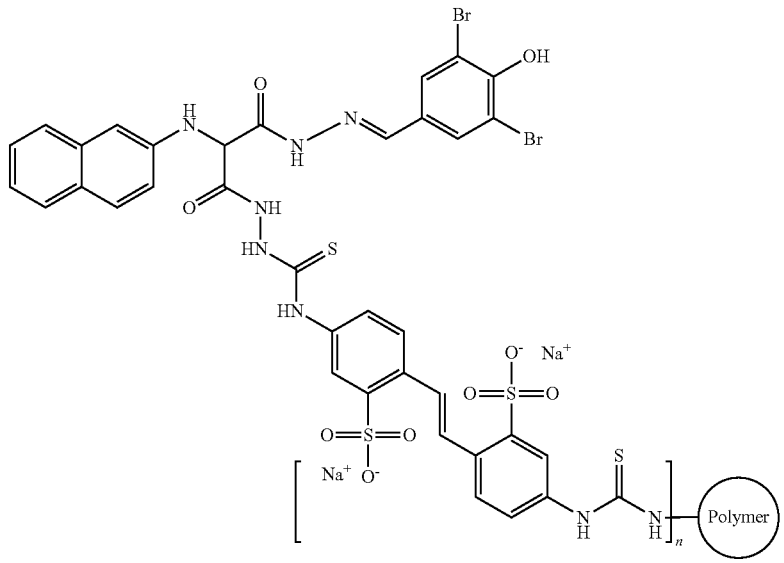

n~8: MalH-PEI-800
n~8: MalH-PEI-3900
n = 3-4: MalH-PAMAM-Generation 0

Example 9

Conjugation of a Macromolecule to Malonic Acid Hydrazide Compounds by Photoactivation A photoactivatable form of a hydrazide compound is prepared according to the following conditions and reaction scheme shown below. The reaction scheme is shown below. The compound 4-azidophenyl isothiocyante acts as a hetero-bi-functional linker.

Reagents and conditions: a, Methyl bromo malonate, triethyl amine (TEA), Ethanol, reflux, 8 hr, 64%; (b) Hydrazine, Methanol, Reflux, 2 h, 62%; (c) 3,4-dibromo-4-hydroxybenzaldehyde, ethanol, reflux, 2 hr, 44%; (d) 4-azidophenyl isothiocyante, TEA, reflux 2 h, 43%; (e) macromolecule, UV, 5 min.

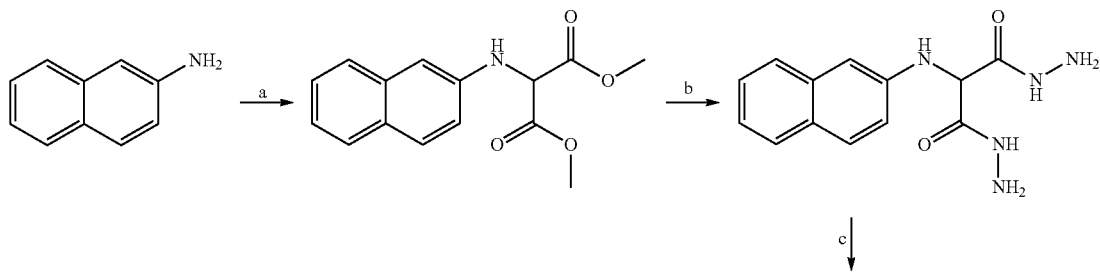

-continued

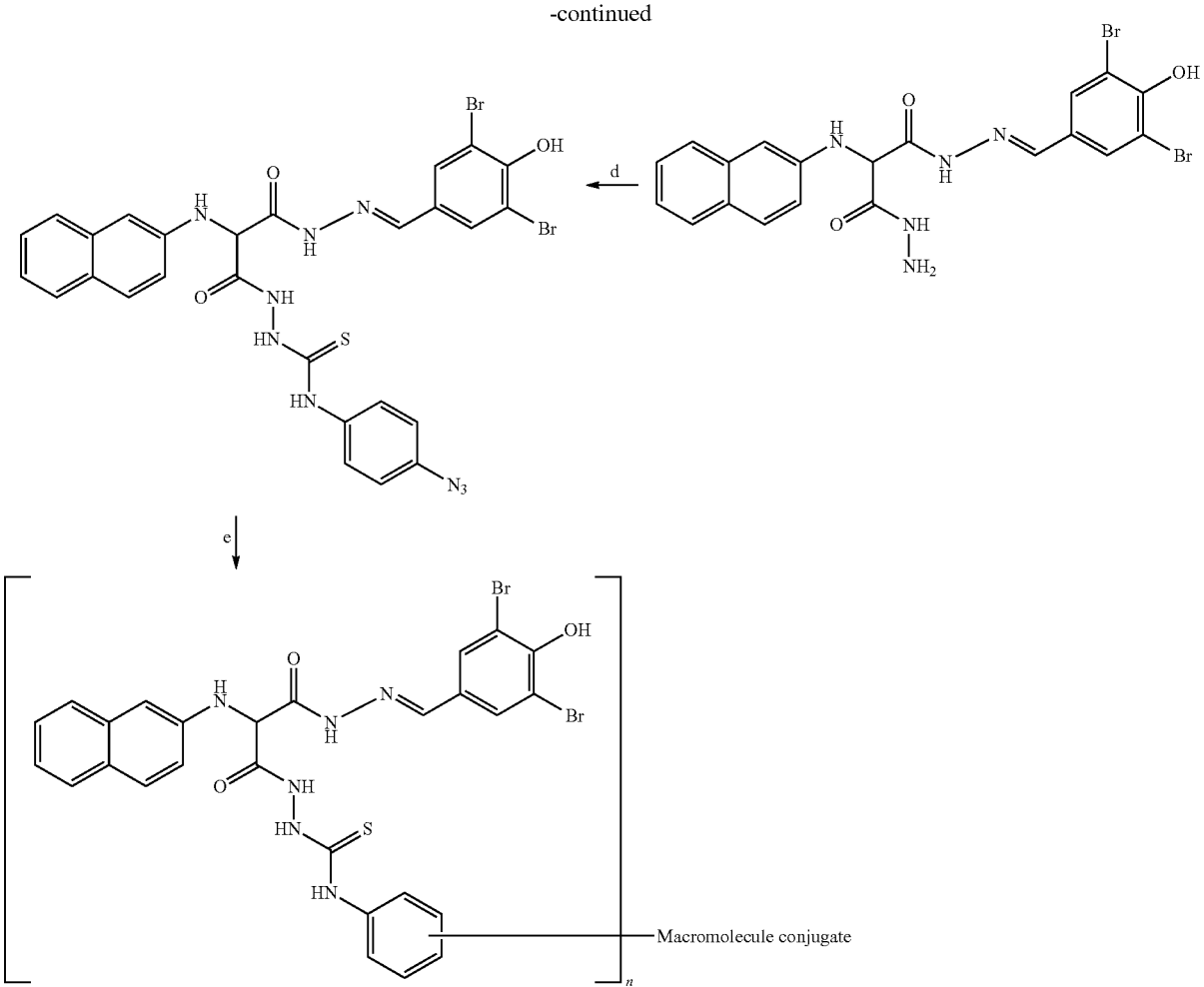

All the above U.S. patents, U.S. patent application publications, U.S. patent applications, foreign patents, foreign patent applications, and non-patent publications referred to in this specification and/or listed in the Application Data Sheet, are incorporated herein by reference, in their entirety.

From the foregoing it will be appreciated that, although specific embodiments have been described herein for purposes of illustration, various modifications may be made. Those skilled in the art will recognize, or be able to ascertain, using no more than routine experimentation, many equivalents to the specific embodiments described herein. Such equivalents are intended to be encompassed by the following claims. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim the following:

1. A bioactive agent having the formula I(b)[(A2)-(J$_{n'}$)]$_n$-M, wherein A2 is a compound that inhibits activity of the cystic fibrosis transmembrane conductance regulator protein (CFTR); J is a spacer; and M is a macromolecular moiety capable of interacting with a cell that expresses CFTR, or a pharmaceutically acceptable salt or stereoisomer thereof, such that the bioactive agent has the formula I(b): [(A2)-(J$_{n'}$)]$_n$-M as follows:

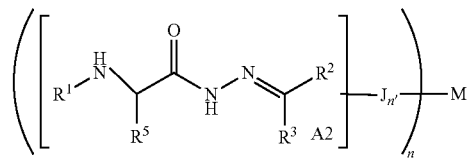

wherein
$R^1$ is phenyl or naphthalenyl;
$R^2$ is phenyl, optionally substituted with any one or more of hydroxyl, $C_{1-8}$ alkyl, $C_{1-8}$ alkoxy, carboxy, halo, or nitro;
$R^3$ is H or $C_{1-8}$ alkyl;
$R^4$ is H;
$R^5$ is H, alkyl, phenyl, carboxy, aryl, heteroaryl, —C(=O)NHNR$^9$R$^{10}$, —C(=O)NHN(=R$^9$), —NR$^9$R$^{10}$; —C(=O)NHNHC(=S)NR$^9$R$^{10}$, —C(=O)NHNHC(=O)NR$^9$R$^{11}$, —C(=O)NHNHC(=O)CR$^9$R$^{10}$, —C(=O)R$^9$, —CH$_2$(CH)$_z$R$^9$ wherein z is 0-7, or —CH$_2$CH$_2$NHR$^{11}$;
each of R$^9$, and R$^{10}$ is the same or different and independently H, $C_{1-8}$ alkyl, cycloalkyl, phenyl, or phenylalkyl;

$R^{11}$ is H, $C_{1-8}$ alkyl, cycloalkyl, phenyl, or alkylphenyl;

wherein J is a spacer that comprises a first end and a second end, wherein the spacer is attached to the compound of formula A2 at the first end of the spacer through a first linker functional group and wherein the spacer is attached to the macromolecular moiety M at the second end of the spacer through a second linker functional group, and wherein the first end of the spacer is attached to compound A2 at one or more of $R^3$, $R^4$ or $R^5$;

n=1 to 500 and n'=0 or 1, and wherein when n'=0, M forms a direct bond with at least one of $R^3$, $R^4$ or $R^5$, and wherein M is a lectin.

2. The bioactive agent of claim 1 wherein $R^2$ is substituted phenyl, and wherein the phenyl is substituted with one, two, or three halo; one or two carboxy; one, two, or three hydroxyl; one or two halo and one, two, or three hydroxyl; one or two halo, one or two hydroxyl, and one $C_{1-8}$ alkoxy; one or two halo, one hydroxyl, and one or two $C_{1-8}$ alkoxy; or one halo, one or two hydroxyl, and one or two $C_{1-8}$ alkoxy.

3. The bioactive agent of claim 1 wherein $R^2$ is 2-, 3-, or 4-halophenyl; 3,5-dihalophenyl; 2-, 3-, or 4-hydroxyphenyl; 2,4-dihydroxyphenyl; 3,5-dihalo-2,4,6-trihydroxyphenyl; 3,5-dihalo-2,4-dihydroxyphenyl; 3,5-dihalo-4-hydroxyphenyl; 3-halo-4-hydroxyphenyl; 3,5-dihalo-2-hydroxy-4-methoxyphenyl; or 4-carboxyphenyl.

4. The bioactive agent of claim 3 wherein halo is bromo.

5. The bioactive agent of claim 1 wherein $R^1$ is unsubstituted phenyl, or substituted phenyl wherein phenyl is substituted with one or more of hydroxy, $C_{1-8}$ alkyl, or halo.

6. The bioactive agent of claim 5 wherein halo is chloro.

7. The bioactive agent of claim 5 wherein $R^1$ is substituted phenyl, and wherein phenyl is substituted with methyl.

8. The bioactive agent of claim 1 wherein $R^1$ is 2-naphthalenyl or 1-naphthalenyl, optionally substituted with one or more of halo, hydroxyl, $C_{1-8}$ alkyl, or $C_{1-8}$ alkoxy.

9. The bioactive agent of claims 8 wherein $R^1$ is mono-(halo)naphthalenyl; di-(halo)naphthalenyl; tri-(halo)naphthalenyl; mono-(hydroxy)naphthalenyl; di-(hydroxy)naphthalenyl; tri-(hydroxy)naphthalenyl; mono-(alkoxy) naphthalenyl; di-(alkoxy)naphthalenyl; tri-(alkoxy) naphthalenyl; mono-(alkyl)naphthalenyl; di-(alkyl) naphthalenyl; tri-(alkyl)naphthalenyl; mono-(hydroxy)-naphthalene-sulfonic acid; mono-(hydroxy)-naphthalene-disulfonic acid; mono or di(halo)-mono or di(hydroxy) naphthalenyl; mono-(alkyl)-mono-(alkoxy)-naphthalenyl; or mono-(alkyl)-di-(alkoxy)-naphthalenyl.

10. The bioactive agent of claim 1 wherein $R^1$ is 2-chlorophenyl, 4-chlorophenyl, 2,4-dichlorophenyl, or 4-methylphenyl.

11. The bioactive agent of claim 1 wherein each of $R^3$ and $R^5$ is the same or different and independently hydrogen, methyl, or ethyl.

12. The bioactive agent of claim 1 wherein $R^3$ is hydrogen, or methyl.

13. The bioactive agent of claim 1 wherein $R^2$ is 3,5-dibromo-2,4-dihydroxyphenyl or 3,5-dibromo-4-hydroxyphenyl.

14. The bioactive agent of claim 1 wherein $R^3$ is H and the compound has a structure of formula A6, wherein the first end of J is attached at $R^5$ such that the bioactive agent has the following formula I(f): $[A6-(J)_{n'}]_n-M$:

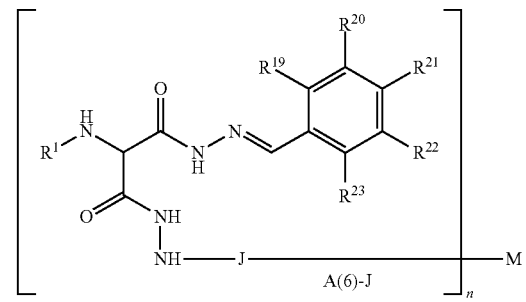

wherein each of $R^{19}$, $R^{20}$, $R^{21}$, $R^{22}$, and $R^{23}$ is the same or different and independently hydrogen, hydroxy, halo, $C_{1-8}$ alkyl, $C_{1-8}$ alkoxy, or carboxy.

15. The bioactive agent of claim 14 wherein each of $R^{20}$ and $R^{22}$ is halo and each of $R^{21}$ and $R^{23}$ is hydroxyl or wherein each of $R^{20}$ and $R^{22}$ is halo and $R^{21}$ is hydroxyl.

16. The bioactive agent of claim 14 wherein halo is bromo.

17. The bioactive agent of claim 14 wherein $R^1$ is 2-naphthalenyl or 1-naphthalenyl, optionally substituted with one or more of halo, hydroxyl, $C_{1-8}$ alkyl, and $C_{1-8}$ alkoxy; 2-chlorophenyl, 2,4-chlorophenyl, 4-chlorophenyl, -2-4-dichlorophenyl, or 4-methylphenyl.

18. The bioactive agent of either claim 1 or claim 14 wherein J is selected from DIDS (4,4'-diisothiocyanatostilbene-2,2'-disulfonic acid), bis(polyethylene glycol bis[imidazoyl carbonyl]); N-((2-pyridyldithio)ethyl)-4-azidosalicylamide; and maleimidoethyl succinimidyl succinate.

19. The bioactive agent of either claim 1 or claim 14 wherein J is selected from any one of the following structures J1-J30:

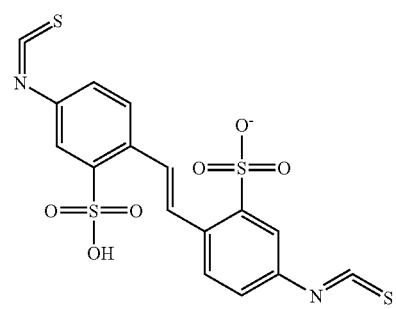

J1

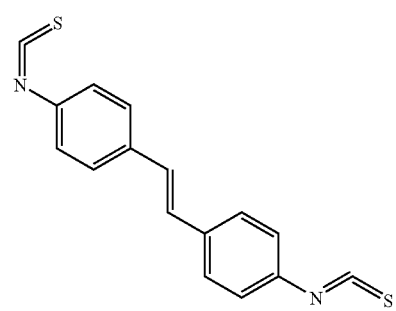

J2

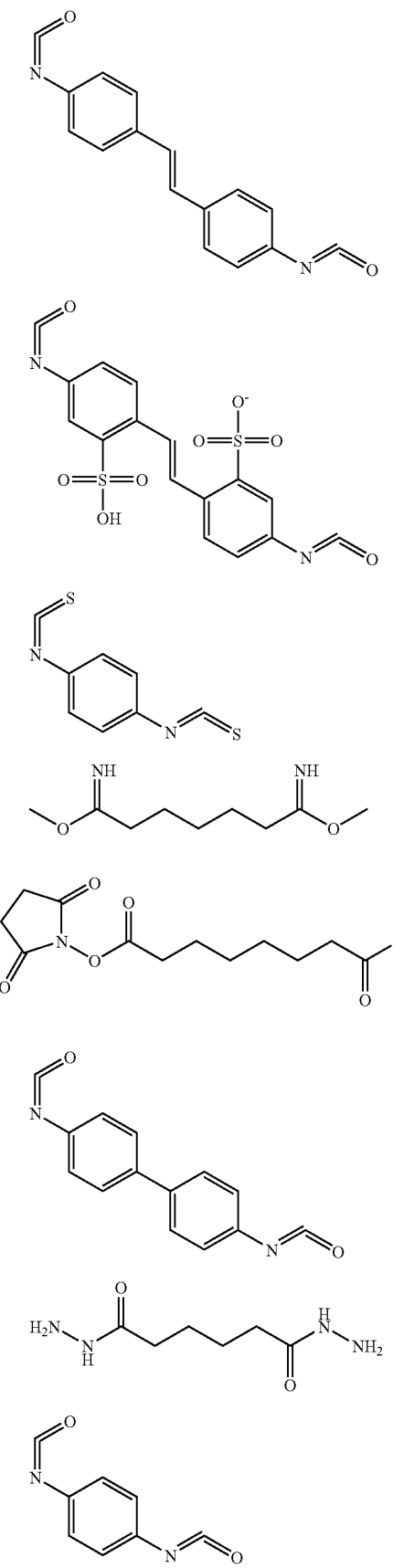
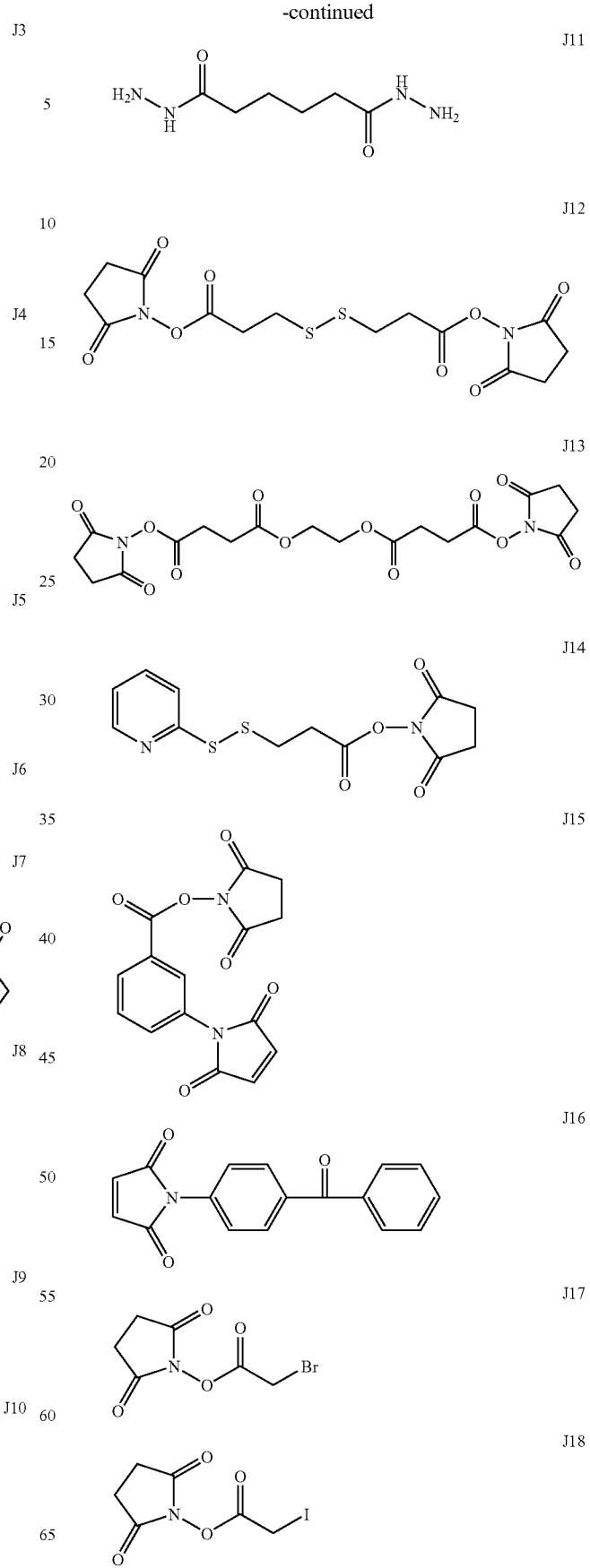

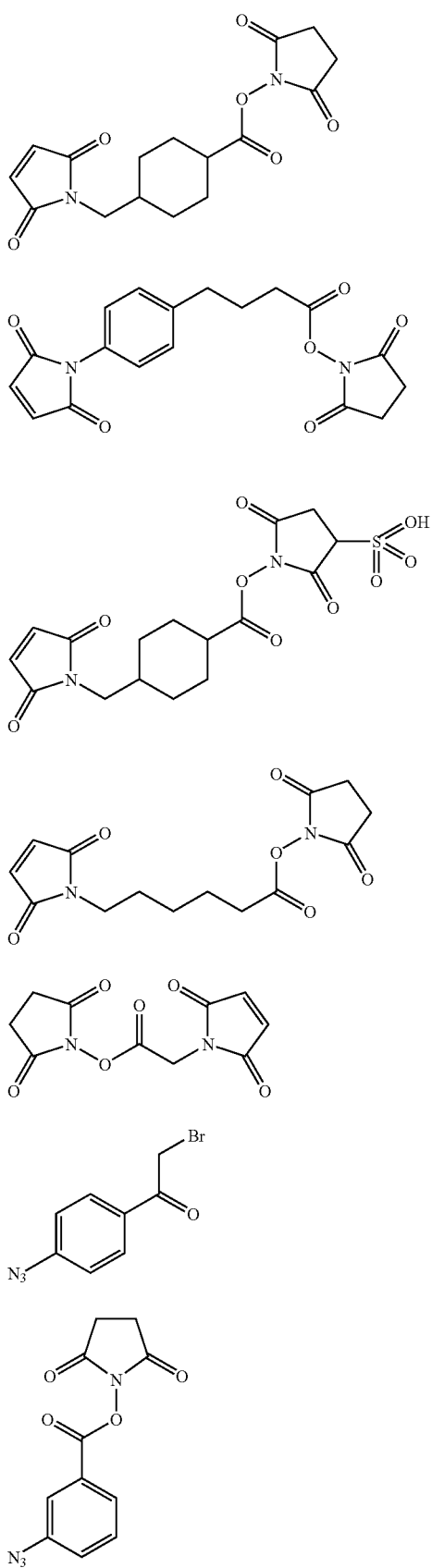
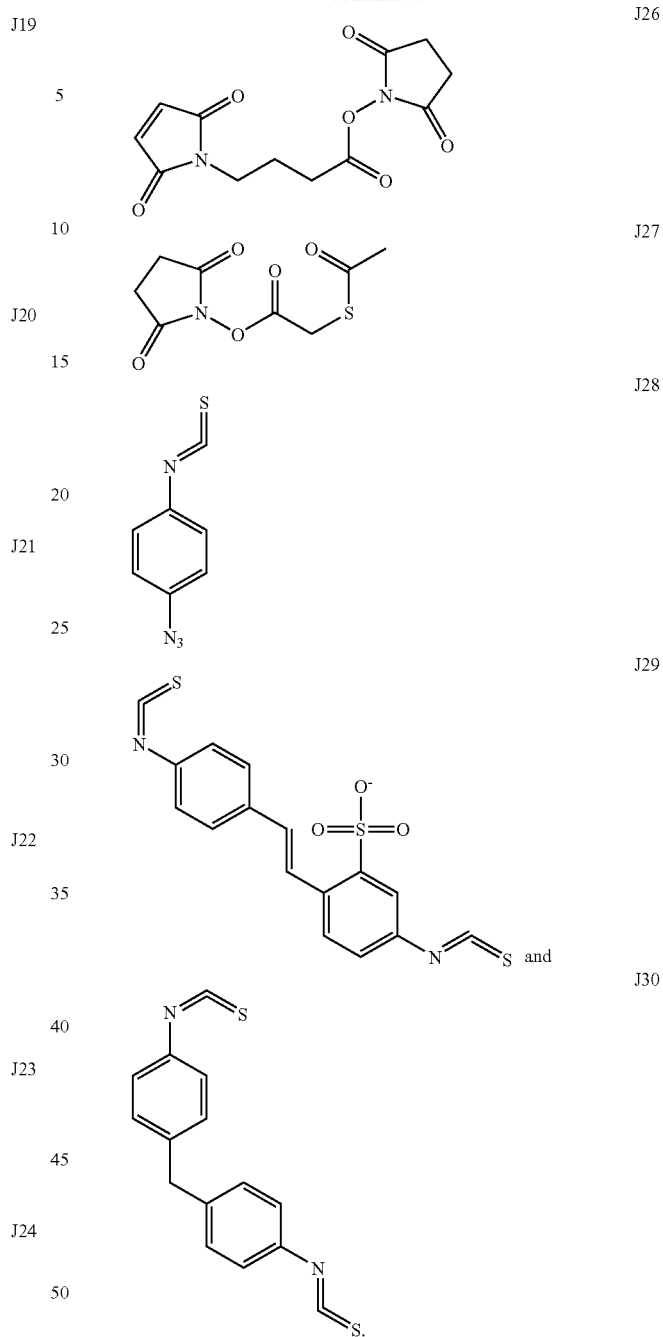

20. The bioactive agent of either claim 1 or claim 14 wherein the lectin is selected from the group consisting of a jack bean lectin, a wheat germ lectin, a tomato lectin, an asparagus pea lectin, a scarlet runner bean lectin, a pea lectin, a chick pea lectin, soybean lectin, and lentil lectin, and a potato lectin.

21. The bioactive agent of claim 20 wherein the lectin is a jack bean lectin and wherein the jack bean lectin is Concanavalin A.

22. The bioactive agent of claim 20 wherein the lectin is a wheat lectin or a tomato lectin.

23. The bioactive agent of claim 14 wherein $R^1$ is 2-naphthalenyl or 4-chlorophenyl, $R^{19}$ and $R^{23}$ are H, $R^{20}$ and $R^{22}$ are bromo, $R^{21}$ is hydroxyl, J is DIDS, and M is a lectin, and wherein the bioactive agent has a structure of the following formula I(g) or I(h):

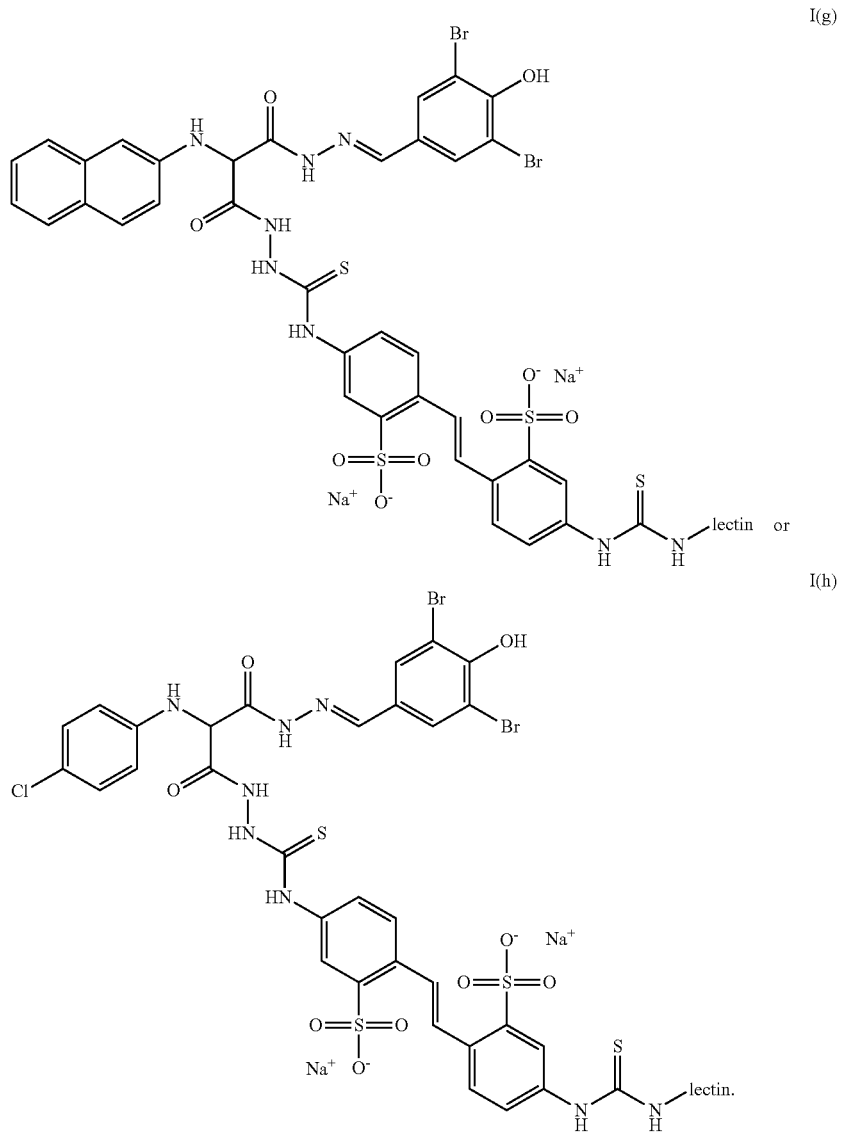

24. The bioactive agent of claim 23 wherein the lectin is selected from the group consisting of a jack bean lectin, a wheat lectin, a tomato lectin, an asparagus pea lectin, a scarlet runner bean lectin, a pea lectin, a chick pea lectin, a soybean lectin, a lentil lectin, and a potato lectin.

25. A composition comprising the bioactive agent of either claim 1 or claim 14 and a pharmaceutically acceptable excipient.

26. A method of treating a disease or disorder associated with aberrantly increased ion transport by cystic fibrosis transmembrane conductance regulator (CFTR), the method comprising administering to a subject the composition according to claim 25, wherein ion transport by CFTR is inhibited.

27. The method according to claim 26 wherein the disease or disorder has aberrantly increased intestinal fluid secretion.

28. The method according to claim 26 wherein the disease or disorder is secretory diarrhea.

29. The method according to claim 28 wherein secretory diarrhea is caused by an enteric pathogen.

30. The method according to claim 29 herein the enteric pathogen is *Vibrio cholerae, Clostridium difficile, Escherichia coli, Shigella, Salmonella*, rotavirus, *Giardia lamblia, Entamoeba histolytica, Campylobacter jejuni*, and *Cryptosporidium*.

31. The method according to claim 28 wherein the secretory diarrhea is induced by an enterotoxin.

32. The method according to claim 31 wherein the enterotoxin is a cholera toxin, a *E. coli* toxin, a *Salmonella* toxin, a *Campylobacter* toxin, or a *Shigella* toxin.

33. The method of claim 31 wherein secretory diarrhea is a sequelae of ulcerative colitis, irritable bowel syndrome (IBS), AIDS, chemotherapy, or an enteropathogenic infection.

34. The method of claim 26 wherein the subject is a human or non-human animal.

35. A method of inhibiting ion transport by a cystic fibrosis transmembrane conductance regulator (CFTR) comprising contacting (a) a cell that comprises CFTR and (b) the bioactive agent of either claim 1 or claim 14, under conditions and for a time sufficient for the CFTR and the compound to interact, thereby inhibiting ion transport by CFTR.

36. A method of treating secretory diarrhea comprising administering to a subject a pharmaceutically acceptable excipient and a bioactive agent according to claim 1.

37. The method of claim 36 wherein the subject is a human or non-human animal.

\* \* \* \* \*